United States Patent
Yuba et al.

(10) Patent No.: US 11,333,976 B2
(45) Date of Patent: May 17, 2022

(54) RESIN, PHOTOSENSITIVE RESIN COMPOSITION, ELECTRONIC COMPONENT AND DISPLAY DEVICE USING THE SAME

(71) Applicant: TORAY INDUSTRIES, INC., Tokyo (JP)

(72) Inventors: Tomoyuki Yuba, Otsu (JP); Yuki Masuda, Otsu (JP); Jiake Jin, Shanghai (CN); Ping Li, Shanghai (CN)

(73) Assignee: TORAY INDUSTRIES, INC., Tokyo (JP)

( * ) Notice: Subject to any disclaimer, the term of this patent is extended or adjusted under 35 U.S.C. 154(b) by 19 days.

(21) Appl. No.: 15/545,912

(22) PCT Filed: Jan. 25, 2016

(86) PCT No.: PCT/JP2016/052016
§ 371 (c)(1),
(2) Date: Jul. 24, 2017

(87) PCT Pub. No.: WO2016/121691
PCT Pub. Date: Aug. 4, 2016

(65) Prior Publication Data
US 2018/0011402 A1    Jan. 11, 2018

(30) Foreign Application Priority Data

Jan. 27, 2015 (JP) .............................. JP2015-012924
Mar. 26, 2015 (CN) .......................... 201510134502.8
Mar. 26, 2015 (CN) .......................... 201510134581.2

(51) Int. Cl.
*G03F 7/023* (2006.01)
*G03F 7/40* (2006.01)
(Continued)

(52) U.S. Cl.
CPC ............ *G03F 7/0233* (2013.01); *C07C 25/18* (2013.01); *C07C 41/22* (2013.01); *C07C 67/307* (2013.01);
(Continued)

(58) Field of Classification Search
CPC ...... G03F 7/0392; G03F 7/0387; G03F 7/037; G03F 7/0233; G03F 7/039; G03F 7/40; C08G 69/26
(Continued)

(56) References Cited

U.S. PATENT DOCUMENTS 5,202,411 A    4/1993  Itatani
6,528,231 B1 *  3/2003  Tajima .................. G03F 7/0387
                                                    430/270.1
(Continued)

FOREIGN PATENT DOCUMENTS

EP    0 424 940 A2    5/1991
JP    2-283762 A     11/1990
(Continued)

OTHER PUBLICATIONS

Chang et al., "Synthesis of Polyphenyls", Tetrahedron, vol. 69, 2013 (Available online Oct. 23, 2012), pp. 228-234.
(Continued)

*Primary Examiner* — John S Chu
(74) *Attorney, Agent, or Firm* — Birch, Stewart, Kolasch & Birch, LLP

(57) ABSTRACT

A resin having a small linear thermal expansion coefficient and a low absorbance is provided. The resin is characterized by including at least one structure selected from structures represented by the following general formulae (1) and (2):
(Continued)

[Chemical Formula 1]

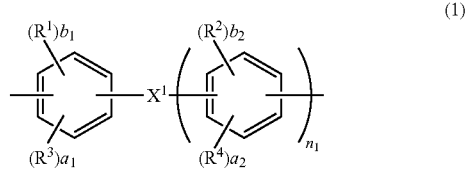

(1)

[Chemical Formula 2]

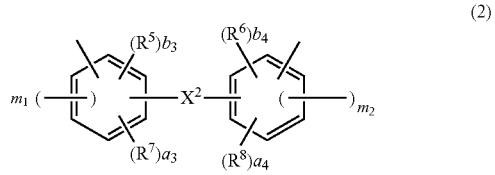

(2)

14 Claims, 6 Drawing Sheets

(51) Int. Cl.
| | |
|---|---|
| C08G 69/32 | (2006.01) |
| C07C 209/74 | (2006.01) |
| C07C 231/02 | (2006.01) |
| C07D 209/48 | (2006.01) |
| C07D 263/62 | (2006.01) |
| C07C 231/12 | (2006.01) |
| H01L 21/027 | (2006.01) |
| C07C 41/22 | (2006.01) |
| H01L 23/31 | (2006.01) |
| H05K 3/34 | (2006.01) |
| C07C 213/00 | (2006.01) |
| C07C 211/56 | (2006.01) |
| C08G 73/10 | (2006.01) |
| G03F 7/037 | (2006.01) |
| C09D 179/08 | (2006.01) |
| C07C 67/307 | (2006.01) |
| C07C 269/06 | (2006.01) |
| C09D 179/04 | (2006.01) |
| G03F 7/039 | (2006.01) |
| C07C 25/18 | (2006.01) |
| C07C 215/80 | (2006.01) |
| C07D 263/56 | (2006.01) |
| C08G 73/22 | (2006.01) |
| G03F 7/16 | (2006.01) |
| G03F 7/20 | (2006.01) |
| G03F 7/32 | (2006.01) |
| H01L 23/29 | (2006.01) |
| H01L 27/12 | (2006.01) |
| H05K 1/02 | (2006.01) |
| H01L 27/32 | (2006.01) |

(52) U.S. Cl.
CPC .......... *C07C 209/74* (2013.01); *C07C 211/56* (2013.01); *C07C 213/00* (2013.01); *C07C 215/80* (2013.01); *C07C 231/02* (2013.01); *C07C 231/12* (2013.01); *C07C 269/06* (2013.01); *C07D 209/48* (2013.01); *C07D 263/56* (2013.01); *C07D 263/62* (2013.01); *C08G 69/32* (2013.01); *C08G 73/106* (2013.01); *C08G 73/1017* (2013.01); *C08G 73/1039* (2013.01); *C08G 73/1042* (2013.01); *C08G 73/1075* (2013.01); *C08G 73/1082* (2013.01); *C08G 73/22* (2013.01); *C09D 179/04* (2013.01); *C09D 179/08* (2013.01); *G03F 7/037* (2013.01); *G03F 7/039* (2013.01); *G03F 7/162* (2013.01); *G03F 7/168* (2013.01); *G03F 7/2004* (2013.01); *G03F 7/322* (2013.01); *G03F 7/40* (2013.01); *H01L 21/027* (2013.01); *H01L 23/293* (2013.01); *H01L 23/3157* (2013.01); *H01L 23/3171* (2013.01); *H01L 27/1248* (2013.01); *H05K 1/0298* (2013.01); *H05K 3/3452* (2013.01); *H01L 27/3258* (2013.01); *H01L 2224/11* (2013.01); *H01L 2224/16145* (2013.01); *H01L 2224/32145* (2013.01); *H01L 2224/48463* (2013.01); *H01L 2224/73204* (2013.01); *H01L 2224/73265* (2013.01)

(58) Field of Classification Search
USPC ..................................... 430/192, 193, 270.1
See application file for complete search history.

(56) References Cited

U.S. PATENT DOCUMENTS

| | | | | |
|---|---|---|---|---|
| 7,026,080 | B2 * | 4/2006 | Nakayama | C08L 79/08 430/18 |
| 7,150,947 | B2 * | 12/2006 | Nunomura | G03F 7/0233 430/18 |
| 8,883,391 | B2 * | 11/2014 | Miyabe | C08L 79/08 430/165 |
| 2003/0194621 | A1 | 10/2003 | Tajima et al. | |
| 2006/0229384 | A1 * | 10/2006 | Sakayori | C03C 17/32 523/160 |
| 2009/0263745 | A1 * | 10/2009 | Sakayori | C08G 73/10 430/281.1 |
| 2011/0086311 | A1 * | 4/2011 | Katayama | C08G 73/10 430/280.1 |
| 2011/0151195 | A1 * | 6/2011 | Mitsukura | G03F 7/0388 428/156 |
| 2012/0070781 | A1 * | 3/2012 | Katayama | C07D 295/18 430/281.1 |
| 2013/0126860 | A1 * | 5/2013 | Fukuda | C08L 79/08 257/43 |
| 2013/0137036 | A1 * | 5/2013 | Jeong | H01L 23/293 430/283.1 |
| 2014/0065526 | A1 * | 3/2014 | Chen | G03F 7/022 430/18 |

FOREIGN PATENT DOCUMENTS

| | | |
|---|---|---|
| JP | 2002-341169 A | 11/2002 |
| JP | 2003-212996 A | 7/2003 |

OTHER PUBLICATIONS

Goto et al., "Double Helix Formation of Oligoresorcinols in Water: Thermodynamic and Kinetic Aspects", J. Am. Chem. Soc., vol. 131, No. 13, 2009 (Published on Web Mar. 13, 2009), pp. 4710-4719.

Liaw et al., "Advanced Polyimide Materials: Syntheses, Physical Properties and Applications", Progress in Polymer Science, vol. 37, 2012 (Available online Mar. 1, 2012), pp. 907-974.

* cited by examiner

6a

6b

6c

6d

6e

RESIN, PHOTOSENSITIVE RESIN COMPOSITION, ELECTRONIC COMPONENT AND DISPLAY DEVICE USING THE SAME

TECHNICAL FIELD

The present invention relates to a resin containing a specific structure. More specifically, this invention relates to a resin suited for applications such as a surface protective film or interlayer insulating film of an electronic component or circuit board, a solder resist for a circuit board, an insulating layer of an organic electroluminescent element, a flattening film of a driving thin film transistor substrate of a display device using an organic electroluminescent element, an interlayer insulating film of a thin film transistor, an on-chip microlens of a solid-state image pickup element, various displays, and a flattening film for a solid state image pickup device, and a photosensitive resin composition using the resin.

This invention further relates to 5,5'-dihydroxyl-4,4'-diaminobiphenyl derivatives which can be used for these resins, resin compositions and pharmaceutical intermediates, a process for producing the same, and a method for synthesizing dibromobiphenyl derivatives used therein.

BACKGROUND ART

Resins having excellent insulating characteristics and made of organic polymers are applied to a flattening film of a driving thin film transistor substrate of a display device using a surface protective film or an interlayer insulating film of an electronic part or circuit board, an insulating layer of an organic electroluminescent element, and the organic electroluminescent element. Polyimide resins and polybenzoxazole resins which are particularly excellent in heat resistance, chemical resistance, mechanical properties and the like have been widely used.

In recent years, with the miniaturization and thinning of a device, deterioration of the process yield due to warpage of a device substrate and adverse effect on the reliability of the device are concerned. For this reason, it is also required to impart resins with the property of reducing the warpage of the substrate.

Examples of a method for reducing the warpage of the device substrate include a method of reducing a difference in coefficient of linear thermal expansion between a resin film-formed on the substrate and the substrate itself to reduce stress produced by a difference in thermal expansion. Since the linear thermal expansion coefficient of ordinary resins is larger by 10 ppm or more than the linear thermal expansion coefficient of a substrate, it is effective to reduce the linear thermal expansion coefficient of the resin in order to reduce the stress. In order to attain this object, polyimide resins including a rigid structure in the main chain and having a small linear thermal expansion coefficient (see, for example, Patent Documents 1 to 6), polyimide-polybenzoxazole resins (see, for example, Patent Document 7) and the like have been reported.

In a resin film formed using the resin, it is necessary to form a pattern such as a through hole in an opening of an electrode portion or the like. In the prior art, a pattern has been formed by forming a positive type photoresist film or the like on a resin film having no photosensitivity and etching the film. However, with this method, it is difficult to miniaturize the pattern due to high density and high speed and large capacity of a device, and therefore, resins having photosensitivity have been studied.

For example, regarding a positive type photosensitive resin composition, a composition containing a polyamide acid ester containing a phenolic hydroxyl group and an o-quinonediazide compound (see, for example, Patent Document 8), a composition containing a solvent-soluble ring-closing-type polyimide and naphthoquinonediazide compound (see, for example, Patent Document 9), and a composition containing a polybenzoxazole precursor and a naphthoquinonediazide compound (see, for example, Patent Document 10) have been reported. Regarding a negative type photosensitive resin composition, a polyimide precursor in which an acrylic compound is bonded to a side chain (see, for example, Patent Document 11) and a mixture of polyimide with an acrylic compound (see, for example, Patent Document 12) have been reported.

In addition, monomers for synthesizing these polyimides have a very important role in the performance of a polyimide polymer. A monomer of polyimide mainly has two kinds of monomers including a diamine monomer and a diacid anhydride monomer. When structures of the two kinds of monomers are changed, it is possible to remarkably improve the performance in each field of polyimide, such as the coefficient of thermal expansion, light transmittance, or elastic modulus. As a result of study, it is disclosed that introducing a hydroxyl group into a monomer can remarkably change the coefficient of thermal expansion, light transmittance or modulus of elasticity of polyimide (see, for example, Non-Patent Document 1). In an industrial production process, in order to reduce the cost of a polymer monomer, it is very important to obtain a low-cost hydroxyl group-containing diamine monomer. On the other hand, 4,4'-diaminobiphenyl derivative monomers have already been widely used for the synthesis of polyimides, and the cost is very low (see, for example, Patent Documents 13 and 14).

A dibromobiphenyl derivative used for this is a commonly used chemical raw material, pharmaceutical intermediate, or electronic material. At the same time, since a bromine group in a dibromobiphenyl compound can be further converted into a hydroxyl group, an amino group, a cyano group, an alkoxy group, a double bond, a triple bond, an organometallic compound, or etc., the bromine group finds very wide application in the fields of refinement, polymer intermediates, and the like. Commonly used methods for synthesizing dibromobiphenyl derivatives are as follows. That is, a biphenyl compound is used as a raw material, and a dibromobiphenyl derivative can be obtained under the action of a bromination reagent. However, there is a possibility that a plurality of positions on a benzene ring of a biphenyl derivative are substituted with bromine, and selectivity is poor, so that the yield of reaction is low. In order to solve this problem, a bromination reaction using liquid bromine and protic solvent ethanol alone is disclosed (see, for example, Patent Document 15). It is also disclosed to promote the reaction by using liquid bromine as a bromination reagent and acetic acid as a solvent and adding sodium acetate (see, for example, Non-Patent Document 2).

PRIOR ART DOCUMENTS

Patent Documents

Patent Document 1: Japanese Patent Laid-open Publication No. H2-283762

Patent Document 2: Japanese Patent Laid-open Publication No. H8-48773
Patent Document 3: Japanese Patent Laid-open Publication No. H8-253584
Patent Document 4: Japanese Patent Laid-open Publication No. H11-158279
Patent Document 5: Japanese Patent Laid-open Publication No. 2002-363283
Patent Document 6: Japanese Patent Laid-open Publication No. 2003-212996
Patent Document 7: Japanese Patent Laid-open Publication No. 2007-177117
Patent Document 8: Japanese Patent Laid-open Publication No. H4-204945
Patent Document 9: Japanese Patent Laid-open Publication No. H3-209478
Patent Document 10: International Publication No. WO10/092824
Patent Document 11: Japanese Patent Laid-open Publication No. 2011-191749
Patent Document 12: International Publication No. WO04/109403
Patent Document 13: Japanese Patent Laid-open Publication No. 2007-106859
Patent Document 14: U.S. Pat. No. 5,378,420
Patent Document 15: Chinese Patent Application Publication No. 200780002686.6

Non-Patent Documents

Non-Patent Document 1: Progress in Polymer Science (2012), 37(7), 907-974
Non-Patent Document 2: Synthesis, 2000, 383-388

SUMMARY OF THE INVENTION

Problems to be Solved by the Invention

However, in the above resin having a small linear thermal expansion coefficient, there is a problem that due to the rigid skeleton introduced into the main chain, the absorbance, particularly the absorbance of an i-line (light having a wavelength of 365 nm) currently widely used for pattern processing a photosensitive resin, is high, and it is difficult to impart good photosensitive characteristics due to energy loss caused by absorption of the resin itself.

A further object is to produce, as a monomer for synthesizing polyimide, a low-cost hydroxyl group-containing diamine monomer in which a hydroxyl group is introduced into a 4,4'-diaminobiphenyl derivative monomer.

Further, regarding a dibromobiphenyl derivative used for this, the yield is very low according to the method disclosed in Patent Document 15, and there is a problem that it is not suitable for mass production. Furthermore, according to the method disclosed in Non-Patent Document 2, the degree of corrosion to equipment is relatively large due to use of acidic solvent and salt, recovery of solvent is difficult, difficulty in post-treatment is increased, and there is a problem of environmental pollution.

In view of the above-described problems of the prior art, an object of the present invention is to provide a resin having a small linear thermal expansion coefficient and a low absorbance.

A further object is to provide a production process including highly selectively introducing a bromine atom into a 5,5'-dihydroxyl-4,4'-diaminobiphenyl derivative used in these resins and a 5,5' position, at the same time, simplifying a process for post-treating a bromination reaction, obtaining a 5,5'-dibromo-4,4'-diaminobiphenyl derivative, and then converting the bromine atom into a hydroxyl group by a reaction of an oxazole ring and a ring opening reaction. A furthermore object is to provide a method for synthesizing dibromobiphenyl derivatives used for this, easily achieving high yield, low cost, and mass production, and hardly polluting the environment.

Solutions to the Problems

As a result of intensive studies to solve the above problems, the inventors have found the present invention. That is, the present invention is a resin characterized by including at least one structure selected from the structures represented by the following general formulae (1) and (2).

[Chemical Formula 1]

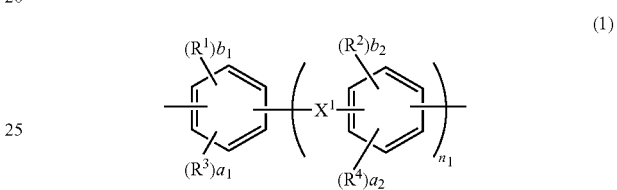

(1)

(The general formula (1) is a divalent organic group, and $R^1$ and $R^2$ each independently represent a halogen atom or a monovalent organic group having 1 to 3 carbon atoms. $R^3$ and $R^4$ each represent an organic group selected from a hydroxyl group, a carboxyl group and a sulfonic acid group. $X^1$ is a single bond, O, S, NH, $SO_2$, CO or a divalent organic group having 1 to 3 carbon atoms or a divalent crosslinked structure formed by linking two or more of them. $n_1$ is 0 or 1. When $n_1=0$, $a_1$ is an integer of 1 to 3, $b_1$ is an integer of 1 to 3, and $a_1+b_1$ is an integer of 2 to 4. When $n_1=1$, $a_1$ is an integer of 1 to 4, $b_1$ is an integer of 0 to 3, $a_2$ is an integer of 0 to 4, $b_2$ is an integer of 0 to 4, $a_1+b_1$ is an integer of 1 to 4, $a_2+b_2$ is an integer of 0 to 4, and at least one of $b_1$ and $b_2$ is an integer of 1 or more.)

[Chemical Formula 2]

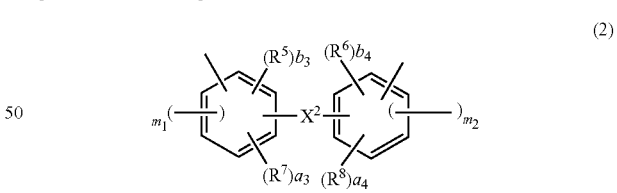

(2)

(The general formula (2) is a trivalent or tetravalent organic group, and $R^5$ and $R^6$ each independently represent a halogen atom or a monovalent organic group having 1 to 3 carbon atoms. $R^7$ and $R^8$ each represent an organic group selected from a hydroxyl group, a carboxyl group and a sulfonic acid group. $X^2$ is a single bond, O, S, NH, $SO_2$, CO or a divalent organic group having 1 to 3 carbon atoms or a divalent crosslinked structure formed by linking two or more of these. $a_3$, $a_4$, $b_3$ and $b_4$ are integers of 0 to 3, $a_3+b_3$ is an integer of 0 to 3, $a_4+b_4$ is an integer of 0 to 3, at least one of $a_3$ and $a_4$ is an integer of 1 or more, and at least one of $b_3$ and $b_4$ is an integer of 1 or more. $m_1$ and $m_2$ are integers of 0 or 1, and $m_1+m_2$ is an integer of 1 or 2.)

Effects of the Invention

According to the present invention, it is possible to obtain a resin having a low linear thermal expansion coefficient and a low absorbance.

EMBODIMENTS OF THE INVENTION

Figure 1:
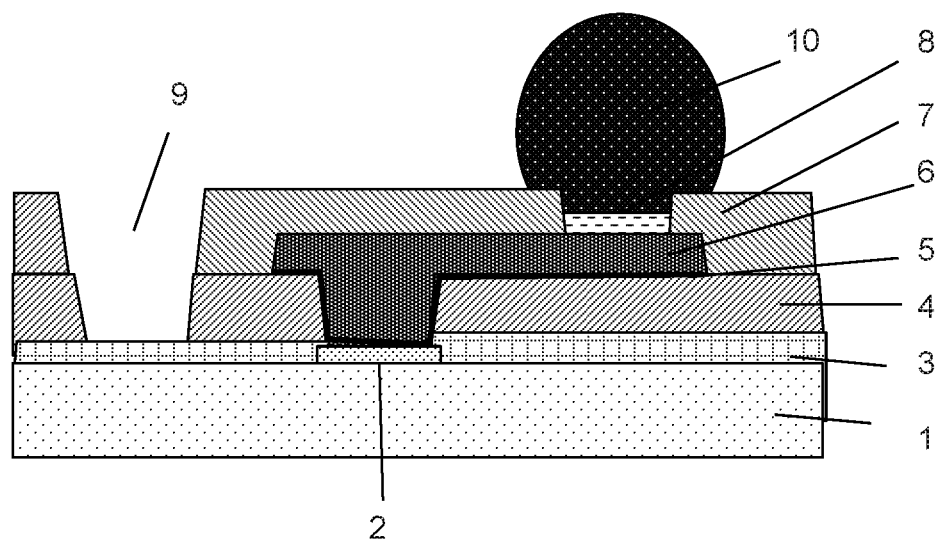
FIG. 1 is an enlarged cross-sectional view of a pad portion of a semiconductor device having a bump.

The present invention is a resin characterized by including at least one structure selected from the structures represented by the following general formulae (1) and (2).

[Chemical Formula 3]

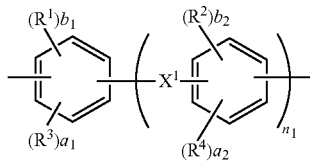

(1)

(The general formula (1) is a divalent organic group, and $R^1$ and $R^2$ each independently represent a halogen atom or a monovalent organic group having 1 to 3 carbon atoms. $R^3$ and $R^4$ each represent an organic group selected from a hydroxyl group, a carboxyl group and a sulfonic acid group. $X^1$ is a single bond, O, S, NH, $SO_2$, CO or a divalent organic group having 1 to 3 carbon atoms or a divalent crosslinked structure formed by linking two or more of them. $n_1$ is 0 or 1. When $n_1=0$, $a_1$ is an integer of 1 to 3, $b_1$ is an integer of 1 to 3, and $a_1+b_1$ is an integer of 2 to 4. When $n_1=1$, $a_1$ is an integer of 1 to 4, $b_1$ is an integer of 0 to 3, $a_2$ is an integer of 0 to 4, $b_2$ is an integer of 0 to 4, $a_1+b_1$ is an integer of 1 to 4, $a_2+b_2$ is an integer of 0 to 4, and at least one of $b_1$ and $b_2$ is an integer of 1 or more.)

[Chemical Formula 4]

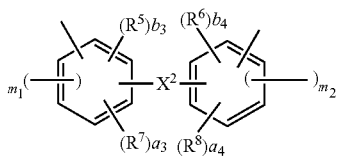

(2)

(The general formula (2) is a trivalent or tetravalent organic group, and $R^5$ and $R^6$ each independently represent a halogen atom or a monovalent organic group having 1 to 3 carbon atoms. $R^7$ and $R^8$ each represent an organic group selected from a hydroxyl group, a carboxyl group and a sulfonic acid group. $X^2$ is a single bond, O, S, NH, $SO_2$, CO or a divalent organic group having 1 to 3 carbon atoms or a divalent crosslinked structure formed by linking two or more of these, $a_3$, $a_4$, $b_3$ and $b_4$ are integers of 0 to 3, $a_3+b_3$ is an integer of 0 to 3, $a_4+b_4$ is an integer of 0 to 3, at least one of $a_3$ and $a_4$ is an integer of 1 or more, and at least one of $b_3$ and $b_4$ is an integer of 1 or more. $m_1$ and $m_2$ are integers of 0 or 1, and $m_1+m_2$ is an integer of 1 or 2.)

The general formula (1) is a divalent organic group, and $R^1$ and $R^2$ each independently represent a halogen atom or a monovalent organic group having 1 to 3 carbon atoms. From the viewpoint of heat resistance of the resultant resin, preferred specific examples include a methyl group, a methoxy group, an ethyl group, an ethoxy group, a fluoro group, a trifluoromethyl group, a pentafluoroethyl group, a trifluoromethoxy group, and a pentafluoroethoxy group, but the present invention is not limited thereto. Further, from the viewpoint that absorbance of the resultant resin can be reduced, a fluoro group, a trifluoromethyl group, a pentafluoroethyl group, a trifluoromethoxy group and a pentafluoroethoxy group are more preferable, and a trifluoromethyl group and a pentafluoroethyl group are most preferable. Further, from the viewpoint that the absorbance of the resultant resin can be reduced, $R^1$ and $R^2$ are preferably in the ortho position relative to a polymer chain. Furthermore, from the viewpoint that a linear thermal expansion coefficient of the resultant resin can be reduced, $R^1$ and $R^2$ are more preferably bonded to positions 2 and 2'.

$R^3$ and $R^4$ each represent an organic group selected from a hydroxyl group, a carboxyl group and a sulfonic acid group. The organic group is preferably a hydroxyl group. From the viewpoint that the absorbance of the resultant resin can be reduced, $R^3$ and $R^4$ are preferably in the ortho position relative to a polymer chain. $X^1$ is a single bond, O, S, NH, $SO_2$, CO or a divalent organic group having 1 to 3 carbon atoms or a divalent crosslinked structure formed by linking two or more of them. From the viewpoint that the linear thermal expansion coefficient of the resultant resin can be reduced, $X^1$ is preferably a single bond.

$n_1$ is 0 or 1. From the viewpoint that the absorbance of the resultant resin can be reduced, $n_1$ is preferably 1. When $n_1=0$, $a_1$ is an integer of 1 to 3, $b_1$ is an integer of 1 to 3, and $a_1+b_1$ is an integer of 2 to 4. When $n_1=1$, $a_1$ is an integer of 1 to 4, $b_1$ is an integer of 0 to 3, $a_2$ is an integer of 0 to 4, $b_2$ is an integer of 0 to 4, $a_1+b_1$ is an integer of 1 to 4, $a_2+b_2$ is an integer of 0 to 4, and at least one of $b_1$ and $b_2$ is an integer of 1 or more. From the viewpoint that the linear thermal expansion coefficient of the resultant resin can be reduced, when $n_1=0$, it is preferable that $a_1$ and $b_1$ are 1 or 2, and it is more preferable that $a_1=b_1=2$. Similarly, from the viewpoint that the linear thermal expansion coefficient of the resultant resin can be reduced, when $n_1=1$, it is preferable that $a_1=a_2=1$ and $b_1$ and $b_2$ are 1 or 2, and it is more preferable that $a_1=a_2=b_1=b_2=1$. Further, from the viewpoint that the linear thermal expansion coefficient of the resultant resin can be reduced, it is preferable that all aromatic rings having a structure represented by the general formula (1) are bonded to a polymer main chain at the para positions.

In the present invention, examples of preferred structures represented by the general formula (1) include the following structures, but the structures are not limited thereto.

[Chemical Formula 5]
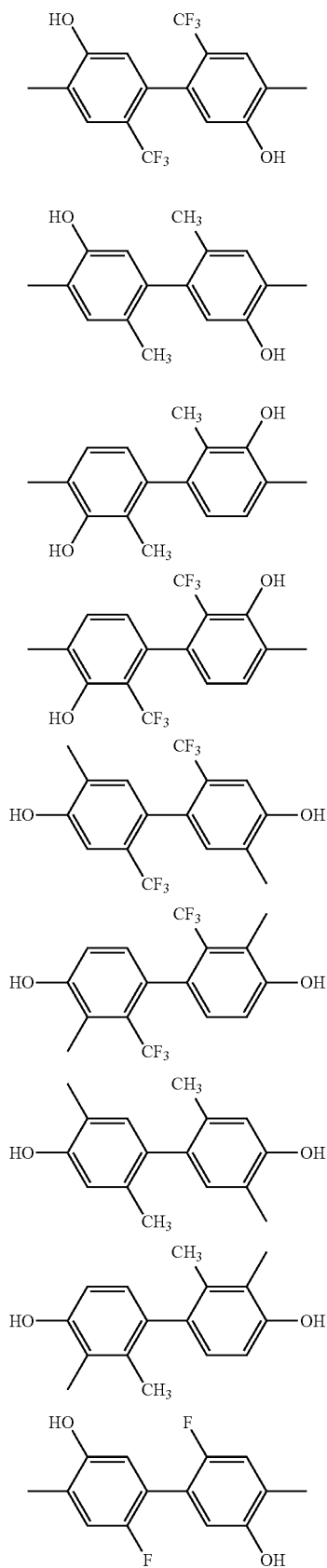
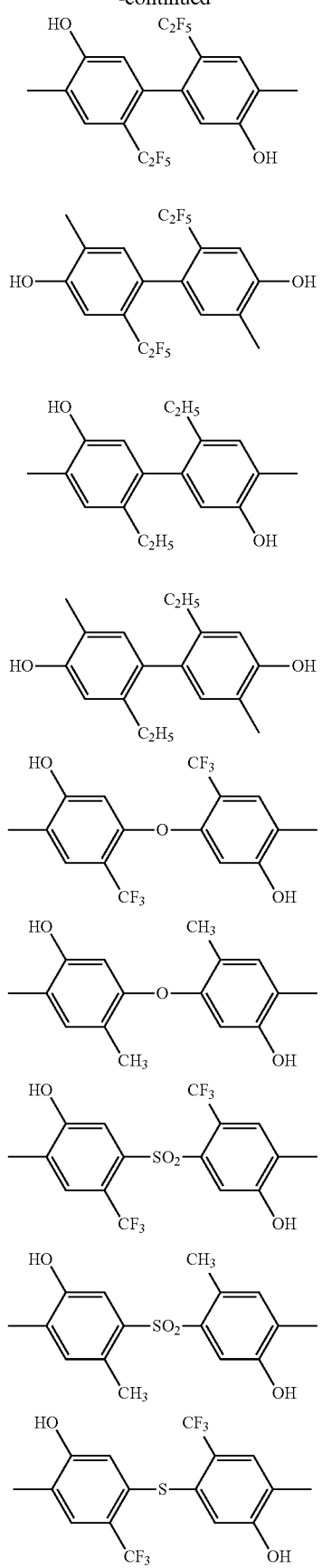

-continued
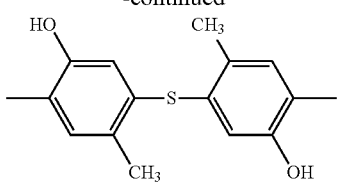
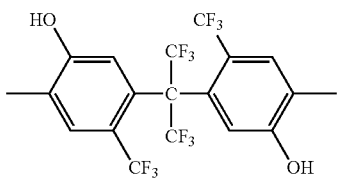
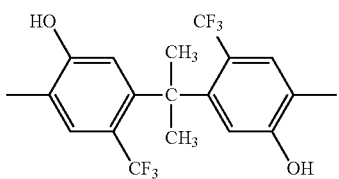
[Chemical Formula 6]
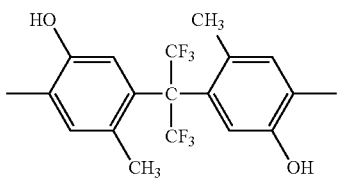
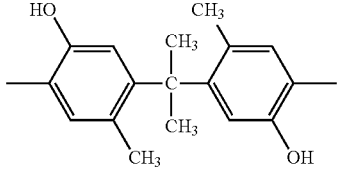
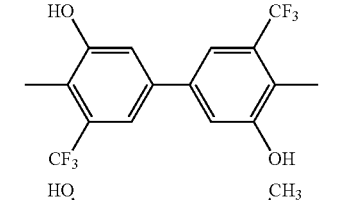
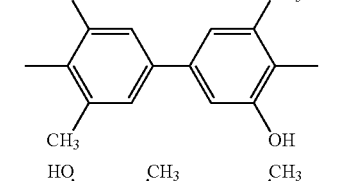
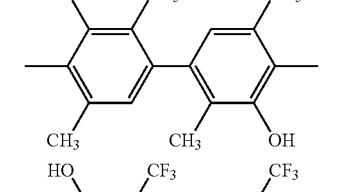
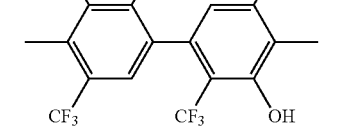
-continued
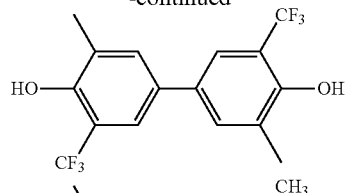
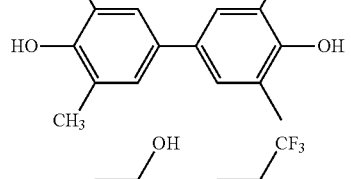
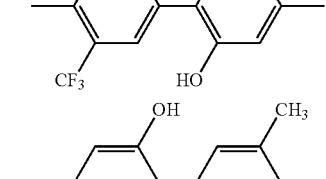
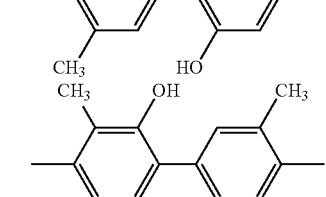
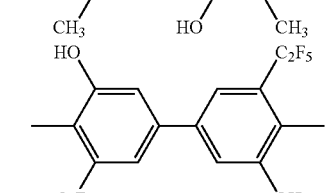
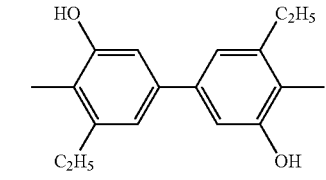
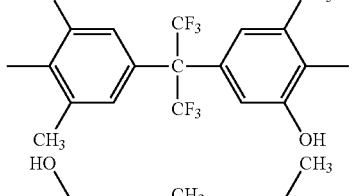
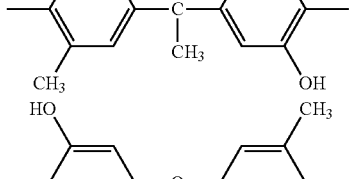

-continued

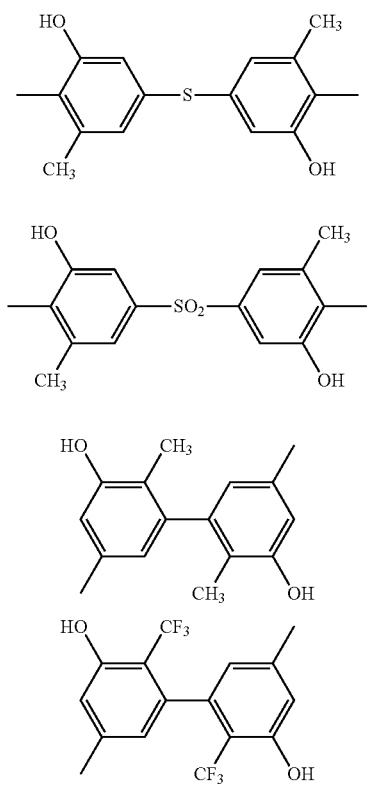

[Chemical Formula 7]

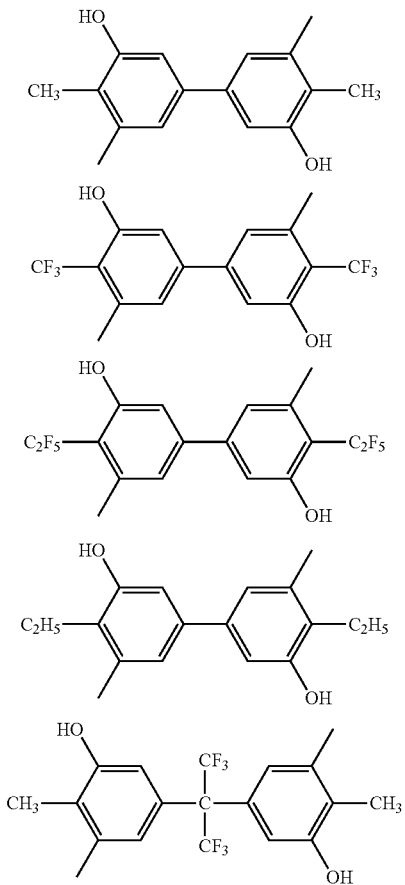

-continued

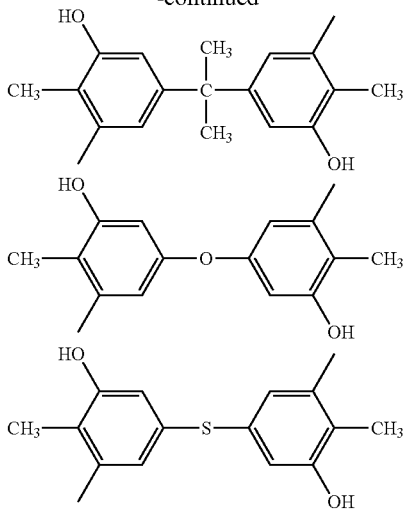

In the general formula (2), $R^5$ and $R^6$ each independently represent a halogen atom or a monovalent organic group having 1 to 3 carbon atoms. From the viewpoint of the heat resistance of the resultant resin, preferred specific examples include a methyl group, a methoxy group, an ethyl group, an ethoxy group, a fluoro group, a trifluoromethyl group, a pentafluoroethyl group, a trifluoromethoxy group, and a pentafluoroethoxy group, but the present invention is not limited thereto. Further, from the viewpoint that absorbance of the resultant resin can be reduced, a fluoro group, a trifluoromethyl group, a pentafluoroethyl group, a trifluoromethoxy group and a pentafluoroethoxy group are more preferable, and a trifluoromethyl group and a pentafluoroethyl group are most preferable.

Further, from the viewpoint that the absorbance of the resultant resin can be reduced, $R^5$ and $R^6$ are preferably in the ortho position relative to the polymer chain. Furthermore, from the viewpoint that the linear thermal expansion coefficient of the resultant resin can be reduced, $R^5$ and $R^6$ are more preferably bonded to positions 2 and 2'. $R^7$ and $R^8$ each represent an organic group selected from a hydroxyl group, a carboxyl group and a sulfonic acid group. The organic group is preferably a hydroxyl group. From the viewpoint that the absorbance of the resultant resin can be reduced, $R^7$ and $R^8$ are preferably in the ortho position relative to the polymer chain. $X^2$ is a single bond, O, S, NH, $SO_2$, CO or a divalent organic group having 1 to 3 carbon atoms or a divalent crosslinked structure formed by linking two or more of these. From the viewpoint that the linear thermal expansion coefficient of the resultant resin can be reduced, $X^1$ is preferably a single bond.

$a_3$, $a_4$, $b_3$ and $b_4$ are integers of 0 to 3, $a_3+b_3$ is an integer of 0 to 3, $a_4+b_4$ is an integer of 0 to 3, at least one of $a_3$ and $a_4$ is an integer of 1 or more, and at least one of $b_3$ and $b_4$ is an integer of 1 or more. From the viewpoint that the linear thermal expansion coefficient of the resultant resin can be reduced, it is preferable that $a_3=a_4=1$ and $b_3$ and $b_4$ are 1 or 2, and it is more preferable that $a_3=a_4=b_3=b_4=1$. $m_1$ and $m_2$ are integers of 0 or 1, and $m_1+m_2$ is an integer of 1 or 2. Preferably, $m_1=m_2=1$.

In the present invention, examples of preferred structures represented by the general formula (2) include the following structures.

[Chemical Formula 8]
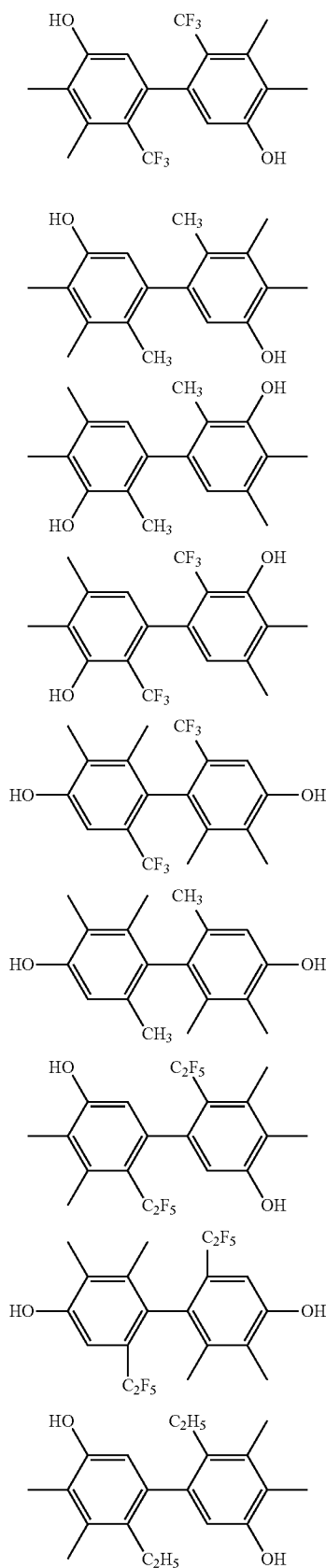
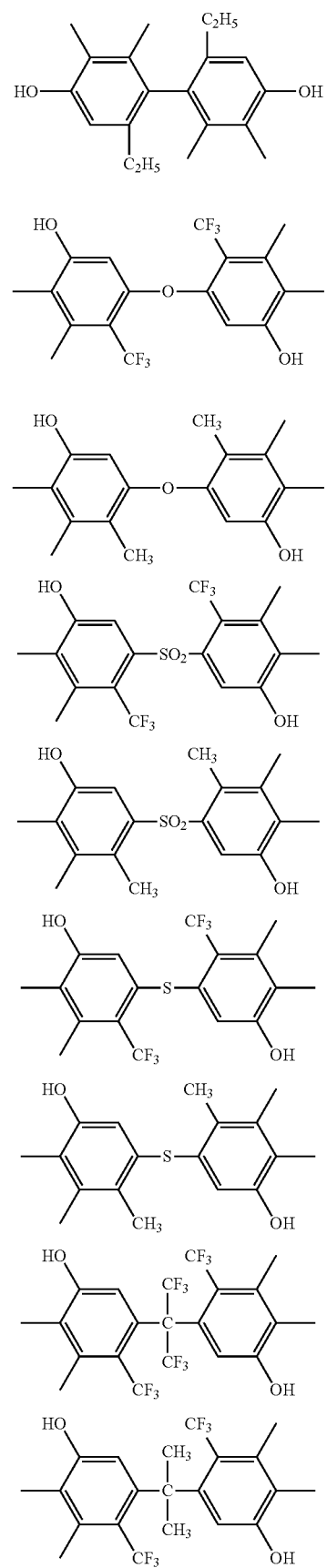

15
-continued

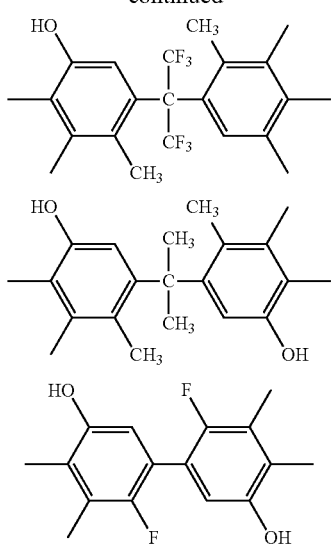

[Chemical Formula 9]

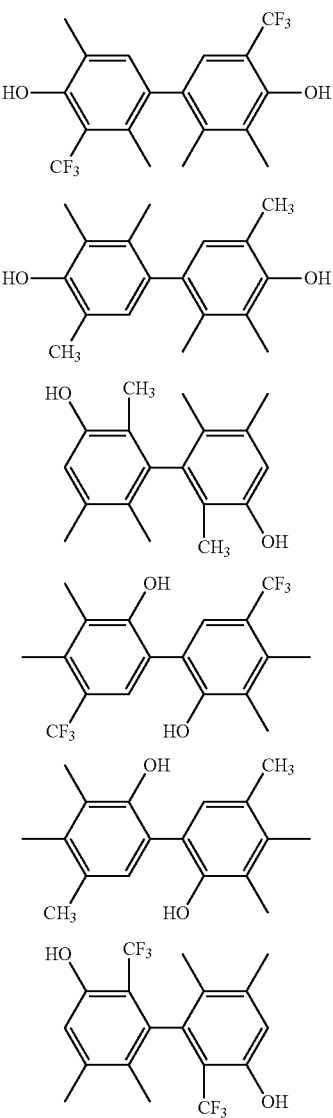

16
-continued

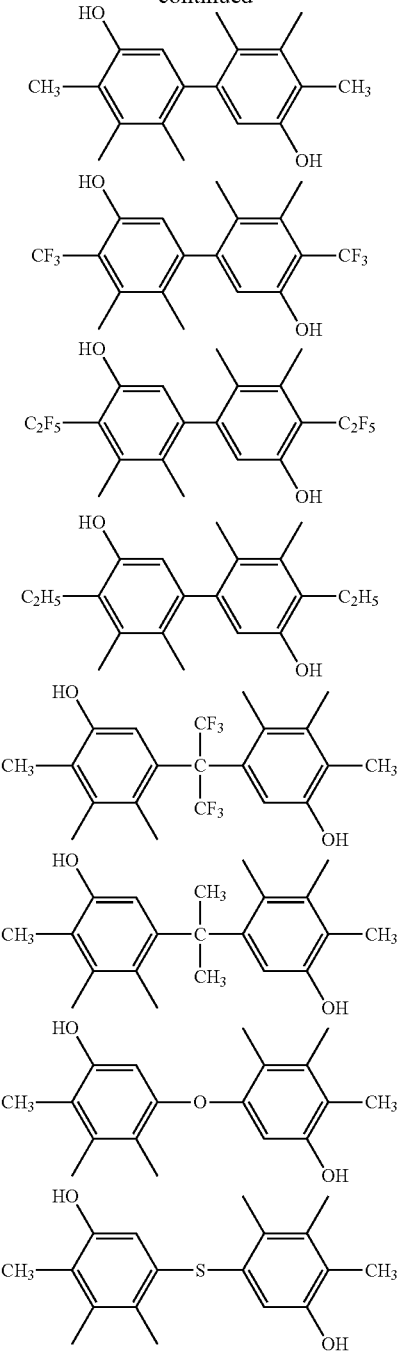

Examples of the resin having at least one structure selected from the structures represented by the general formulae (1) and (2) include, but are not limited to, polyurethane, polyurea, polyester, polycarbonate, polyamine, polyazomethine, polyamide, polyamideimide, polyamide-imide precursor, polyimide, polyimide precursor, polybenzoxazole, polybenzoxazole precursor, polybenzothiazole, polybenzothiazole precursor, polybenzimidazole, polybenzimidazole precursor, polyether ketone, polyphenylene oxide, polyphenylene sulfide, polyether ether ketone, polyethersulfone, random copolymers thereof, and block copolymers thereof. From the viewpoints of heat resistance, chemical resistance and mechanical properties of a film obtained after heat treatment, the resin is preferably at least one selected from polyimide, polyamideimide, polybenzoxazole, polyimide precursor, polyamideimide precursor, polybenzoxazole precursor, random copolymers thereof, and block copolymers thereof. From the viewpoint that a heat treatment temperature can be lowered, polyimide and polyamideimide are more preferable, and from the viewpoint of heat resistance, polyimide is most preferable.

Such a resin can be synthesized, for example, by reacting dicarboxylic acid, tricarboxylic acid, tetracarboxylic acid or a derivative or anhydride thereof with diamine, diisocyanate, or a compound obtained by substituting these with a hydroxyl group or a carboxyl group or a derivative thereof, at a temperature in a range of −30° C. to 300° C. For example, a polyimide precursor or polyimide can be obtained by reacting tetracarboxylic acid, a tetracarboxylic acid derivative or tetracarboxylic dianhydride with diamine. A polyamide-imide precursor or polyamide-imide can be obtained by reacting tricarboxylic acid, a tricarboxylic acid derivative or a tricarboxylic anhydride with diamine. A polybenzoxazole precursor and polybenzoxazole can be obtained by reacting bisaminophenol with a dicarboxylic acid derivative such as dicarboxylic acid or hydroxybenzotriazole ester thereof and an imidazolide compound thereof.

The kind of a polymerization solvent is not particularly limited as long as it can dissolve a produced resin. Examples of the polymerization solvent include polar aprotic solvents such as N-methyl-2-pyrrolidone, γ-butyrolactone, N, N-dimethylformamide, N, N-dimethylacetamide, 1,3-dimethyl-2-imidazolidinone, and dimethylsulfoxide; glycol ethers such as tetrahydrofuran, dioxane, propylene glycol monomethyl ether, propyleneglycolmonoethylether, diethyleneglycoldimethylether, diethyleneglycoldiethylether, and diethyleneglycolethylmethylether; ketones such as acetone, methyl ethyl ketone, diisobutyl ketone, and diacetone alcohol; esters such as ethyl acetate, butyl acetate, isobutyl acetate, propyl acetate, propylene glycol monomethyl ether acetate, glycol ether acetate, and 3-methyl-3-methoxybutylacetate; alcohols such as ethyl lactate, methyl lactate, diacetone alcohol, and 3-methyl-3-methoxybutanol; and aromatic hydrocarbons such as toluene and xylene. Two or more of those polymerization solvents may be contained. The polymerization solvent is preferably used in an amount of from 100 to 1900 parts by weight, more preferably from 150 to 950 parts by weight, based on 100 parts by weight of the resultant resin. When the amount of the polymerization solvent is within this range, the solution after polymerization has an easily handled viscosity.

Examples of the specific structure of the resin in the present invention include the resins listed in the following general formulae (3) to (5).

[Chemical Formula 10]

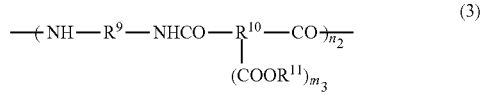

(3)

(In the general formula (3), $R^9$ represents a divalent organic group having 2 to 50 carbon atoms. $R^{10}$ represents a trivalent or tetravalent organic group having 2 to 50 carbon atoms. $R^9$ represents a structure selected from the general formula (1) or the following general formula (6), and/or $R^1$ represents a structure selected from the general formula (2) or the following general formula (7). $R^{11}$ represents hydrogen or an organic group having 1 to 10 carbon atoms. $m_3$ represents an integer of 1 or 2. $n_2$ represents a range of 10 to 100,000.)

[Chemical Formula 11]

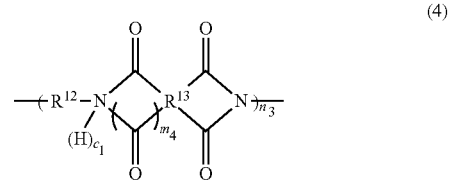

(4)

(In the general formula (4), $R^{12}$ represents a divalent organic group having 2 to 50 carbon atoms. $R^{13}$ represents a trivalent or tetravalent organic group having 2 to 50 carbon atoms. $R^{12}$ represents a structure selected from the general formula (1) or the following general formula (6), and/or $R^{13}$ represents a structure selected from the general formula (2) or the following general formula (7). $m_4$ is an integer of 0 or 1, $c_1$ is an integer of 0 or 1, $c_1=1$ when $m_4=0$, and $c_1=0$ when $m_4=1$. $n_3$ represents a range of 10 to 100,000.)

[Chemical Formula 12]

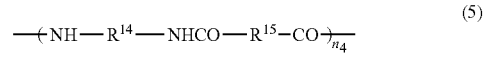

(5)

(In the above general formula (5), $R^{14}$ and $R^{15}$ each represent a tetravalent organic group having 2 to 50 carbon atoms, $R^{14}$ and/or $R^{15}$ represents a structure selected from the general formula (1) or the following general formula (6). $n_4$ represents a range of 10 to 100,000.)

[Chemical Formula 13]

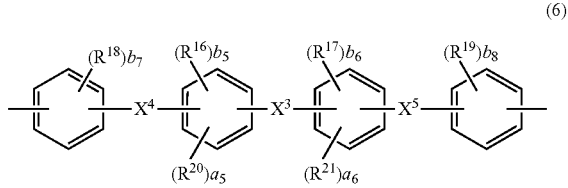

(6)

(The general formula (6) is a divalent organic group, and $R^{16}$ to $R^{19}$ each independently represent a halogen atom or a monovalent organic group having 1 to 3 carbon atoms. $R^{20}$ and $R^{21}$ each represent an organic group selected from a hydroxyl group, a carboxyl group, and a sulfonic acid group. $X^3$ is a single bond, O, S, NH, $SO_2$, CO or a divalent organic group having 1 to 3 carbon atoms or a divalent crosslinked structure formed by linking two or more of these. $X^4$ and $X^5$ each represent a structure selected from an amide bond and an azomethine bond. $a_5$ is an integer of 1 to 4, $b_5$ is an integer of 0 to 3, $a_6$ is an integer of 0 to 4, $b_6$ is an integer of 0 to 4, $b_7$ and $b_8$ are integers of 0 to 4, as $+b_5$ is an integer of 1 to 4, $a_6+b_6$ is an integer of 0 to 4, and at least one of $b_5$ and $b_6$ is an integer of 1 or more.)

[Chemical Formula 14]

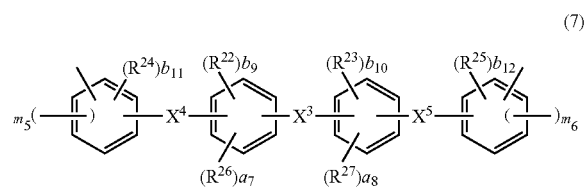

(7)

(The general formula (7) is a trivalent or tetravalent organic group, and $R^{22}$ to $R^{25}$ each independently represent a halogen atom or a monovalent organic group having 1 to 3 carbon atoms. $R^{26}$ and $R^{27}$ each represent an organic group selected from a hydroxyl group, a carboxyl group, and a sulfonic acid group. $X^6$ is a single bond, O, S, NH, $SO_2$, CO or a divalent organic group having 1 to 3 carbon atoms or a divalent crosslinked structure formed by linking two or more of these. $X^7$ and $X^8$ each represent a structure selected from an amide bond and an azomethine bond. $a_7$ is an integer of 1 to 4, $b_9$ is an integer of 0 to 3, $a_8$ is an integer of 0 to 4, $b_{10}$ is an integer of 0 to 4, $b_{11}$ and $b_{12}$ are integers of 0 to 3, $a_7+b_9$ is an integer of 1 to 4, $a_8+b_{10}$ is an integer of 0 to 4, and at least one of $b_9$ and $b_{10}$ is an integer of 1 or more. $m_5$ and $m_6$ are integers of 0 or 1, and $m_5+m_6$ is an integer of 1 or 2.)

In the general formulae (3), (4) and (5), $R^9$, $R^{12}$ and $R^{14}$ each represent a residue of diamine, silylated diamine, or diisocyanate and represent a divalent organic group having 2 to 50 carbon atoms. Among them, an organic group containing an aromatic ring or a cyclic aliphatic group and having 5 to 40 carbon atoms is preferable. Preferred specific examples include bis(3-amino-4-hydroxyphenyl)hexafluoropropane, bis(3-amino-4-hydroxyphenyl)sulfone, bis(3-amino-4-hydroxyphenyl)propane, bis(3-amino-4-hydroxyphenyl)methylene, bis(3-amino-4-hydroxyphenyl)ether, bis(3-amino-4-hydroxy)biphenyl, bis(3-amino-4-hydroxyphenyl)fluorene, 3,5-diaminobenzoic acid, 3-carboxy-4,4'-diaminodiphenyl ether, 3-sulfonic acid-4,4'-diaminodiphenyl ether, dithiohydroxyphenylenediamine, 3,4'-diaminodiphenyl ether, 4,4'-diamino diphenyl ether, 3,4'-diaminodiphenylmethane, 4,4'-diaminodiphenylmethane, 3,4'-diaminodiphenylsulfone, 4,4'-diaminodiphenylsulfone, 3,4'-diaminodiphenylsulfide, 4,4'-diaminodiphenylsulfide, 1,4-bis (4-aminophenoxy)benzene, 1,3-bis (4-aminophenoxy)benzene, benzidine, m-phenylenediamine, p-phenylenediamine, 1,5-naphthalenediamine, 2,6-naphthalenediamine, bis(4-aminophenoxyphenyl)sulfone, bis(3-aminophenoxyphenyl)sulfone, bis(4-aminophenoxy) biphenyl, bis{4-(4-aminophenoxy)phenyl}ether, 2,2'-dimethyl-4,4'-diaminobiphenyl, 2,2'-diethyl-4,4'-diaminobiphenyl, 3,3'-dimethyl-4,4'-diaminobiphenyl, 3,3'-diethyl-4,4'-diaminobiphenyl, 2,2',3,3'-tetramethyl-4,4'-diaminobiphenyl, 3,3',4,4'-tetramethyl-4,4'-diaminobiphenyl, 2,2'-di(trifluoromethyl)-4,4'-diaminobiphenyl, a residue of 9,9-bis(4-aminophenyl)fluorene, residues of compounds in which aromatic rings of these compounds are substituted with alkyl groups or halogen atoms, residues of hydrogenated products of these compounds, and the structures represented by the general formulae (1) and (6). These may be used alone or in combination of two or more.

In the general formulae (3) and (4), $R^{10}$ and $R^{13}$ each represent a residue of tetracarboxylic acid, tricarboxylic acid, tetracarboxylic acid dianhydride or tricarboxylic acid anhydride, and a trivalent or tetravalent organic group having 2 to 50 carbon atoms. Among them, an organic group containing an aromatic ring or a cyclic aliphatic group and having 5 to 40 carbon atoms is preferable. Preferred specific examples include pyromellitic anhydride, 3,3',4,4'-biphenyltetracarboxylic dianhydride, 2,3,3',4'-biphenyltetracarboxylic dianhydride, 2,2',3,3'-biphenyltetracarboxylic dianhydride, 3,3',4,4'-benzophenonetetracarboxylic dianhydride, 2,2',3,3'-benzophenonetetracarboxylic dianhydride, 2,2-bis(3,4-dicarboxyphenyl)propane dianhydride, 2,2-bis(2,3-dicarboxyphenyl)propane dianhydride, 1,1-bis(3,4-dicarboxyphenyl)ethane dianhydride, 1,1-bis(2,3-dicarboxyphenyl) ethane dianhydride, bis(3,4-dicarboxyphenyl)methane dianhydride, bis(2,3-dicarboxyphenyl)methane dianhydride, bis(3,4-dicarboxyphenyl)sulfone dianhydride, bis(3,4-dicarboxyphenyl)ether dianhydride, 2,2-bis(3,4-dicarboxyphenyl)hexafluoropropane dianhydride, 2,2-bis(2,3-dicarboxyphenyl)hexafluoropropane dianhydride, 9,9-bis(3,4-dicarboxyphenyl)fluorenic acid dianhydride, 9,9-bis{4-(3,4-dicarboxyphenoxy)phenyl}fluorenic acid dianhydride, 1,2,5,6-naphthalenetetracarboxylic dianhydride, 2,3,6,7-naphthalenetetracarboxylic dianhydride, 3,4,9,10-perylenetetracarboxylic dianhydride, 2,3,5,6-pyridinetetracarboxylic acid dianhydride, trimellitic anhydride, trimesic anhydride, diphenylethertricarboxylic acid anhydride, a residue of a biphenyltricarboxylic anhydride, a residue of a compound in which these aromatic rings are substituted with alkyl groups or halogen atoms, 1,2-dimethyl-1,2,3,4-cyclobutanetetracarboxylic acid dianhydride, 1,2,3,4-tetramethyl-1,2,3,4-cyclobutanetetracarboxylic dianhydride, 1,2,4,5-cyclohexane tetracarboxylic dianhydride, 3,4-dicarboxy-1,2,3,4-tetrahydro-1-naphthalene succinic dianhydride, 5-(2,5-dioxotetrahydrofuryl)-3-methyl-3-cyclohexene-1,2-dicarboxylic dianhydride, 2,3,5-tricarboxy-2-cyclopentane acetic acid dianhydride, bicyclo[2.2.2]oct-7-ene-2,3,5,6-tetracarboxylic dianhydride, 2,3,4,5-tetrahydrofuran tetracarboxylic dianhydride, a residue of 3,5,6-tricarboxy-2-norbornane acetic acid dianhydride, and structures represented by the general formulae (2) and (7). These may be used alone or in combination of two or more.

From the viewpoint that the linear thermal expansion coefficient of the resultant resin can be reduced, it is preferable that $R^{10}$ and $R^{13}$ contain residues derived from pyromellitic anhydride. Further, from the viewpoint that the absorbance can be reduced while reducing the linear thermal expansion coefficient, it is more preferable that the contained pyromellitic anhydride is 30 mol % to 80 mol % in acid anhydride.

In the general formula (5), $R^{15}$ represents a residue derived from dicarboxylic acid and represents a divalent organic group having 2 to 50 carbon atoms. Specific examples of preferred dicarboxylic acids include terephthalic acid, isophthalic acid, diphenyl ether dicarboxylic acid, naphthalene dicarboxylic acid, bis(carboxyphenyl)propane, bis(carboxyphenyl)hexafluoropropane, biphenyl dicarboxylic acid, benzophenonedicarboxylic acid, residues of aromatic dicarboxylic acids such as terphenydicarboxylic acid, residues of aliphatic dicarboxylic acids such as cyclohexanedicarboxylic acid, adipic acid, sebacic acid, and dodecanedioic acid, or residues of a compound in which these aromatic rings are substituted with alkyl groups or halogen atoms, and the structures represented by the general formulae (1) and (6). These may be used alone or in combination of two or more.

In the general formulae (3) and (4), it is preferable that $R^9$ and $R^{12}$ represent a structure selected from the general formulae (1) and (6), and/or $R^{10}$ and $R^{13}$ represent a structure selected from the general formulae (2) and (7).

In the general formula (5), at least one of $R^{14}$ and $R^{15}$ preferably represents the structure selected from the general formulae (1) and (6).

In the general formulae (3), (4) and (5), in order to improve adhesion between a heat resistance coating film after heat treatment and a silicon-based substrate or a glass substrate, or in order to increase resistance to oxygen plasma used for cleaning or UV ozone treatment, a siloxane structure may be copolymerized with $R^9$, $R^{10}$, $R^{12}$, $R^{13}$ and $R^{14}$ within a range not lowering heat resistance. Specific examples of $R^9$, $R^{12}$ and $R^{14}$ include residues of bis(3-aminopropyl)tetramethyldisiloxane, bis(p-amino-phenyl)octamethylpentasiloxane, and the like. These are preferably copolymerized in an amount of 1 mol % to 10 mol % relative to the whole of $R^9$, $R^{12}$ and $R^{14}$. Specific examples of $R^{10}$ and $R^{13}$ include residues of dimethylsilanediphthalic acid dianhydride, 1,3-bis(phthalic acid)tetramethyldisiloxane dianhydride, and the like. These may be used alone or in combination of two or more, and it is preferable that 1 mol % to 10 mol % relative to the whole of $R^{10}$ and $R^{13}$ is copolymerized.

In the general formulae (3), (4) and (5), in order to improve adhesion between a heat resistance coating film after heat treatment and a metal substrate, an aliphatic structure having a polyalkyleneoxide group may be copolymerized with $R^9$, $R^{12}$, and $R^{14}$ within a range not lowering heat resistance. Examples of specific structures include residues of Jeffamine (registered trademark) KH-511, Jeffamine ED-600, Jeffamine ED-900, Jeffamine ED-2003, Jeffamine EDR-148, Jeffamine EDR-176, Jeffamine D-200, Jeffamine D-400, Jeffamine D-2000, Jeffamine D-4000 (trade names, manufactured by HUNTSMAN Co., Ltd.), and the like. These may be used alone or in combination of two or more, and it is preferable that 1 mol % to 30 mol % relative to the whole of $R^9$, $R^{12}$, and $R^{14}$ is copolymerized.

In the general formula (3), $R^{11}$ represents hydrogen or an organic group having 1 to 10 carbon atoms. From the viewpoint of stability of the resultant photosensitive resin composition solution, $R^{11}$ is preferably an organic group, but hydrogen is preferable from the viewpoint of solubility of an alkaline aqueous solution. In the present invention, a hydrogen atom and an alkyl group can be mixed. By adjusting the amounts of hydrogen and an organic group in $R^{11}$, the dissolution rate in an alkaline aqueous solution is changed, so that a photosensitive resin composition having an appropriate dissolution rate can be obtained by this adjustment. In a preferable range, 10 mol % to 90 mol % of each $R^{11}$ is a hydrogen atom. If the carbon number of $R^{11}$ is 20 or less, a sufficient alkali solubility can be obtained. From the above, it is preferable that $R^{11}$ contains at least one hydrocarbon group having 1 to 20 carbon atoms, and the others are hydrogen atoms. Preferred examples of situations when $R^{11}$ is a hydrocarbon group include a methyl group, an ethyl group, a propyl group, and a butyl group. $m_3$ represents an integer of 1 or 2. $m_3$ is preferably 2.

In the general formula (4), $m_4$ is an integer of 0 or 1, $c_1$ is an integer of 0 or 1, $c_1=1$ when $m_4=0$, and $c_1=0$ when $m_4=1$. From the viewpoint that the linear thermal expansion coefficient of the resultant resin can be reduced, it is preferable that $m_4=1$ and $c_1=0$.

The general formula (6) is a divalent organic group, and $R^{16}$ to $R^{19}$ each independently represent a halogen atom or a monovalent organic group having 1 to 3 carbon atoms. From the viewpoint of the heat resistance of the resultant resin, preferred specific examples include, but are not limited to, a methyl group, a methoxy group, an ethyl group, an ethoxy group, a fluoro group, a trifluoromethyl group, a pentafluoroethyl group, a trifluoromethoxy group, and a pentafluoroethoxy group. Further, from the viewpoint that absorbance of the resultant resin can be reduced, a fluoro group, a trifluoromethyl group, a pentafluoroethyl group, a trifluoromethoxy group and a pentafluoroethoxy group are more preferable, and a trifluoromethyl group and a pentafluoroethyl group are most preferable. Further, from the viewpoint that the absorbance of the resultant resin can be reduced, $R^{16}$ to $R^{19}$ are preferably in the ortho position relative to the polymer chain. Furthermore, from the viewpoint that the linear thermal expansion coefficient of the resultant resin can be reduced, $R^{16}$ to $R^{19}$ are more preferably bonded to positions 2 and 2'.

$R^{20}$ and $R^{21}$ each represent an organic group selected from a hydroxyl group, a carboxyl group, and a sulfonic acid group. The organic group is preferably a hydroxyl group. Further, from the viewpoint that the absorbance of the resultant resin can be reduced, $R^{20}$ and $R^{21}$ are preferably in the ortho position relative to the polymer chain.

$X^3$ is a single bond, O, S, NH, $SO_2$, CO or a divalent organic group having 1 to 3 carbon atoms or a divalent crosslinked structure formed by linking two or more of these. From the viewpoint that the linear thermal expansion coefficient of the resultant resin can be reduced, $X^3$ is preferably a single bond. $X^4$ and $X^5$ each represent a structure selected from an amide bond and an azomethine bond. From the viewpoint that the absorbance of the resultant resin can be reduced, it is preferably an amide bond.

$a_5$ is an integer of 1 to 4, $b_5$ is an integer of 0 to 3, $a_6$ is an integer of 0 to 4, $b_6$ is an integer of 0 to 4, $b_7$ and $b_8$ are integers of 0 to 4, $a_5+b_5$ is an integer of 1 to 4, $a_6+b_6$ is an integer of 0 to 4, and at least one of $b_5$ and $b_6$ is an integer of 1 or more. From the viewpoint that the linear thermal expansion coefficient of the resultant resin can be reduced, it is preferable that $a_5=a_6=1$, $b_5$ and $b_6$ are 1 or 2, and $b_7$ and $b_8$ are 0 to 2, it is more preferable that $a_1=a_2=b_5=b_6=1$, and $b_7$ and $b_8$ are 0 to 2, and it is most preferable that $a_1=a_2=b_5=b_6=1$, and $b_7=b_8=0$. Further, from the viewpoint that the linear thermal expansion coefficient of the resultant resin can be reduced, it is preferable that all aromatic rings having a structure represented by the general formula (6) are bonded to a polymer main chain at the para positions.

In the present invention, examples of preferred structures represented by the general formula (6) include the following structures, but the structures are not limited thereto.

[Chemical Formula 15]

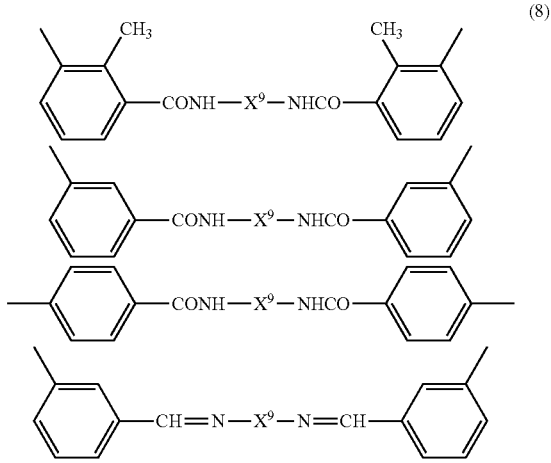

(8)

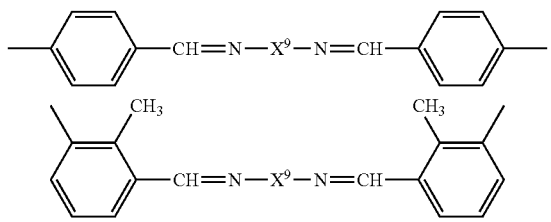

(In the general formula (8), $X^9$ represents a structure represented by [Chemical Formula 5] to [Chemical Formula 7].)

The general formula (7) is a trivalent or tetravalent organic group, and $R^{22}$ to $R^{25}$ each independently represent a halogen atom or a monovalent organic group having 1 to 3 carbon atoms. From the viewpoint of the heat resistance of the resultant resin, preferred specific examples include a methyl group, a methoxy group, an ethyl group, an ethoxy group, a fluoro group, a trifluoromethyl group, a pentafluoroethyl group, a trifluoromethoxy group, and a pentafluoroethoxy group, but the present invention is not limited thereto. Further, from the viewpoint that absorbance of the resultant resin can be reduced, a fluoro group, a trifluoromethyl group, a pentafluoroethyl group, a trifluoromethoxy group and a pentafluoroethoxy group are more preferable, and a trifluoromethyl group and a pentafluoroethyl group are most preferable. Further, from the viewpoint that the absorbance of the resultant resin can be reduced, $R^{22}$ to $R^{25}$ are preferably in the ortho position relative to the polymer chain. Furthermore, from the viewpoint that the linear thermal expansion coefficient of the resultant resin can be reduced, $R^{22}$ to $R^{25}$ are more preferably bonded to positions 2 and 2'.

$R^{26}$ and $R^{27}$ each represent an organic group selected from a hydroxyl group, a carboxyl group, and a sulfonic acid group. The organic group is preferably a hydroxyl group. Further, from the viewpoint that the absorbance of the resultant resin can be reduced, $R^{26}$ and $R^{27}$ are preferably in the ortho position relative to the polymer chain. $X^6$ is a single bond, O, S, NH, $SO_2$, CO or a divalent organic group having 1 to 3 carbon atoms or a divalent crosslinked structure formed by linking two or more of these. From the viewpoint that the linear thermal expansion coefficient of the resultant resin can be reduced, $X^6$ is preferably a single bond. $X^7$ and $X^8$ each represent a structure selected from an amide bond and an azomethine bond. From the viewpoint that the absorbance of the resultant resin can be reduced, it is preferably an amide bond.

$a_7$ is an integer of 1 to 4, $b_9$ is an integer of 0 to 3, $a_8$ is an integer of 0 to 4, $b_0$ is an integer of 0 to 4, $b_{11}$ and $b_{12}$ are integers of 0 to 3, $a_7+b_9$ is an integer of 1 to 4, $a_8+b_{10}$ is an integer of 0 to 3, and at least one of $b_9$ and $b_{10}$ is an integer of 1 or more. From the viewpoint that the linear thermal expansion coefficient of the resultant resin can be reduced, it is preferable that $a_7=a_8=1$, $b_9$ and $b_{10}$ are 1 or 2, and $b_{11}$ and $b_{12}$ are 0 or 1, it is more preferable that $a_7=a_8=b_9=b_{10}=1$, and $b_1$ and $b_{12}$ are 0 or 1, and it is most preferable that $a_7=a_8=b_9=b_{10}=1$, and $b_1=b_{12}=0$. $m_5$ and $m_6$ are integers of 0 or 1, and $m_5+m_6$ is an integer of 1 or 2. Preferably, $m_5=m_6=1$.

In the present invention, examples of preferred structures represented by the general formula (7) include the following structures, but the structures are not limited thereto.

[Chemical Formula 16]

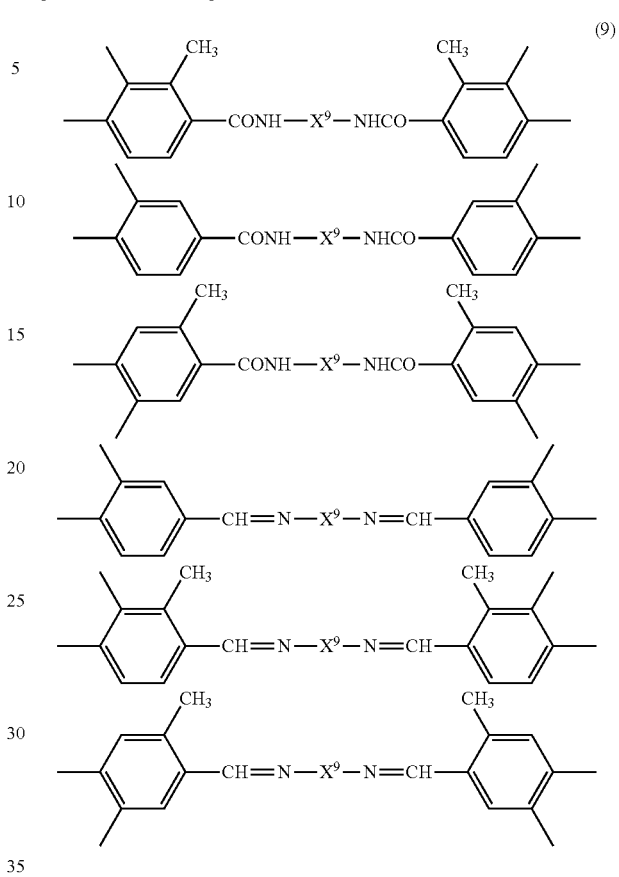

(9)

(In the general formula (9), $X^9$ each independently represents a structure represented by [Chemical Formula 5] to [Chemical Formula 7].)

In the general formulae (3), (4) and (5), $n_2$, $n_3$ and $n_4$ represent a range of 10 to 100,000.

In order to further improve adhesion properties between a heat resistance coating film and a substrate after heat treatment, at least one of both ends of the resin of the present invention may contain a phenol group and/or a thiophenol group. Introduction of an alkali-soluble group to the end can be carried out by imparting the alkali-soluble group to a terminal blocking agent. As the terminal blocking agent, monoamine, acid anhydride, monocarboxylic acid, monoacid chloride compound, monoactive ester compound, or the like can be used.

Specific examples of monoamine used as a terminal blocking agent include 5-amino-8-hydroxyquinoline, 4-amino-8-hydroxyquinoline, 1-hydroxy-8-aminonaphthalene, 1-hydroxy-7-aminonaphthalene, 1-hydroxy-6-aminonaphthalene, 1-hydroxy-5-aminonaphthalene, 1-hydroxy-4-aminonaphthalene, 1-hydroxy-3-aminonaphthalene, 1-hydroxy-2-aminonaphthalene, 1-amino-7-hydroxynaphthalene, 2-hydroxy-7-aminonaphthalene, 2-hydroxy-6-aminonaphthalene, 2-hydroxy-5-aminonaphthalene, 2-hydroxy-4-aminonaphthalene, 2-hydroxy-3-aminonaphthalene, 1-amino-2-hydroxynaphthalene, 1-carboxy-8-aminonaphthalene, 1-carboxy-7-aminonaphthalene, 1-carboxy-6-aminonaphthalene, 1-carboxy-5-aminonaphthalene, 1-carboxy-4-aminonaphthalene, 1-carboxy-3-aminonaphthalene, 1-carboxy-2-aminonaphthalene, 1-amino-7-carboxynaphthalene, 2-carboxy-7-aminonaphthalene, 2-carboxy-6-aminonaphthalene, 2-carboxy-5-aminonaphthalene, 2-carboxy-4-aminonaphthalene, 2-carboxy-3-aminonaphthalene, 1-amino-2-carboxynaphthalene, 2-aminonicotinic acid, 4-aminonicotinic acid, 5-aminonicotinic acid, 6-aminonicotinic acid, 4-aminosalicylic acid, 5-aminosalicylic acid, 6-aminosalicylic acid, 3-amino-o-toluic acid, ammelide, 2-aminobenzoic acid, 3-aminobenzoic acid, 4-aminobenzoic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 5-amino-8-mercaptoquinoline, 4-amino-8-mercaptoquinoline, 1-mercapto-8-aminonaphthalene, 1-mercapto-7-aminonaphthalene, 1-mercapto-6-aminonaphthalene, 1-mercapto-5-aminonaphthalene, 1-mercapto-4-aminonaphthalene, 1-mercapto-3-aminonaphthalene, 1-mercapto-2-aminonaphthalene, 1-amino-7-mercaptonaphthalene, 2-mercapto-7-aminonaphthalene, 2-mercapto-6-aminonaphthalene, 2-mercapto-5-aminonaphthalene, 2-mercapto-4-aminonaphthalene, 2-mercapto-3-aminonaphthalene, 1-amino-2-mercaptonaphthalene, 3-amino-4,6-dimercaptopyrimidine, 2-aminothiophenol, 3-aminothiophenol, and 4-aminothiophenol.

Among them, 5-amino-8-hydroxyquinoline, 1-hydroxy-7-aminonaphthalene, 1-hydroxy-6-aminonaphthalene, 1-hydroxy-5-aminonaphthalene, 1-hydroxy-4-aminonaphthalene, 2-hydroxy-7-aminonaphthalene, 2-hydroxy-6-aminonaphthalene, 2-hydroxy-5-aminonaphthalene, 1-carboxy-7-aminonaphthalene, 1-carboxy-6-aminonaphthalene, 1-carboxy-5-aminonaphthalene, 2-carboxy-7-aminonaphthalene, 2-carboxy-6-aminonaphthalene, 2-carboxy-5-aminonaphthalene, 2-aminobenzoic acid, 3-aminobenzoic acid, 4-aminobenzoic acid, 4-aminosalicylic acid, 5-aminosalicylic acid, 6-aminosalicylic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 2-aminothiophenol, 3-aminothiophenol, 4-aminothiophenol, and the like are preferable. These may be used alone or in combination of two or more.

Specific examples of acid anhydride, monocarboxylic acid, monoacid chloride compound, and monoactive ester compound used as a terminal blocking agent include acid anhydrides such as phthalic anhydride, maleic anhydride, nadic acid, cyclohexanedicarboxylic anhydride, and 3-hydroxyphthalic anhydride; monocarboxylic acids such as 2-carboxyphenol, 3-carboxyphenol, 4-carboxyphenol, 2-carboxythiophenol, 3-carboxythiophenol, 4-carboxythiophenol, 1-hydroxy-8-carboxynaphthalene, 1-hydroxy-7-carboxynaphthalene, 1-hydroxy-6-carboxynaphthalene, 1-hydroxy-5-carboxynaphthalene, 1-hydroxy-4-carboxynaphthalene, 1-hydroxy-3-carboxynaphthalene, 1-hydroxy 2-carboxynaphthalene, 1-mercapto-8-carboxynaphthalene, 1-mercapto-7-carboxynaphthalene, 1-mercapto-6-carboxynaphthalene, 1-mercapto-5-carboxynaphthalene, 1-mercapto-4-carboxynaphthalene, 1-mercapto-3-carboxynaphthalene, 1-mercapto-2-carboxynaphthalene, 2-carboxybenzenesulfonic acid, 3-carboxybenzenesulfonic acid, and 4-carboxybenzenesulfonic acid, and monoacid chloride compounds with the carboxyl group of the monocarboxylic acid formed into an acid chloride; monoacid chloride compounds with only a monocarboxyl group of dicarboxylic acids such as terephthalic acid, phthalic acid, maleic acid, cyclohexanedicarboxylic acid, 3-hydroxyphthalic acid, 5-norbornene-2,3-dicarboxylic acid, 1,2-dicarboxynaphthalene, 1,3-dicarboxynaphthalene, 1,4-dicarboxynaphthalene, 1,5-dicarboxynaphthalene, 1,6-dicarboxynaphthalene, 1,7-dicarboxynaphthalene, 1,8-dicarboxynaphthalene, 2,3-dicarboxynaphthalene, 2,6-dicarboxynaphthalene, and 2,7-dicarboxynaphthalene formed into an acid chloride; and active ester compounds obtained by reaction of a monoacid chloride compound with N-hydroxybenzotriazole and N-hydroxy-5-norbornene-2,3-dicarboxyimide.

Among them, acid anhydrides such as phthalic anhydride, maleic anhydride, nadic acid, cyclohexanedicarboxylic anhydride and 3-hydroxyphthalic anhydride; monocarboxylic acids such as 3-carboxyphenol, 4-carboxyphenol, 3-carboxythiophenol, 4-carboxythiophenol, 1-hydroxy-7-carboxynaphthalene, 1-hydroxy-6-carboxynaphthalene, 1-hydroxy-5-carboxynaphthalene, 1-mercapto-7-carboxynaphthalene, 1-mercapto-6-carboxynaphthalene, 1-mercapto-5-carboxynaphthalene, 3-carboxybenzenesulfonic acid and 4-carboxybenzenesulfonic acid, and monoacid chloride compounds with the carboxyl group of the monocarboxylic acid formed into an acid chloride; monoacid chloride compounds with only a monocarboxyl group of dicarboxylic acids such as terephthalic acid, phthalic acid, maleic acid, cyclohexanedicarboxylic acid, 1,5-dicarboxynaphthalene, 1,6-dicarboxynaphthalene, 1,7-dicarboxynaphthalene, and 2,6-dicarboxynaphthalene formed into an acid chloride; and active ester compounds obtained by reaction of a monoacid chloride compound with N-hydroxybenzotriazole and N-hydroxy-5-norbornene-2,3-dicarboxyimide are preferable. These may be used alone or in combination of two or more.

The content of the terminal sealing agent such as the monoamine, acid anhydride, acid chloride or monocarboxylic acid described above, is preferably within a range of 0.1 mol % to 70 mol %, more preferably from 5 mol % to 50 mol %, of the number of moles of the charged acid component monomer or the charged diamine component monomer. By adjusting the content to such a range, a resin composition that is moderate in viscosity of its solution when applying the resin composition and that has superior film properties can be obtained.

The resin may also have a polymerizable functional group at its end. Examples of the polymerizable functional group include an ethylenically unsaturated linking group, an acetylene group, a methylol group, and an alkoxymethyl group. When a reaction is carried out by selectively combining diamine or tetracarboxylic acid dianhydride in the various known synthesis methods described above, a resin having a terminal blocking agent can be obtained by adding the terminal blocking agent at the same time as them, or slightly thereafter.

The resin of the present invention is characterized by low absorbance. The absorbance at a wavelength of 365 nm per 1 μm thickness of a resin film formed of the resin of the present invention is preferably 0.005 or more and 0.3 or less, more preferably 0.008 or more and 0.2 or less, most preferably 0.01 or more and 0.1 or less. If the absorbance is 0.3 or less, when used for a photosensitive resin composition, energy loss can be reduced by suppressing absorption of the resin itself, and if the absorbance is 0.005 or more, poor pattern formation due to optical reflection from a substrate does not occur. In the case of polyimide represented by the general formula (4), for example, the absorbance is set by selecting the structures of $R^{12}$ and $R^{13}$ and adjusting the copolymerization ratio. The resin having such characteristics can be preferably used from the viewpoint of enhancing photosensitive performance, particularly when a photosensitive resin composition is formed, particularly sensitivity.

The resin film preferably has a film thickness reduction rate of 10 nm/min or more and 30,000 nm/min or less when immersed in a 2.38% tetramethylammonium hydroxide aqueous solution. The film thickness reduction rate is more preferably 50 nm/min or more and 20000 nm/min or less, most preferably 100 nm/min or more and 15000 nm/min or less. If the film thickness reduction rate is 30000 nm/min or less, developability of the resin increases to such an extent that poor pattern formation does not occur when the resin is used in a photosensitive resin composition, and if the film thickness reduction rate is 10 nm/min or more, it is possible to impart solubility capable of obtaining a relief pattern by development. In the case of a polyimide precursor represented by the general formula (3), for example, the film thickness reduction rate is set by, for example, selecting the structures of $R^9$ and $R^{10}$, adjusting the copolymerization ratio, adjusting the proportion of hydrogen in $R^{11}$, or changing $n_2n_1$ and adjusting a molecular weight. The resin having such characteristics can be preferably used from the viewpoint of enhancing photosensitive performance, particularly when a photosensitive resin composition is formed, particularly sensitivity. The term "resin film" used herein refers to a film having a thickness of 3 μm to 10 μm and obtained by applying a γ-butyrolactone solution (resin concentration: 40%) of a resin to a "Pyrex (registered trademark)" glass substrate and baking it on a hotplate (manufactured by Dainippon Screen Mfg. Co., SKW-636) at 120° C. for 2 to 4 minutes.

An average linear thermal expansion coefficient at 50 to 200° C. measured after heat-treating the resin of the present invention at 250° C. is preferably −10 to 40 ppm/° C., more preferably 0 to 30 ppm/° C., further preferably 1 to 25 ppm/° C., and most preferably 3 to 20 ppm/° C. If this average linear thermal expansion coefficient is larger or smaller than this range, there is a possibility that a difference in thermal expansion coefficient from a substrate becomes large, stress caused by the resin applied to the device becomes large, and the yield at the time of device manufacturing and reliability of a product are adversely affected. In the case of polyimide represented by the general formula (4), for example, the average linear thermal expansion coefficient is set by selecting the structures of $R^{12}$ and $R^{13}$ and adjusting the copolymerization ratio. A resin having such characteristics can be preferably used from the viewpoint that warpage of the device can be reduced.

More preferably, the resin of the present invention is precipitated in a poor solvent to the resin, such as methanol or water, after completion of polymerization, followed by washing and drying. Reprecipitation makes it possible to remove esterification agents, condensation agents, by-products of acid chloride, low molecular weight components of resin precursors and the like used at the time of polymerization so that it is advantageously possible to significantly improve mechanical properties after heat curing of a resin composition.

The resin composition of the present invention may contain a solvent in the resin of the present invention and, if necessary, additives for functionalization. Specific examples of the solvent preferably used in the resin composition of the present invention include ethers such as ethyleneglycolmonomethylether, ethyleneglycolmonoethylether, propylene glycol monomethyl ether, propyleneglycolmonoethylether, ethyleneglycoldimethylether, ethyleneglycoldiethylether, ethyleneglycoldibutylether, diethyleneglycoldiethylether, diethyleneglycoldimethylether and diethyleneglycolmethylethylether; acetates such as ethyleneglycolmonomethyletheracetate, propyleneglycolmonomethyletheracetate, propyl acetate, butyl acetate, isobutyl acetate, 3-methoxybutyl acetate, 3-methyl-3-methoxybutyl acetate, methyl lactate, ethyl lactate, and butyl lactate; ketones such as acetylacetone, methyl propyl ketone, methyl butyl ketone, methyl isobutyl ketone, cyclopentanone, and 2-heptanone; alcohols such as butyl alcohol, isobutyl alcohol, pentanol, 4-methyl-2-pentanol, 3-methyl-2-butanol, 3-methyl-3-methoxybutanol, and diacetone alcohol; aromatic hydrocarbons such as toluene and xylene; N-methyl-2-pyrrolidone, N-cyclohexyl-2-pyrrolidone, N,N-dimethylformamide, N,N-dimethylacetamide, dimethyl sulfoxide, and γ-butyrolactone. These can be used alone or in admixture thereof.

The resin composition of the present invention may contain an alkali-soluble resin other than the resin of the present invention. Specific examples thereof include acrylic polymers copolymerized with acrylic acid, phenol resins, siloxane resins, polyhydroxystyrene resins, resins obtained by introducing crosslinking groups such as a methylol group, an alkoxymethyl group and an epoxy group into them, and copolymers thereof. Preferred are phenol resins, polyhydroxystyrene resins, resins obtained by introducing crosslinking groups such as methylol groups, alkoxymethyl groups, and epoxy groups into them, and copolymers thereof. Such a resin is a substance that is soluble in an aqueous solution of an alkali, such as tetramethylammonium hydroxide, choline, triethylamine, dimethylaminopyridine, monoethanolamine, diethylaminoethanol, sodium hydroxide, potassium hydroxide, and sodium carbonate. Inclusion of these alkali-soluble resins enables imparting of properties of each alkali-soluble resin while maintaining adhesion of a heat resistance coating film and excellent sensitivity.

Preferred phenolic resins include novolak resins and resol resins, which can be obtained by polycondensing various phenols alone or a mixture of a plurality of these phenols with aldehydes such as formalin.

Examples of the phenols constituting the novolac resin and the resol resin include phenol, p-cresol, m-cresol, o-cresol, 2,3-dimethylphenol, 2,4-dimethylphenol, 2,5-dimethylphenol, 2,6-dimethylphenol, 3,4-dimethylphenol, 3,5-dimethylphenol, 2,3,4-trimethylphenol, 2,3,5-trimethylphenol, 3,4,5-trimethylphenol, 2,4,5-trimethylphenol, methylenebisphenol, methylenebis p-cresol, resorcin, catechol, 2-methylresorcin, 4-methylresorcin, o-chlorophenol, m-chlorophenol, p-chlorophenol, 2,3-dichlorophenol, m-methoxyphenol, p-methoxyphenol, p-butoxyphenol, o-ethylphenol, m-ethylphenol, p-ethylphenol, 2,3-diethylphenol, 2,5-diethylphenol, p-isopropylphenol, α-naphthol, and β-naphthol, and these can be used alone or as a mixture of two or more.

In addition to formalin, examples of aldehydes include paraformaldehyde, acetaldehyde, benzaldehyde, hydroxybenzaldehyde, and chloroacetaldehyde, which can be used alone or as a mixture of two or more.

The phenol resin used in the present invention may have a structure in which one to four hydrogen atoms added to an aromatic ring are partially substituted with an alkyl group having 1 to 20 carbon atoms, a fluoroalkyl group, an alkoxyl group, an ester group, a nitro group, a cyano group, a fluorine atom, or a chlorine atom.

The weight average molecular weight of the phenol resin used in the present invention is within a range of 2,000 to 50,000, preferably a range of 3,000 to 30,000 in terms of polystyrene using gel permeation chromatography (GPC). When the molecular weight is 2,000 or more, it is excellent in pattern shape, resolution, developability and heat resistance, and when the molecular weight is 50,000 or less, sufficient sensitivity can be maintained.

Preferable examples of the polyhydroxystyrene resin include polymers or copolymers, obtained by polymerizing by a known method at least one of aromatic vinyl compounds having a phenolic hydroxyl group, such as p-hydroxystyrene, m-hydroxystyrene, o-hydroxystyrene, p-isopropenylphenol, m-isopropenylphenol, and o-isopropenylphenol, and polymers or copolymers obtained by adding and reacting by a known method an alkoxy group to/with a portion of polymers or copolymers obtained by polymerizing by a known method at least one of aromatic vinyl compounds such as styrene, o-methylstyrene, m-methylstyrene, and p-methylstyrene.

As the aromatic vinyl compound having a phenolic hydroxyl group, p-hydroxystyrene and/or m-hydroxystyrene are/is preferably used, and as the aromatic vinyl compound, styrene is preferably used.

The polyhydroxystyrene resin used in the present invention may have a structure in which one to four hydrogen atoms added to an aromatic ring are partially substituted with an alkyl group having 1 to 20 carbon atoms, a fluoroalkyl group, an alkoxyl group, an ester group, a nitro group, a cyano group, a fluorine atom, or a chlorine atom.

The weight average molecular weight of the polyhydroxystyrene resin used in the present invention is preferably within a range of 3,000 to 60,000, more preferably a range of 3,000 to 25,000 in terms of polystyrene using gel permeation chromatography (GPC). When the molecular weight is 3,000 or more, it is excellent in pattern shape, resolution, developability and heat resistance, and when the molecular weight is 60,000 or less, sufficient sensitivity can be maintained.

The content of such a phenolic resin or polyhydroxystyrene resin in the resin composition is from 5 to 50 parts by weight, preferably from 10 to 40 parts by weight, based on 100 parts by weight of the resin of the present invention. If the content is 40 parts by weight or less, the heat resistance and strength of the heat resistance coating film after heat treatment can be maintained, whereas if the content is 10 parts by weight or more, the pattern formability of the resin film is improved.

The resin composition of the present invention may contain a photo acid generator and can impart positive type photosensitivity. Although examples of the photo acid generator include a quinone diazide compound, a sulfonium salt compound, a phosphonium salt compound, a diazonium salt compound, and an iodonium salt compound, the quinone diazide compound is preferable, and an o-quinonediazide compound is particularly preferable. Examples of the quinonediazide compound include a compound in which the sulfonic acid of quinone diazide has been bonded to a polyhydroxy compound via an ester, a compound in which the sulfonic acid of quinone diazide has been sulfonamide-bonded to a polyamino compound, and a compound in which the sulfonic acid of quinone diazide has been ester-bonded and/or sulfonamide-bonded to a polyhydroxy-polyamino compound. Although all functional groups of these polyhydroxy compounds and polyamino compounds may not be substituted with quinone diazide, it is preferable that 50 mol % or more of the whole functional groups have been substituted with quinone diazide. When 50 mol % or more is substituted with quinone diazide, solubility of the resin film in an alkaline developer becomes satisfactory, and it is advantageously possible to obtain a fine pattern with high contrast with an unexposed portion. By using such a quinonediazide compound, it is possible to obtain a resin composition having positive photosensitivity to the i-line (365 nm), h-line (405 nm), and g-line (436 nm) of mercury lamps, which are commonly used ultraviolet rays.

Examples of the polyhydroxy compound include, but are not limited to, Bis-Z, BisP-EZ, TekP-4HBPA, TrisP-HAP, TrisP-PA, TrisP-SA, TrisOCR-PA, BisOCHP-Z, BisP-MZ, BisP-PZ, BisP-IPZ, BisOCP-IPZ, BisP-CP, BisRS-2P, BisRS-3P, BisP-OCHP, methylenetris-FR-CR, BisRS-26X, DML-MBPC, DML-MBOC, DML-OCHP, DML-PCHP, DML-PC, DML-PTBP, DML-34X, DML-EP, DML-POP, dimethylol-BisOC-P, DML-PFP, DML-PSBP, DML-MTrisPC, TriML-P, TriML-35XL, TML-BP, TML-HQ, TML-pp-BPF, TML-BPA, TMOM-BP, HML-TPPHBA, and HML-TPHAP (trade names, each produced by Honshu Chemical Industry Co., Ltd.); BIR-OC, BIP-PC, BIR-PC, BIR-PTBP, BIR-PCHP, BIP-BIOC-F, 4PC, BIR-BIPC-F, TEP-BIP-A, 46DMOC, 46DMOEP, and TM-BIP-A (trade names, each produced by Asahi Organic Chemicals Industry Co., Ltd.); 2,6-dimethoxymethyl-4-t-butylphenol, 2,6-dimethoxymethyl-p-cresol, 2,6-diacetoxymethyl-p-cresol, naphthol, tetrahydroxybenzophenone, gallic acid methyl ester, bisphenol A, bisphenol E, and methylene bisphenol; and BisP-AP (trade name, produced by Honshu Chemical Industry Co., Ltd.)

Examples of the polyamino compound include, but are not limited to, 1,4-phenylenediamine, 1,3-phenylenediamine, 4,4'-diaminodiphenylether, 4,4'-diaminodiphenylmethane, 4,4'-diaminodiphenylsulfone, and 4,4'-diaminodiphenyl sulfide. Examples of the polyhydroxypolyamino compound include, but are not limited to, 2,2-bis(3-amino-4-hydroxyphenyl)hexafluoropropane, and 3,3'-dihydroxybenzidine.

In the present invention, both a 5-naphthoquinonediazidesulfonyl group and a 4-naphthoquinonediazidesulfonyl group are preferably used in quinonediazide. A 4-naphthoquinonediazide sulfonyl ester compound is suitable for i-line exposure because it has an absorption in the i-line region of a mercury lamp. A 5-naphthoquinonediazide sulfonyl ester compound is suitable for g-line exposure because it has an absorption extending to the g-line region of a mercury lamp. In the present invention, it is preferable to choose a 4-naphthoquinonediazide sulfonyl ester compound and a 5-naphthoquinonediazide sulfonyl ester compound depending upon the wavelength of light to be applied. A naphthoquinonediazide sulfonyl ester compound that uses both a 4-naphthoquinone diazide sulfonyl group and a 5-naphthoquinone diazide sulfonyl group in the same molecule can be obtained, and both a 4-naphthoquinonediazide sulfonyl ester compound and a 5-naphthoquinonediazide sulfonyl ester compound can be used together.

The molecular weight of a quinonediazide compound is preferably 300 or more, more preferably 350 or more. The molecular weight of the quinonediazide compound is preferably 1500 or less, and more preferably 1200 or less. If the molecular weight is 300 or more, exposure sensitivity becomes high. If the molecular weight is 1500 or less, there is an advantage that the mechanical properties of the heat resistance coating film after heat treatment are improved.

The content of the photo acid generator is preferably 1 part by weight or more, more preferably 3 parts by weight or more, based on 100 parts by weight of the resin as the whole resin composition. The content of the photo acid generator is preferably 50 parts by weight or less, more preferably 40 parts by weight or less. In the case of a quinonediazide compound, the content is preferably 1 part by weight or more, more preferably 3 parts by weight or more, based on 100 parts by weight of the resin. The content of the photo acid generator is preferably 50 parts by weight or less, more preferably 40 parts by weight or less. Within this range, there is an advantage that the mechanical properties of the heat resistance coating film after heat treatment are improved.

The quinonediazide compound used in the present invention is synthesized from a specific phenol compound by the following method. For example, there is a method of reacting 5-naphthoquinonediazide sulfonyl chloride and a phenol compound in the presence of triethylamine. As a method of synthesizing a phenol compound, there is a method of reacting an α-(hydroxyphenyl)styrene derivative with a polyhydric phenol compound under an acid catalyst.

Since the heat resistance coating film after heat treatment obtained from the resin composition of the present invention is used as a permanent film, it is environmentally undesirable that phosphorus and the like remain, since color tone of the film also needs to be taken into consideration, among the examples of photoacid generators, the sulfonium salt compound, phosphonium salt compound, and diazonium salt compound are preferable, and sulfonium salts are preferably used. Especially preferred are triarylsulfonium salts.

In the resin composition of the present invention, in order to impart negative photosensitivity, as $R^1$ in the general formula (3), there can be used a group having an ethylenically saturated double bond such as an ethylmethacrylate group, an ethyl acrylate group, a propylmethacrylate group, a propyl acrylate group, an ethyl methacrylamide group, a propylmethacrylamide group, an ethylacrylamide group, and a propylacrylamide group. In addition, in order to improve the photosensitive performance of the resin composition, it is preferable to include a photopolymerizable compound. Examples of the photopolymerizable compound include, but are not limited to, 2-hydroxyethyl methacrylate, trimethylolpropane trimethacrylate, trimethylolpropane triacrylate, ethylene glycol dimethacrylate, diethylene glycol dimethacrylate, triethylene glycol dimethacrylate, tetraethylene glycol dimethacrylate, propylene glycol dimethacrylate, methylenebismethacrylamide, and methylenebisacrylamide. The photopolymerizable compound is preferably contained in a range of 1 to 30 parts by weight based on 100 parts by weight of the resin. Within this range, a composition which has high sensitivity and in which the mechanical properties of the film after thermal curing is satisfactory is provided. These photopolymerizable compounds can be used alone or in combination of two or more.

When negative photosensitivity is imparted to the resin composition of the present invention, a photopolymerization initiator may be contained. Examples of the photopolymerization initiator suitable for the present invention include, but are not limited to, aromatic amines such as N-phenyldiethanolamine and N-phenylglycine, aromatic ketones such as Michler's ketone, cyclic oxime compounds typified by 3-phenyl-5-isoxazolone, chain oxime compounds typified by 1-phenylpropanedione-2-(o-ethoxycarbonyl)oxime, benzophenone derivatives such as benzophenone, o-benzoyl methyl benzoate, dibenzyl ketone, and fluorenone, and thioxanthone derivatives such as thioxanthone, 2-methylthioxanthone, and 2-isopropylthioxanthone.

The content of the photopolymerization initiator is preferably 0.01 parts by weight or more, more preferably 0.1 parts by weight or more, based on 100 parts by weight of the resin. The content of the photopolymerization initiator is preferably 30 parts by weight or less, more preferably 20 parts by weight or less. Within this range, a composition which has high sensitivity and in which the mechanical properties of the film after thermal curing is satisfactory is provided. These photopolymerization initiators can be used alone or in combination of two or more.

In order to further improve negative photosensitive characteristics, it is more preferable to contain a photosensitizer. Examples of the photosensitizer suitable for the present invention include aromatic monoazide such as azidoanthraquinone and azidobenzalacetophenone, aminocoumarins such as 7-diethylaminobenzoyl coumarin and 3,3'-carbonylbis(diethylaminocoumarin), aromatic ketones such as benzanthrone and phenanthrenequinone, and those generally used in photo-curable resins. In addition, those which are used as a charge transfer agent of an electrophotographic photoreceptor can also be preferably used.

The content of the photosensitizer is preferably 0.01 parts by weight, more preferably 0.1 parts by weight or more, based on 100 parts by weight of the resin. The content of the photosensitizer is preferably 30 parts by weight or less, more preferably 20 parts by weight or less. Within this range, the sensitivity is high, and the mechanical properties of the heat resistance coating film after heat treatment are improved. These photosensitizers can be used alone or in combination of two or more.

The resin composition of the present invention may contain a compound having a phenolic hydroxyl group for the purpose of controlling an alkali developing property of the resin film formed from the resin composition. Examples of the compound with a phenolic hydroxyl group which can be used in the present invention include Bis-Z, BisOC-Z, BisOPP-Z, BisP-CP, Bis26X-Z, BisOTBP-Z, BisOCHP-Z, BisOCR-CP, BisP-MZ, BisP-EZ, Bis26X-CP, BisP-PZ, BisP-IPZ, BisCR-IPZ, BisOCP-IPZ, BisOIPP-CP, Bis26X-IPZ, BisOTBP-CP, TekP-4HBPA (tetrakis P-DO-BPA), TrisP-HAP, TrisP-PA, BisOFP-Z, BisRS-2P, BisPG-26X, BisRS-3P, BisOC-OCHP, BisPC-OCHP, Bis25X-OCHP, Bis26X-OCHP, BisOCHP-OC, Bis236T-OCHP, methylene tris-FR-CR, BisRS-26X, and BisRS-OCHP (trade names, produced by Honshu Chemical Industry Co., Ltd.); and BIR-OC, BIP-PC, BIR-PC, BIR-PTBP, BIR-PCHP, BIP-BIOC-F, 4PC, BIR-BIPC-F, and TEP-BIP-A (trade names, produced by Asahi Organic Chemicals Industry Co., Ltd.).

Among them, examples of preferred compounds having a phenolic hydroxyl group include Bis-Z, BisP-EZ, TekP-4HBPA, TrisP-HAP, TrisP-PA, BisOCHP-Z, BisP-MZ, BisP-PZ, BisP-IPZ, BisOCP-IPZ, BisP-CP, BisRS-2P, BisRS-3P, BisP-OCHP, methylene tris-FR-CR, BisRS-26X, BIP-PC, BIR-PC, BIR-PTBP, and BIR-BIPC-F. Among them, particularly preferred compounds having a phenolic hydroxyl group are Bis-Z, TekP-4HBPA, TrisP-HAP, TrisP-PA, BisRS-2P, BisRS-3P, BIR-PC, BIR-PTBP, and BIR-BIPC-F. By adding the compound having a phenolic hydroxy group, the resultant resin composition can easily be dissolved in an alkaline developer before exposure and hardly dissolved in the alkaline developer after exposure, leading to decreased film reduction due to development and easily accomplishing development within a short period of time. The content of such a compound having a phenolic hydroxyl group is preferably from 1 to 60 parts by weight, more preferably from 3 to 50 parts by weight, based on 100 parts by weight of the resin.

The resin composition of the present invention may contain a heat-crosslinker. Examples of the heat-crosslinker include a methylol compound, a methoxymethylol compound, a urea compound, an epoxy compound, and an oxetane compound, but any compound can be preferably used. Specific examples of a heat-crosslinker include: as those having one of such a thermally crosslinkable group, ML-26X, ML-24X, ML-236TMP, 4-methylol 3M6C, ML-MC, and ML-TBC (trade names, produced by Honshu Chemical Industry Co., Ltd.), and P-a type benzoxazine (trade name, produced by Shikoku Chemicals Corp.); as those having two or more of such thermally crosslinkable groups, DM-BI25X-F, 46DMOC, 46DMOIPP, 46DMOEP, and TM-BIP-A (trade names, produced by Asahi Organic Chemicals Industry Co., Ltd.), DML-MBPC, DML-MBOC, DML-OCHP, DML-PC, DML-PCHP, DML-PTBP, DML-34X, DML-EP, DML-POP, DML-OC, dimethylol-Bis-C, dimethylol-BisOC-P, DML-BisOC-Z, DML-BisOCHP-Z, DML-PFP, DML-PSBP, DML-MB25, DML-MTrisPC, DML-Bis25X-34XL, and DML-Bis25X-PCHP, 2,6-dimethoxymethyl-4-t-butylphenol, 2,6-dimethoxymethyl-p-cresol, 2,6-diacetoxymethyl-p-cresol, TriML-P, TriML-35XL, TriML-TrisCR-HAP, TML-BP, TML-HQ, TML-pp-BPF, TML-BPA, TMOM-BP, HML-TPPHBA, HML-TPHAP, HMOM-TPPHBA, and HMOM-TPHAP (trade names, produced by Honshu Chemical Industry Co., Ltd.), Nikalac (registered trademark) MX-290, Nikalac MX-280, Nikalac MX-270, Nikalac MW-390, and Nikalac MW-100LM (trade names, produced by Sanwa Chemical Co., Ltd.), B-a type benzoxazine and B-m type benzoxazine (trade names, produced by Shikoku Chemicals Corp.), Epolight 40E, Epolight 100E, Epolight 200E, Epolight 400E, Epolight 70P, Epolight 200P, Epolight 400P, Epolight 1500NP, Epolight 80MF, Epolight 4000, and Epolight 3002 (trade names, produced by Kyoeisha Chemical Co., Ltd.), Denacol (registered trademark) EX-212L, Denacol EX-214L, Denacol EX-216L, Denacol EX-850L and Denacol EX-321L (trade names, produced by Nagase ChemteX Corporation), GAN, GOT, NC3000, EPPN502H, and NC3000 (trade names, produced by Nippon Kayaku Co., Ltd.), jER (registered trademark) 828, jER1002, jER1750, jER1007, jERYX8100-BH30, jER1256, jER4250, and jER4275 (trade names, produced by Mitsubishi Chemical Corporation), EPICLON (registered trademark) EXA-9583, EPICLON HP4032, EPICLON N695, and EPICLON HP7200 (trade names, produced by Dainippon Ink and Chemicals Inc.), TEPIC (registered trademark) S, TEPIC G, and TEPIC P (trade names, produced by Nissan Chemical Industries, Ltd.), ETERNACOLL (registered trademark) EHO, ETERNACOLL OXBP, ETERNACOLL OXTP, and ETERNACOLL OXMA (trade names, produced by Ube Industries, Ltd.), and oxetane-modified phenol novolac.

In particular, a methoxymethylol compound is preferably used from the standpoint of standing stability after exposure.

When these heat-crosslinkers are contained, a film in which the shrinkage after curing is small and which has high dimensional reproducibility is obtained. When the composition is photosensitive, it is hardly dissolved in an alkali developer before exposure and easily dissolved in the alkali developer after exposure, so that there are advantages that film reduction due to development is small, and development can be accomplished within a short period of time. The content of the heat-crosslinker is preferably 0.5 parts by weight or more, more preferably 3 parts by weight or more, and on the other hand, preferably 50 parts by weight or less, more preferably 40 parts by weight or less, based on 100 parts by weight of the resin. Within this range, there is an advantage that the chemical resistance of the composition is improved.

In order to further improve adhesion between the heat resistance coating film after heat treatment and a silicon-based substrate, such as silicon, silicon nitride, silicon oxide, and phosphorus silicate glass, an ITO substrate, and various metal substrates or to enhance resistance to oxygen plasma used for cleaning and the like and UV ozone treatment, the resin composition of the present invention may contain adhesion promoters such as a silane coupling agent, a titanium chelating agent, an aluminum chelating agent, an alkoxysilane-containing aromatic amine compound, and an aromatic amide compound. Preferred specific examples of silane coupling agents include N-phenylaminoethyltrimethoxysilane, N-phenylaminoethyltriethoxysilane, N-phenylaminopropyltrimethoxysilane, N-phenylaminopropyltriethoxysilane, N-phenylaminobutyltrimethoxysilane, N-phenylaminobutyltriethoxysilane, vinyltrimethoxysilane, vinyltriethoxysilane, vinyltrichlorosilane, vinyltris(β-methoxyethoxy)silane, 3-methacryloxypropyltrimethoxysilane, 3-acrylroxypropyltrimethoxysilane, p-styryltrimethoxysilane, 3-methacryloxypropylmethyldimethoxysilane, and 3-methacryloxypropylmethyldiethoxysilane. Preferred specific examples of alkoxysilane-containing aromatic amine compounds and aromatic amide compounds are provided below. In addition, compounds obtainable by reacting an aromatic amine compound with an alkoxy group-containing silicon compound can also be used, and examples thereof include compounds obtainable by reacting an aromatic amine compound with an alkoxysilane compound having a group that reacts with an amino group, such as an epoxy group and a chloromethyl group.

[Chemical Formula 17]

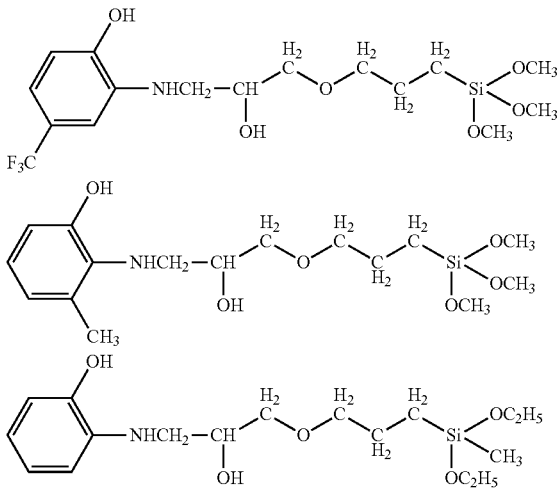

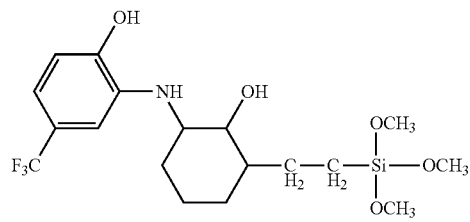
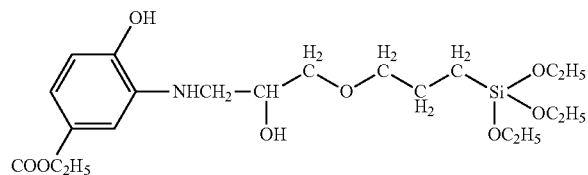
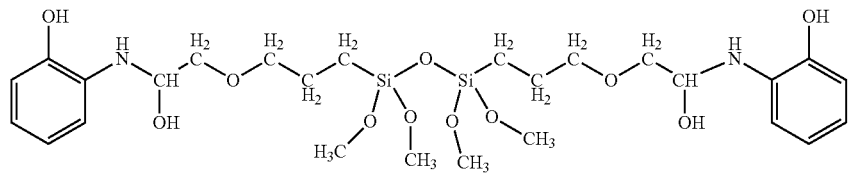
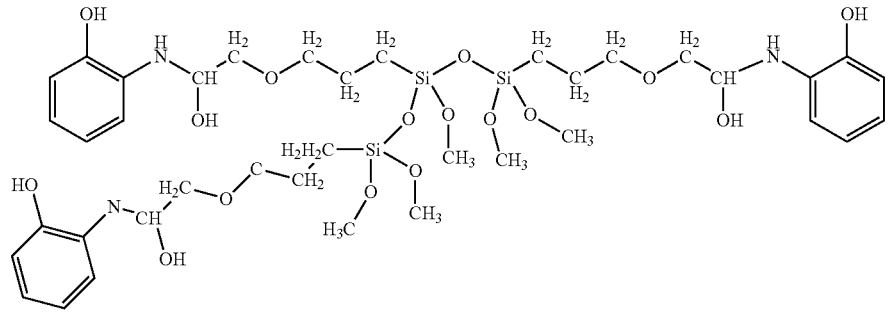
[Chemical Formula 18]
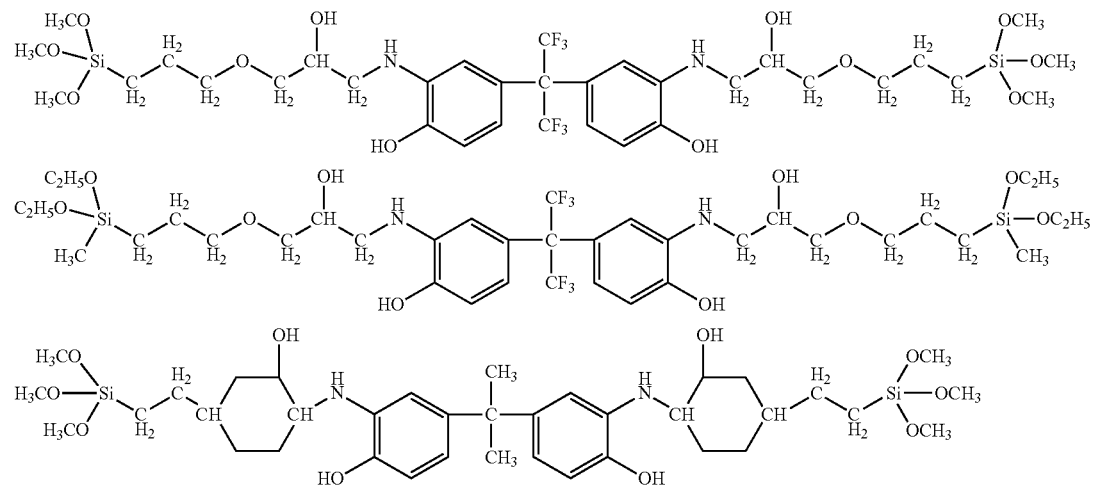

-continued
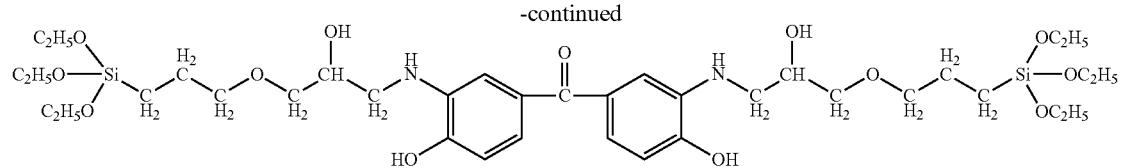
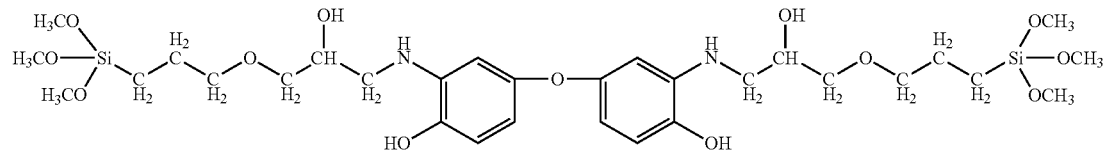
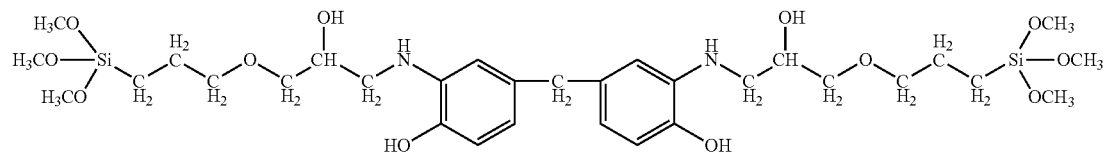
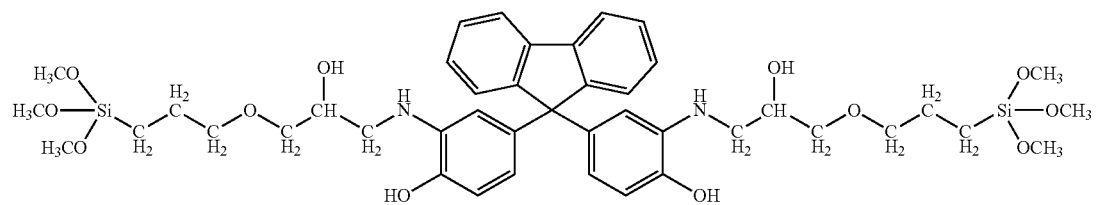
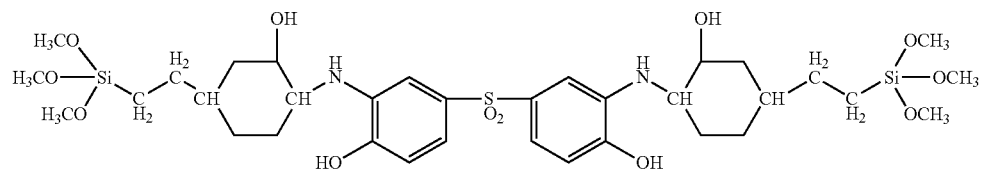 [SMILES: CO[Si](CCC1CCC(Nc2cc(S(=O)(=O)c3ccc(O)c(NC4CCC(CC[Si](OC)(OC)OC)CC4O)c3)ccc2O)C(O)C1)(OC)OC]
[Chemical Formula 19]
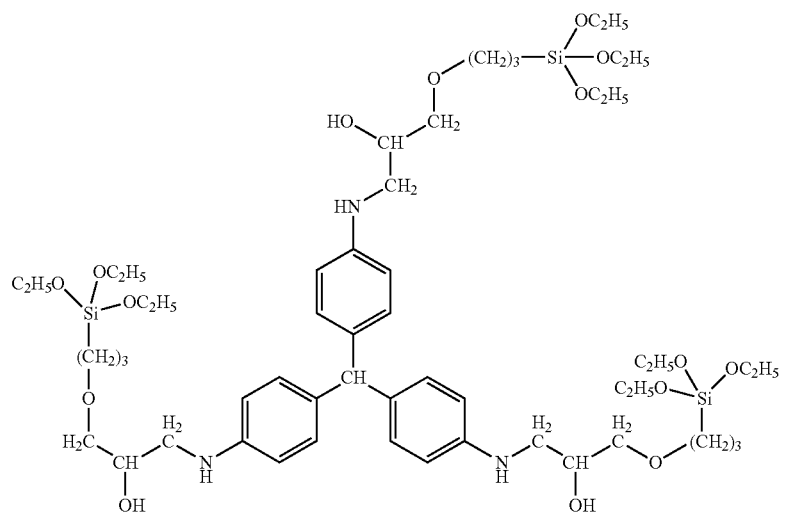

-continued

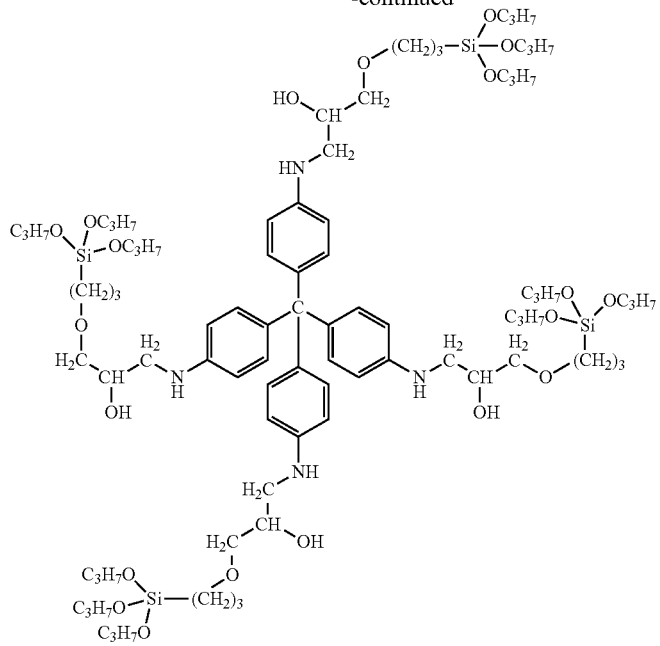

The content of the adhesion promoter is preferably from 0.01 to 15 parts by weight based on 100 parts by weight of the resin.

The adhesion can be further improved by pretreating a surface of a silicon-based material which is a substrate to which the resin composition is applied. As the pretreatment method, the following method is exemplified. A solution obtained by dissolving 0.5 to 20 parts by weight of the above-described adhesion promoter in 100 parts by weight of a solvent such as isopropanol, ethanol, methanol, water, tetrahydrofuran, propyleneglycolmonomethyletheracetate, propylene glycol monomethyl ether, ethyl lactate, and diethyl adipate is used for surface treatment by means of spincoating, dipping, spray coating, vapor treatment, etc. Alternatively, surface treatment may be performed by directly spraying hexamethyldisilazane vapor. Then, if necessary, drying treatment under reduced pressure is carried out, and heating to 50 to 300° C. is carried out, so that the reaction between the surface of the silicon-based material and the adhesion promotor is advanced.

The resin composition of the present invention may contain a surfactant, and wettability with the substrate can be improved. Examples of the surfactant include fluorine-based surfactants, such as Fluorad (trade name, produced by Sumitomo 3M Ltd.), Megafac (registered trademark) (trade name, produced by DIC Corporation), and Sulfron (trade name, produced by Asahi Glass Co., Ltd.), organic siloxane surfactants, such as KP341 (trade name, produced by Shin-Etsu Chemical Co., Ltd.), DBE (trade name, produced by Chisso Corporation), GLANOL (trade name, produced by Kyoeisha Chemical Co., Ltd.), and BYK (produced by BYK-Chemie), and acrylic polymer surfactants such as POLYFLOW (trade name, produced by Kyoeisha Chemical Co., Ltd.).

The resin composition of the present invention may contain a heat chromogenic compound. The heat chromogenic compound is colored by heat treatment and has an absorbance maximum at 350 nm or more and 700 nm or less, and preferably, the heat chromogenic compound is colored by heat treatment and has an absorbance maximum at 350 nm or more and 500 nm or less. The heat chromogenic compound may be a general thermal dye or pressure sensitive dye, or may be another compound. Examples of such a heat chromogenic compound include those which develop color by changing the chemical structures or state of electric charge by the action of acidic groups exiting in the system during heat treatment, and those which develop color by thermal oxidation reaction or the like with the oxygen in the air. Examples of the skeleton structure of the heat chromogenic compound include a triarylmethane skeleton, a diarylmethane skeleton, a fluoran skeleton, a bislactone skeleton, a phthalide skeleton, a xanthene skeleton, a rhodamine lactam skeleton, a fluorene skeleton, a phenothiazine skeleton, a phenoxazine skeleton, and a spiropyran skeleton. Specific examples thereof include 4,4',4''-tris(dimethylamino)triphenylmethane, 4,4',4''-tris(diethylamino)-2-,2', 2''-trimethyltriphenylmethane, 2,4',4''-methylidenetrisphenol, 4,4',4''-methylidenetrisphenol, 4,4'-[(4-hydroxyphenyl)methylene]bis(benzeneamine), 4,4'-[(4-aminophenyl)methylene]bisphenol, 4,4'-[(4-aminophenyl)methylene]bis[3,5-dimethylphenol], 4,4'-[(2-hydroxyphenyl)methylene]bis[2,3,6-trimethylphenol], 4-[bis(4-hydroxyphenyl)methyl]-2-methoxyphenol, 4,4'-[(2-hydroxyphenyl)methylene]bis[2-methylphenol], 4,4'-[(4-hydroxyphenyl)methylene]bis[2-methylphenol], 4-[bis(4-hydroxyphenyl)methyl]-2-ethoxyphenol, 4,4'-[(3-hydroxyphenyl)methylene]bis[2,6-dimethylphenol], 4,4'-[(4-hydroxyphenyl)methylene]bis[2,6-dimethylphenol], 2,2'-[(4-hydroxyphenyl)methylene]bis[3,5-dimethylphenol], 4,4'-[(4-hydroxy-3-methoxyphenyl)methylene]bis[2,6-dimethylphenol], 2,2'-[(2-hydroxyphenyl)methylene]bis[2,3,5-trimethylphenol], 4,4'-[(4-hydroxyphenyl)methylene]bis[2,3,6-trimethylphenol], 4,4'-[(2-hydroxyphenyl)methylene]bis[2-cyclohexyl-5-methylphenol], 4,4'-[(3-hydroxyphenyl)methylene]bis[2-cyclohexyl-5-methylphenol], 4,4'-[(4-hydroxyphenyl)methylene]bis[2-cyclohexyl-5-methylphenol], 4,4'-[(3-methoxy-4-hydroxyphenyl)methylene]bis[2-cyclohexyl-5-methylphenol], 4,4'-[(3,4- dihydroxyphenyl)methylene]bis[2-methylphenol], 4,4'-[(3,4-dihydroxyphenyl)methylene]bis[2,6-dimethylphenol], 4,4'-[(3,4-dihydroxyphenyl)methylene]bis[2,3,6-trimethylphenol], 4-[bis(3-cyclohexyl-4-hydroxy-6-methylphenyl)methyl]-1,2-benzenediol, 4,4',4'',4'''-(1,2-ethanediylidene)tetrakisphenol, 4,4',4'',4'''-(1,2-ethanediylidene)tetrakis[2-methylphenol], 4,4',4'',4'''-(1,2-ethanediylidene)tetrakis[2,6-dimethylphenol], 4,4',4'',4'''-(1,4-phenylenedimethylidene)tetrakisphenol, 4,4',4'',4'''-(1,4-phenylenedimethylidene)tetrakis(2,6-dimethylphenol), 4,4'-[(2-hydroxyphenyl)methylene]bis[3-methylphenol], 2,2'-[(3-hydroxyphenyl)methylene]bis[3,5-dimethylphenol], 4,4'-[(2-hydroxy-3-methoxyphenyl)methylene]bis[2,5-dimethylphenol], 4,4'-[(2-hydroxy-3-methoxyphenyl)methylene]bis[2,6-dimethylphenol], 2,2'-[(2-hydroxy-3-methoxyphenyl)methylphenol], 2,2'-[(3-hydroxy-4-methoxyphenyl)methylene]bis[3,5-phenol], 4,4'-[(2-hydroxyphenyl)methylene]bis[2-methylethylphenol], 4,4'-[(3-hydroxyphenyl)methylene]bis[2-methylethylphenol], 4,4'-[(4-hydroxyphenyl)methylene]bis[2-methylethylphenol], 2,2'-[(3-hydroxyphenyl)methylene]bis[3,5,6-trimethylphenol], 2,2'-[(4-hydroxyphenyl)methylene]bis[3,5,6-trimethylphenol], 2,2'-[(4-hydroxy-3-ethoxyphenyl)methylene]bis[3,5-dimethylphenol], 4,4'-[(2-hydroxy-3-methoxyphenyl)methylene]bis[2-(methylethyl)phenol], 4,4'-[(3-hydroxy-4-methoxyphenyl)methylene]bis[2-(methylethyl)phenol], 4,4'-[(4-hydroxy-3-methoxyphenyl)methylene]bis[2-(methylethyl)phenol], 2,2'-[(2-hydroxy-3-methoxyphenyl)methylene]bis[3,5,6-trimethylphenol], 2,2'-[(3-hydroxy-4-methoxyphenyl)methylene]bis[3,5,6-trimethylphenol], 2,2'-[(4-hydroxy-3-methoxyphenyl)methylene]bis[3,5,6-trimethylphenol], 4,4'-[(4-hydroxy-3-ethoxyphenyl)methylene]bis[2-(methylethyl)phenol], 2,2'-[(4-hydroxy-3-ethoxyphenyl)methylene]bis[3,5,6-trimethylphenol], 4,4'-[(4-hydroxy-3-ethoxyphenyl)methylene]bis[2,3,6-trimethylphenol], 4,4'-[(4-hydroxy-3-methoxyphenyl)methylene]bis[2-(1,1-dimethylethyl)-5-methylphenol], 4,4'[(2-hydroxyphenyl)methylene]bis[2-cyclohexylphenol], 4,4'-[(3-hydroxyphenyl)methylene]bis[2-cyclohexylphenol], 4,4'-[(4-hydroxyphenyl)methylene]bis[2-cyclohexylphenol], 4,4'-[(2-hydroxy-3-methoxyphenyl)methylene]bis[2-cyclohexylphenol], 4,4'-[(3-hydroxy-4-methoxyphenyl)methylene]bis[2-cyclohexylphenol], 4,4'-[(4-hydroxy-3-ethoxyphenyl)methylene]bis[2-(1,1-dimethylethyl)-6-methylphenol], 4,4'-[(4-hydroxy-3-ethoxyphenyl)methylene]bis[2-cyclohexyl-5-methylphenol], 4,4',4''-methylidenetris[2-cyclohexyl-5-methylphenol], 2,2'-[(3,4-dihydroxyphenyl)methylene]bis[3,5-dimethylphenol], 4,4'-[(3,4-dihydroxyphenyl)methylene]bis[2-(methylethyl)phenol], 2,2'-[(3,4-dihydroxyphenyl)methylene]bis[3,5,6-trimethylphenol], 4,4'-[(3,4-dihydroxyphenyl)methylene]bis[2-cyclohexylphenol], 3,3'-[(2-hydroxyphenyl)methylene]bis[5-methylbenzene-1,2-diol], 4,4'-[4-[[bis(4-hydroxy-2,5-dimethylphenyl)methyl]phenyl]methylene]bis[1,3-benzenediol], 4,4'-methylenebis[2-[di(4-hydroxy-3-methylphenyl)]methyl]phenol, 4,4'-methylenebis[2-[di(4-hydroxy-2,5-dimethylphenyl)]methyl]phenol, 4,4'-methylenebis[2-[di(4-hydroxy-3,5-dimethylphenyl)]methyl]phenol, 4,4'-methylenebis[2-[di(3-cyclohexyl-4-hydroxy-6-methylphenyl)]methyl]phenol, 4,4'-(3,5-dimethyl-4-hydroxyphenylmethylene)-bis(2,6-dimethylphenol), 3,3-bis(p-dimethylaminophenyl)-6-dimethylaminophthalide, 3,6-bis(dimethylamino)fluorane-γ-(4'-nitro)-aminolactam, 2-(2-chloroanilino)-6-diethylaminofluorane, 2-(2-chloroanilino)-6-dibutylaminofluorane, 2-N,N-dibenzylamino-6-diethylaminofluorane, 6-diethylamino-benzo [a]-fluorane, 2,2'-bis(2-chlorophenyl)-4,4',5,5'-tetraphenyl-1,2'-bi(imidazole), 1,3-dimethyl-6-diethylaminofluorane, 2-anilino-3-methyl-6-dibutylaminofluorane, 3,7-bis(dimethylamino)-10-benzoylphenothiazine, 3-diethylamino-6-chloro-7-(β-ethoxyethylamino)fluorane, 3-diethylamino-6-methyl-7-anilinofluorane, 3-triethylamino-6-methyl-7-anilinofluorane, and 3-cyclohexylamino-6-methyl-7-anilinofluorane.

Among them, a hydroxyl group-containing compound having a triarylmethane skeleton is preferable. Specific examples thereof include 2,4',4''-methylidenetrisphenol, 4,4',4''-methylidenetrisphenol, 4,4'-[(4-hydroxyphenyl)methylene]bis(benzeneamine), 4,4'-[(4-aminophenyl)methylene]bisphenol, 4,4'-[(4-aminophenyl)methylene]bis[3,5-dimethylphenol], 4,4'-[(2-hydroxyphenyl)methylene]bis[2,3,6-trimethylphenol], 4-[bis(4-hydroxyphenyl)methyl]-2-methoxyphenol, 4,4'-[(2-hydroxyphenyl)methylene]bis[2-methylphenol], 4,4'-[(4-hydroxyphenyl)methylene]bis[2-methylphenol], 4-[bis(4-hydroxyphenyl)methyl]-2-ethoxyphenol, 4,4'-[(4-hydroxyphenyl)methylene]bis[2,6-dimethylphenol], 2,2'-[(4-hydroxyphenyl)methylene]bis[3,5-dimethylphenol], 4,4'-[(4-hydroxy-3-methoxyphenyl)methylene]bis[2,6-dimethyl phenol], 2,2'-[(2-hydroxyphenyl)methylene]bis[2,3,5-trimethylphenol], 4,4'-[(4-hydroxyphenyl)methylene]bis[2,3,6-trimethylphenol], 4,4'-[(2-hydroxyphenyl)methylene]bis[2-cyclohexyl-5-methylphenol], 4,4'-[(4-hydroxyphenyl)methylene]bis[2-cyclohexyl-5-methylphenol], 4,4'-[(3-methoxy-4-hydroxyphenyl)methylene]bis[2-cyclohexyl-5-methylphenol], 4,4'-[(3,4-dihydroxyphenyl)methylene]bis[2-methylphenol], 4,4'-[(3,4-dihydroxyphenyl)methylene]bis[2,6-dimethylphenol], 4,4'-[(3,4-dihydroxyphenyl)methylene]bis[2,3,6-trimethylphenol], 4-[bis(3-cyclohexyl-4-hydroxy-6-methylphenyl)methyl]-1,2-benzenediol, 4,4',4'',4'''-(1,2-ethanediylidene)tetrakisphenol, 4,4',4'',4'''-(1,2-ethanediylidene)tetrakis[2-methylphenol], 4,4',4'',4'''-(1,2-ethanediylidene)tetrakis[2,6-dimethylphenol], 4,4',4',4'''-(1,4-phenylenedimethylidene)tetrakisphenol, 4,4',4'',4'''-(1,4-phenylenedimethylidene)tetrakis(2,6-dimethylphenol), 4,4'-[(2-hydroxyphenyl)methylene]bis[3-methylphenol], 4,4'-[(2-hydroxy-3-methoxyphenyl)methylene]bis[2,5-dimethylphenol], 4,4'-[(2-hydroxy-3-methoxyphenyl)methylene]bis[2,6-dimethylphenol], 2,2'-[(2-hydroxy-3-methoxyphenyl)methylene]bis[3,5-dimethylphenol], 4,4'-[(2-hydroxyphenyl)methylene]bis[2-methylethylphenol], 4,4'-[(4-hydroxyphenyl)methylene]bis[2-methylethylphenol]2,2'-[(4-hydroxyphenyl)methylene]bis[3,5,6-trimethylphenol], 2,2'-[(4-hydroxy-3-ethoxyphenyl)methylene]bis[3,5-dimethylphenol], 4,4'-[(2-hydroxy-3-methoxyphenyl)methylene]bis[2-(methylethyl)phenol], 4,4'-[(4-hydroxy-3-methoxyphenyl)methylene]bis[2-(methylethyl)phenol], 2,2'-[(2-hydroxy-3-methoxyphenyl)methylene]bis[3,5,6-trimethylphenol], 2,2'-[(4-hydroxy-3-methoxyphenyl)methylene]bis[3,5,6-trimethylphenol], 4,4'-[(4-hydroxy-3-ethoxyphenyl)methylene]bis[2-(methylethyl)phenol], 2,2'-[(4-hydroxy-3-ethoxyphenyl)methylene]bis[3,5,6-trimethylphenol], 4,4'-[(4-hydroxy-3-ethoxyphenyl)methylene]bis[2,3,6-trimethylphenol], 4,4'-[(4-hydroxy-3-methoxyphenyl)methylene]bis[2-(1,1-dimethylethyl)-5-methylphenol], 4,4'-[(2-hydroxyphenyl)methylene]bis[2-cyclohexylphenol], 4,4'-[(4-hydroxyphenyl)methylene]bis[2-cyclohexylphenol], 4,4'-[(2-hydroxy-3-methoxyphenyl)methylene]bis[2-cyclohexylphenol], 4,4'-[(4-hydroxy-3-ethoxyphenyl)methylene]bis[2-(1,1-dimethylethyl)-6-methylphenol], 4,4'-[(4-hydroxy-3-ethoxyphenyl)methylene]bis[2-cyclohexyl-5-methylphenol], 4,4',4''-methylidenetris[2-cyclohexyl-5-methylphenol], 2,2'-[(3,4- dihydroxyphenyl)methylene]bis[3,5-dimethylphenol], 4,4'-[(3,4-dihydroxyphenyl)methylene]bis[2-(methylethyl)phenol], 2,2'-[(3,4-dihydroxyphenyl)methylene]bis[3,5,6-trimethylphenol], 4,4'-[(3,4-dihydroxyphenyl)methylene]bis[2-cyclohexylphenol], 3,3'-[(2-hydroxyphenyl)methylene]bis[5-methylbenzene-1,2-diol], 4,4'-[4-[[bis(4-hydroxy-2,5-dimethylphenyl)methyl]phenyl]methylene]bis[1,3-benzenediol], 4,4'-methylenebis[2-[di(4-hydroxy-3-methylphenyl)]methyl]phenol, 4,4'-methylenebis[2-[di(4-hydroxy-2,5-dimethylphenyl)]methyl]phenol, 4,4'-methylenebis[2-[di(4-hydroxy-3,5-dimethylphenyl)]methyl]phenol, 4,4'-methylenebis[2-[di(3-cyclohexyl-4-hydroxy-6-methylphenyl)]methyl]phenol, and 4,4'-(3,5-dimethyl-4-hydroxyphenylmethylene)-bis(2,6-dimethylphenol). Such a hydroxyl group-containing compound having a triarylmethane skeleton is particularly preferable because of high thermal coloring temperature and high heat resistance. These may be used alone or in combination of two or more. The hydroxyl group-containing compound having a triarylmethane skeleton may be used as a quinonediazide compound by ester-bonding sulfonic acid of naphthoquinonediazide to the compound.

The content of the heat chromogenic compound in the resin composition of the present invention is preferably from 5 to 80 parts by weight, more preferably from 10 to 60 parts by weight, based on 100 parts by weight of the resin. When the content is 5 parts by weight or more, the transmittance of the heat resistance coating film in an ultraviolet-visible light region can be lowered. On the other hand, when the content is 80 parts by weight or less, the heat resistance and strength of the heat resistance coating film can be maintained and the water absorption rate can be reduced.

The resin composition of the present invention may contain a dye and/or an organic pigment. Examples of the use method include a method of using one type of dye or organic pigment, a method of using a mixture of two or more types of dyes or organic pigments, and a method of using a combination of one or more types of dyes and one or more types of organic pigments. In the present invention, a dye and/or an organic pigment having an absorption maximum at 436 to 750 nm is preferably selected.

The dye used in the present invention is preferably one soluble in an organic solvent that dissolves the resin of the present invention and compatible with the resin. Dyes having high heat resistance and light resistance are preferred. Preferred examples of the dyes include oil-soluble dyes, disperse dyes, reactive dyes, acid dyes, and direct dyes. Examples of the skeleton structure of the dye include anthraquinone type, azo type, phthalocyanine type, methine type, oxazine type, quinoline type, and triarylmethane type, and these dyes may be used alone or as metal-containing complex salt dyes. Specifically, examples of such dyes include, but are not limited to, Sumilan Dyes and Lanyl Dyes (produced by Sumitomo Chemical Industry Co., Ltd.); Orasol Dyes, Oracet Dyes, Filamid Dyes, and Irgasperse Dyes (produced by Ciba Specialty Chemicals Co., Ltd.); Zapon Dyes, Neozapon Dyes, Neptune Dyes, and Acidol Dyes (produced by BASF); Kayaset Dyes and Kayakalan Dyes (produced by Nippon Kayaku Co., Ltd.); Valifast Colors Dyes (produced by Orient Chemical Co., Ltd.); Savinyl Dyes, Sandoplast Dyes, Polysynthren Dyes, and Lanasyn Dyes (Produced by Clariant Japan Co., Ltd.); Aizen Spilon Dyes (produced by Hodogaya Chemical Co., Ltd.); functional dyes (produced by Yamada Chemical Co., Ltd.); and Plast Color Dyes and Oil Color Dyes (produced by Arimoto Chemical Co., Ltd.). These dyes may be used alone or in combination of two or more.

The organic pigment used in the present invention is preferably a pigment having high heat resistance and light resistance. Specific examples of the organic pigment used in the present invention are indicated by color index (CI) numbers. Examples of violet pigments include Pigment Violets 19, 23, 29, 32, 33, 36, 37, and 38. Examples of blue pigment include Pigment Blues 15 (15:3, 15:4, 15:6 etc.), 21, 22, 60, and 64. Examples of green pigment include Pigment Greens 7, 10, 36, and 47. Pigments other than these pigments can also be used.

The content of the organic pigment in the resin composition of the present invention is preferably from 1 to 300 parts by weight, more preferably from 10 to 200 parts by weight, based on 100 parts by weight of the resin. If the amount used is 1 part by weight or more, light of a corresponding wavelength can be absorbed. By setting the amount to 300 parts by weight or less, it is possible to absorb the light of the corresponding wavelength while maintaining adhesion strength between the resin film and the substrate and the heat resistance and mechanical properties of the heat resistance coating film after heat treatment.

As the organic pigment used in the present invention, if necessary, there may be used one which is subjected to surface treatment such as rosin treatment, acidic group treatment, and basic group treatment. In addition, the organic pigment can be used together with a dispersant as the case may be. Examples of the dispersant include cationic, anionic, nonionic, amphoteric, silicone, and fluorine surfactants.

The resin composition of the present invention may contain inorganic particles, and the resin film and the heat resistance coating film after heat treatment can be made into highly elastic and tough films. Preferred examples of inorganic particles include silicon dioxide, titanium dioxide, and alumina, but are not limited thereto.

The resin composition of the present invention can be obtained by putting the above-mentioned resin, if necessary, solvent and other additives in a glass flask or a stainless steel container and mixing the resultant by a method of stirring and dissolving the resultant with a mechanical stirrer or the like, a method of dissolving the resultant with ultrasonic waves, a method of stirring and dissolving the resultant by means of a planetary stirring and defoaming apparatus, or the like. Conditions of stirring and mixing are not particularly limited. The viscosity of the resultant resin composition is preferably 1 to 10,000 mPa·s. In order to remove foreign bodies, the resin composition may be filtered with a filter having a pore size of 0.01 μm to 5 μm. A filtration filter may be formed of polypropylene (PP), polyethylene (PE), nylon (NY), polytetrafluoroethylene (PTFE) or the like, with polyethylene and nylon being preferred. When the resin composition contains an organic pigment, it is preferable to use a filtration filter having a larger pore size than the particle sizes of the pigment.

The resin composition of the present invention can be pattern-formed through a process of coating the resin composition onto a support substrate to form a coating film, a process of drying the coating film to form a resin film, a process of exposing the resin film, a process of developing the exposed resin film, and a process of applying heat treatment to the developed resin film.

First, the resin composition is coated onto a support substrate. As the substrate, a silicon wafer, ceramics, gallium arsenide, metal, glass, a metal oxide insulating film, silicon nitride, ITO, IZO, amorphous silicon, microcrystalline silicon, polysilicon, IGZO, or the like are used, but is not limited thereto.

Examples of the coating method include spin coating using a spinner, spray coating, roll coating, slit die coating, ink-jet coating, or a combination thereof. Although the thickness of the coating film is different depending on the coating method, the solid content concentration of the resin composition, the viscosity and the like, the resin composition is generally applied so that the film thickness after drying is 0.1 to 150 μm. In particular, when the substrate is a rectangular large-sized substrate, in terms of film thickness uniformity of the coating film, slit die coating or a method in which coating is carried out while rotating the substrate after slit die coating is preferably used.

Then, the substrate coated with the resin composition is dried to obtain a resin film. Drying is preferably carried out using an oven, a hot plate, infrared light or the like, in a range of 50° C. to 150° C. for 1 minute to several hours. If necessary, the substrate can also be dried in two or more stages, such as 2 minutes at 80° C. and 2 minutes at 120° C. Although the pressure during drying may be normal pressure, in terms of film thickness uniformity of the resin film after drying, a process of first drying under reduced pressure and then drying at normal pressure is also preferably used.

Then, the resin film is irradiated with actinic rays through a mask having a desired pattern. Examples of actinic rays used for exposure include ultraviolet light, visible light, electron beam, and X ray. In the present invention, it is preferable to use the i-line (365 nm), h-line (405 nm), or g-line (436 nm) of a mercury lamp.

When photosensitivity is not imparted to the resin composition, it is necessary to further form another photoresist coating film on the resin film. As this photoresist, a general novolak type resist such as OFPR-800 (manufactured by Tokyo Ohka Kogyou Co., Ltd.) is preferably used. The photoresist coating film is formed by a method similar to the formation of the resin composition.

When the resolution of the pattern at the time of development is improved or the allowable range of development conditions is increased, a process of carrying out a baking treatment before development may be included. The temperature is preferably in a range of 50° C. to 180° C., more preferably in a range of 60° C. to 150° C. The time is preferably from 10 seconds to several hours. Within this range, there are advantages that the reaction proceeds favorably and the development time can be shortened. In order to form a pattern of the resin composition from the resin film, development processing is performed. When the resin composition has a negative photosensitivity, a relief pattern can be obtained by removing an unexposed portion with a developer, and when the resin composition has a positive photosensitivity, the relief pattern can be obtained by removing an exposed portion with the developer.

Although a suitable developer can be selected according to the structure of the resin composition, there can be preferably used an aqueous solution of a compound showing alkalinity, such as ammonia, tetramethylammonium, diethanolamine, diethylaminoethanol, sodium hydroxide, potassium hydroxide, sodium carbonate, potassium carbonate, triethylamine, diethylamine, methylamine, dimethylamine, dimethylaminoethyl acetate, dimethylaminoethanol, dimethylaminoethyl methacrylate, cyclohexylamine, ethylenediamine, and hexamethylenediamine. As the case may be, to the alkaline aqueous solution, any one or more in combination of the following may be added: polar solvents such as N-methyl-2-pyrrolidone, N,N-dimethylformamide, N,N-dimethylacetamide, dimethylsulfoxide, γ-butyrolactone, and dimethylacrylamide, alcohols such as methanol, ethanol, and isopropanol, esters such as ethyl lactate and propyleneglycolmonomethyletheracetate, and ketones such as cyclopentanone, cyclohexanone, isobutyl ketone, and methyl isobutyl ketone.

As a developer, there can be preferably used a mixture including a combination of one or more of good solvents for the resin composition of the present invention, such as N-methyl-2-pyrrolidone, N-acetyl-2-pyrrolidone, N,N-dimethylformamide, N,N-dimethylacetamide, dimethylsulfoxide, and hexamethylphosphoramide, and poor solvents for the resin composition, such as methanol, ethanol, isopropyl alcohol, water, methyl carbitol, ethyl carbitol, toluene, xylene, ethyl lactate, ethyl pyruvate, propyleneglycolmonomethyletheracetate, methyl-3-methoxypropionate, ethyl-3-ethoxypropionate, 2-heptanone, cyclopentanone, cyclohexanone, and ethyl acetate.

Development can be carried out by a method such as coating the above developer onto a coating film surface of the resin composition as it is or spraying the developer onto the coating film surface, dipping in the developer, or applying ultrasonic waves while dipping.

Then, it is preferable to wash a relief pattern formed by development with a rinsing solution. When an alkaline aqueous solution is used as the developer, water can be preferably used as the rinsing solution. At this time, rinse treatment may be carried out with a liquid obtained by adding esters, such as ethanol, isopropyl alcohols, and propyleneglycolmonomethyletheracetate, carbonic acid gas, hydrochloric acid, or acetic acid to water.

When rinsing with an organic solvent, there are preferably used solvents having satisfactory miscibility with a developer, such as methanol, ethanol, isopropyl alcohol, ethyl lactate, ethyl pyruvate, propyleneglycolmonomethyletheracetate, methyl-3-methoxypropionate, ethyl-3-ethoxypropionate, 2-heptanone and ethyl acetate.

When the photosensitivity is not imparted to the resin composition, it is necessary to remove the photoresist coating film formed on the resin film after development. This removal is often carried out by removal by dry etching or wet etching with a peeling solvent. Examples of the pealing solvent include, but are not limited to, organic solvents such as acetone, butyl acetate, ethyl lactate, propyleneglycolmonomethyletheracetate, methyl 3-methoxypropionate, ethyl-3-ethoxypropionate, 2-heptanone, and ethylacetate and aqueous solutions of sodium hydroxide and potassium hydroxide.

When a resin which forms a cyclic structure by heating a polyimide precursor, a polybenzimidazole precursor or the like or by catalysis is used as the resin composition, in order to convert the resin into a heat resistance resin having a cyclic structure, a temperature of 150° C. to 500° C. is applied to the resin after development to convert the resin into a heat resistance coating film. The heat treatment is preferably performed by raising the temperature stepwise from a selected temperature or raising the temperature continuously in a selected temperature range for 5 minutes to 5 hours. As one example, there are a method of heat treatment at 130° C., 200° C., and 350° C. for 30 minutes each, a method of linearly raising the temperature from room temperature to 320° C. over 2 hours, and the like. There is a possibility that electric characteristics of an element change due to high temperature heating and repetition thereof, and warpage of the substrate becomes large. Therefore, the heat treatment is preferably carried out at 250° C. or less.

If the heat treatment is carried out at 250° C. or less, polyimide or polyamideimide is preferably used as a resin contained in the resin composition, and a resin having a structure represented by the general formula (4) is more preferably used. From the viewpoint of heat resistance, a polyimide resin represented by the general formula (4) is most preferable. Since the polyimide resin represented by the general formula (4) already has a cyclic structure, it is not necessary to carry out dehydration and ring closure by raising the heat treatment temperature to a high temperature, so that the biggest advantage is that heat treatment at a low temperature of 250° C. or less becomes possible.

Residual stress attributable to the resin forming the heat resistance coating film of a substrate with the heat resistance coating film obtained by the above-described manufacturing method is preferably 30 MPa or less. The residual stress is more preferably 25 MPa or less, and most preferably 15 MPa or less. If the residual stress attributable to the resin is large, the yield may deteriorate during a process of manufacturing a device including the substrate with the heat resistance coating film, or the reliability of products may become poor.

The heat resistance coating film formed from the resin composition of the present invention can be used for electronic components such as semiconductor devices and multilayer wiring boards. Specifically, the heat resistance coating film is preferably used for applications such as a passivation film of a semiconductor, a surface protective film of a semiconductor element, an interlayer insulating film, an interlayer insulating film of multilayer wiring for high density mounting, an insulating layer of an organic electroluminescent element, a flattening film of a thin film transistor substrate, and an interlayer insulating film of a thin film transistor, but the application is not limited thereto. The heat resistance coating film can have various structures. When the resin composition contains a conductive filler, the heat resistance coating film can also be used as a wiring material.

Next, an application example to a semiconductor device with bumps using the resin composition of the present invention will be described with reference to the drawings. FIG. 1 is an enlarged cross-sectional view of a pad portion of a semiconductor device with bumps according to the present invention. As shown in FIG. 1, a passivation film 3 is formed on an input/output Al pad 2 on a silicon wafer 1, and the passivation film 3 has via holes. Further, a pattern (insulating film) 4 according to the resin composition of the present invention is formed on the passivation film 3. Furthermore, a metal (Cr, Ti, Ni, TiW, etc.) film 5 and a metal (Cu, Au, etc.) wiring 6 are sequentially formed so as to be connected to the Al pad 2, and an insulating film 7 as a second insulating film is formed thereon. In the insulating film 7, a periphery of a solder bump 10 is opened to insulate each pad. A barrier metal 8 and a solder bump 10 are formed on the insulated pad. When the resin composition of the present invention is introduced, since warpage of the wafer is small, exposure and wafer transfer can be carried out with high accuracy. Since the resin of the present invention is excellent in mechanical properties, stress from a sealing resin can be relaxed during mounting, so that it is possible to provide a highly reliable semiconductor device which prevents damage of a low-k layer.

Figure 2:
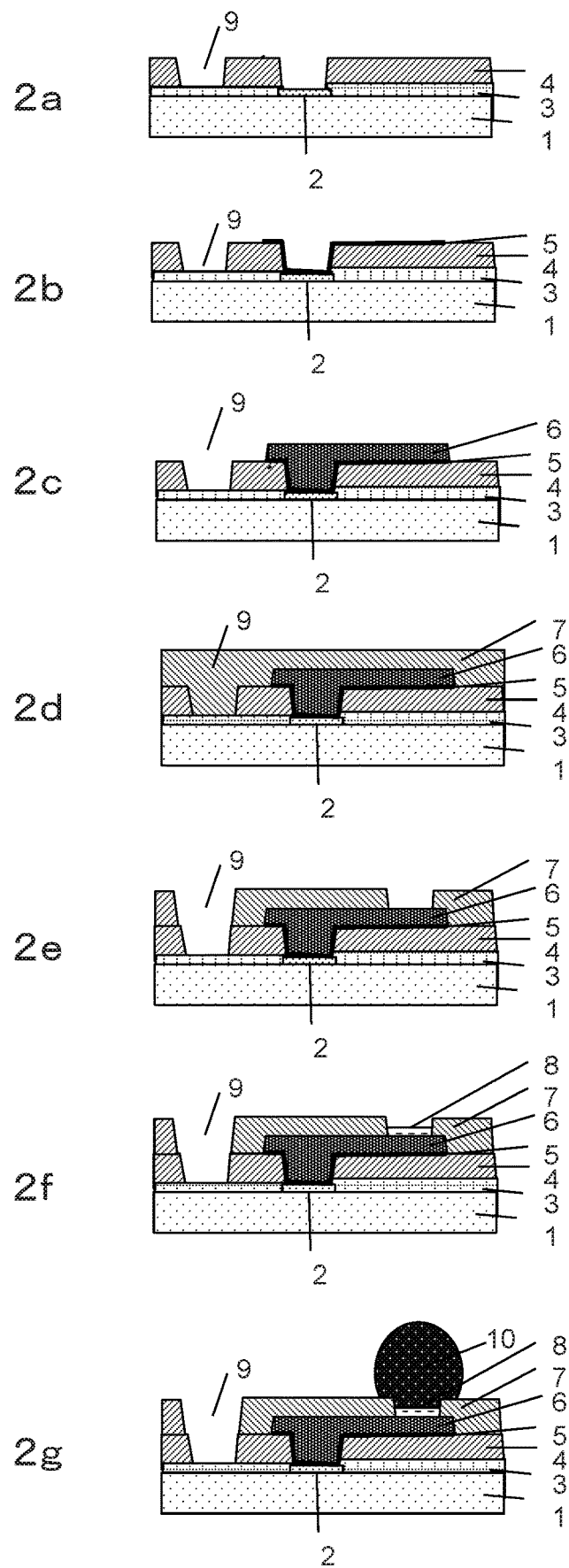
FIG. 2 is a view showing a detailed method for producing the semiconductor device having the bump.

Next, a detailed method for producing a semiconductor device with bumps will be described with reference to FIG. 2. In FIG. 2a, the resin composition of the present invention is coated, and the insulating film 4 is formed through a photolithography process. Then, in FIG. 2b, the metal film 5 is formed by a sputtering method, and in FIG. 2c, the metal wiring 6 is formed by a plating method. Then, in FIG. 2d, the resin composition of the present invention is coated again, and the insulating film 7 as shown in FIG. 2e is formed through a photolithography process. When a multilayer wiring structure including three or more layers is formed, each layer can be formed by repeating the above process.

Then, as shown in FIGS. 2f and 2g, the barrier metal 8 and the solder bump 10 are formed. Finally, dicing is carried out along the scribe line 9, by which each chip is cut. If stress attributable to the resin is low in this series of production processes, warpage of the substrate can be reduced, which is extremely preferable because it loads to improvement in yield and reliability of the semiconductor device.

Figure 3:
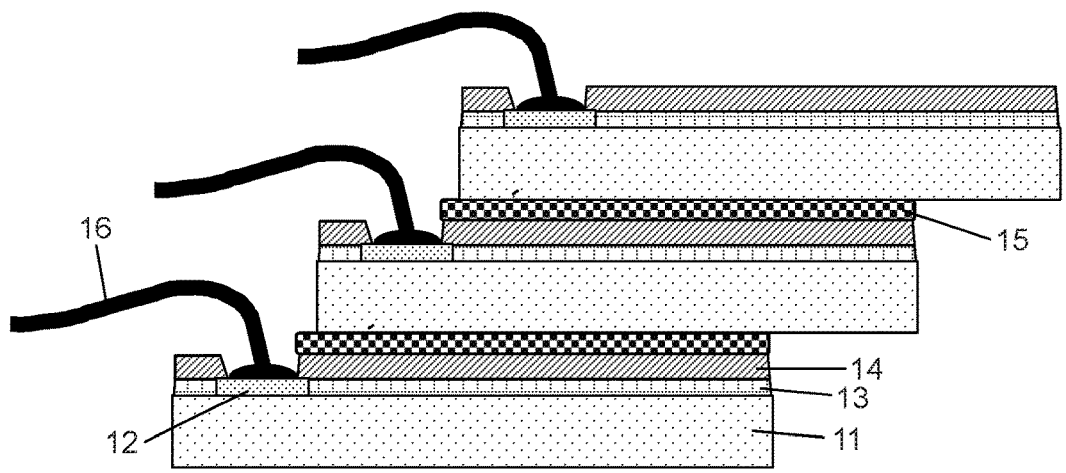
FIG. 3 is an enlarged cross-sectional view of an electrode portion of a chip stacked type semiconductor device.
Figure 4:
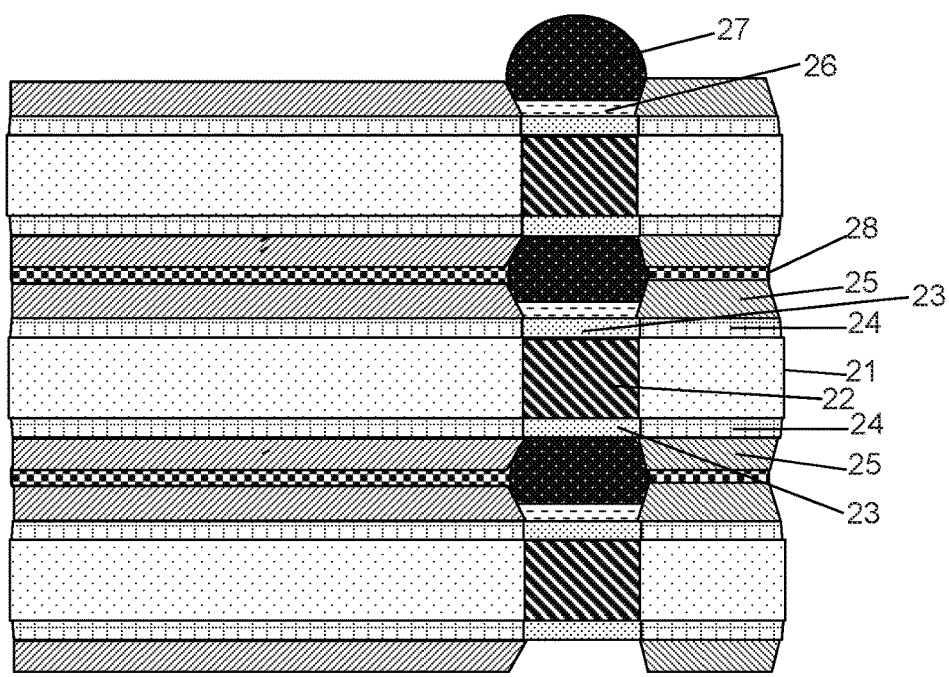
FIG. 4 is an enlarged cross-sectional view of an electrode portion of a chip stacked type semiconductor device.

Next, an application example to a chip stacked type semiconductor device using the resin composition of the present invention will be described with reference to the drawings. FIGS. 3 and 4 are enlarged cross-sectional views of electrode portions of the chip stacked type semiconductor device of the present invention. As shown in FIG. 3, a passivation film 13 is formed on an input/output Al pad 12 on a silicon wafer 11, and the passivation film 13 has via holes. Further, a pattern (insulating film) 14 according to the resin composition of the present invention is formed on the passivation film 13, these chips are stacked in multiple layers via an adhesive film 15 such as a die attach film, and the Al pad is connected to an external terminal via a wire (Cu, Au, etc.) 16. As shown in FIG. 4, a through electrode 22 is formed in a silicon wafer 21, passivation films 24 are formed on input/output pads (Al, Cu, etc.) 23 at both ends of the through electrode 22, and a via hole is formed in the passivation film 24. Moreover, a pattern (insulating film) 25 according to the resin composition of the present invention is formed thereon, and a barrier metal 26 and a solder bump 27 are sequentially formed. These chips are vertically stacked via an adhesive film 28 such as a die attach film. When the resin composition of the present invention is introduced, since warpage of the wafer is small, exposure and wafer transfer can be carried out with high accuracy. Since the resin of the present invention is excellent in mechanical properties, stress from a sealing resin can be relaxed during mounting, so that it is possible to provide a highly reliable semiconductor device which prevents damage of a low-k layer.

Figure 5:
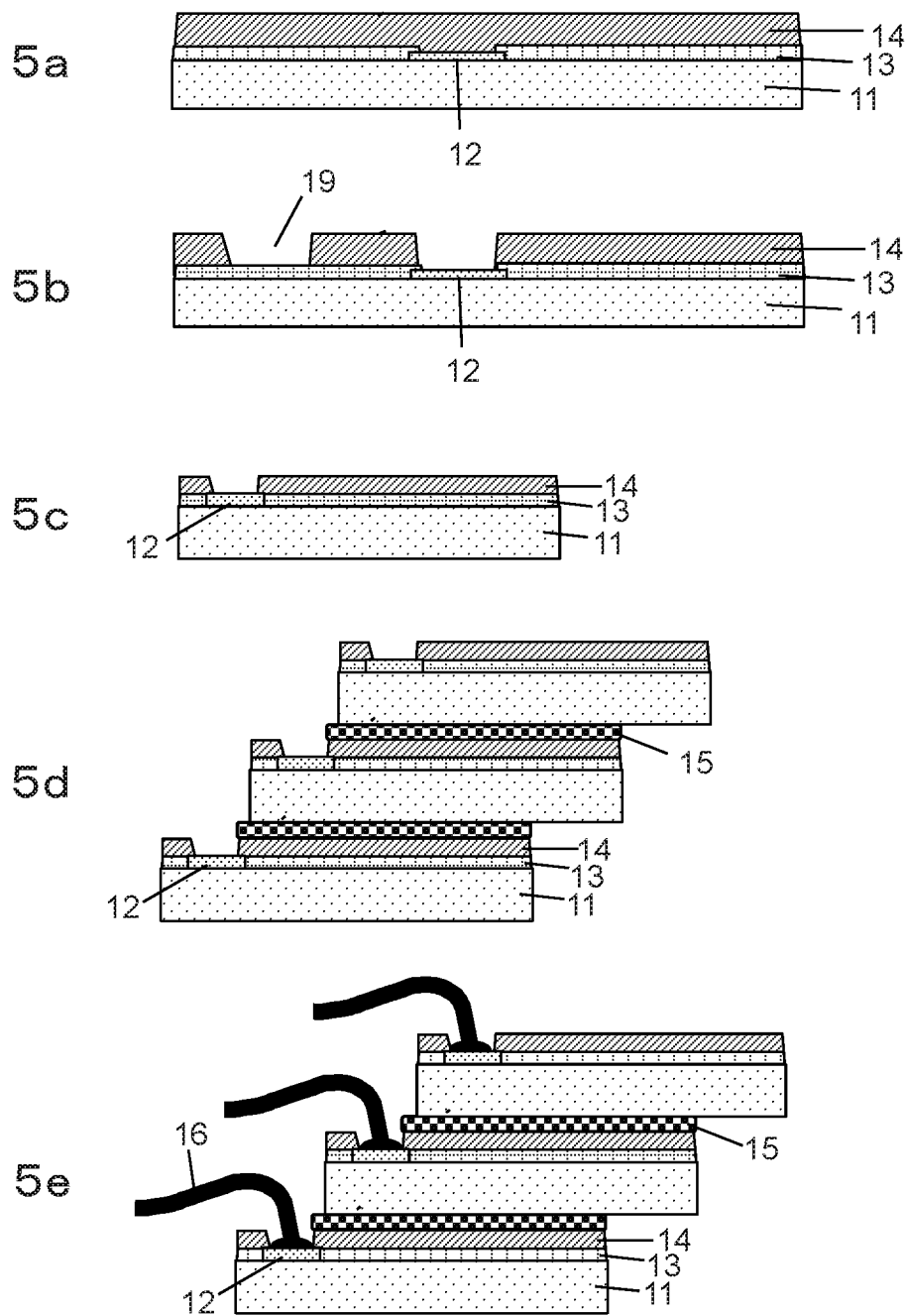
FIG. 5 is a view showing a detailed method for producing the chip stacked type semiconductor device.
Figure 6:
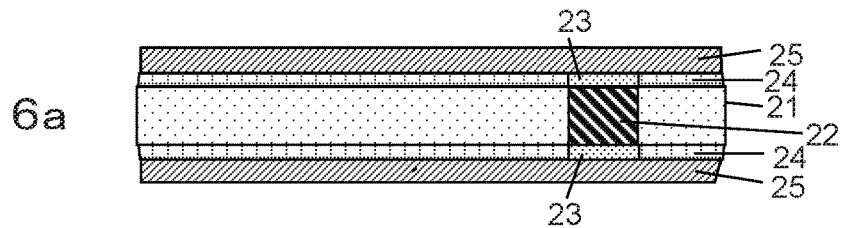
FIG. 6 is a view showing a detailed method for producing the chip stacked type semiconductor device.
Figure 6:
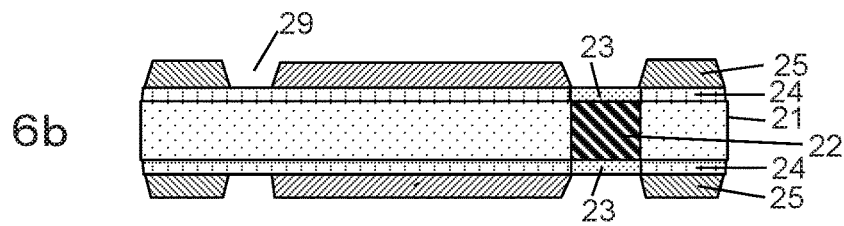
Figure 6:
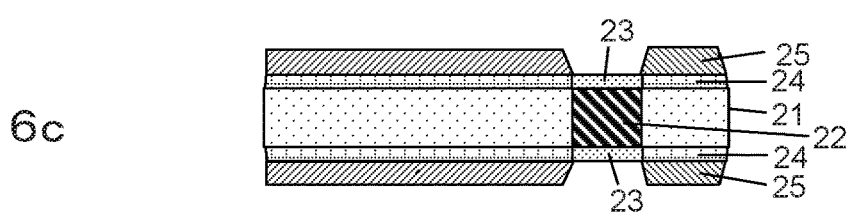
Figure 6:
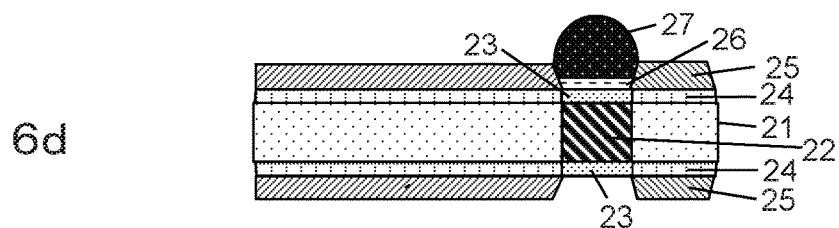
Figure 6:
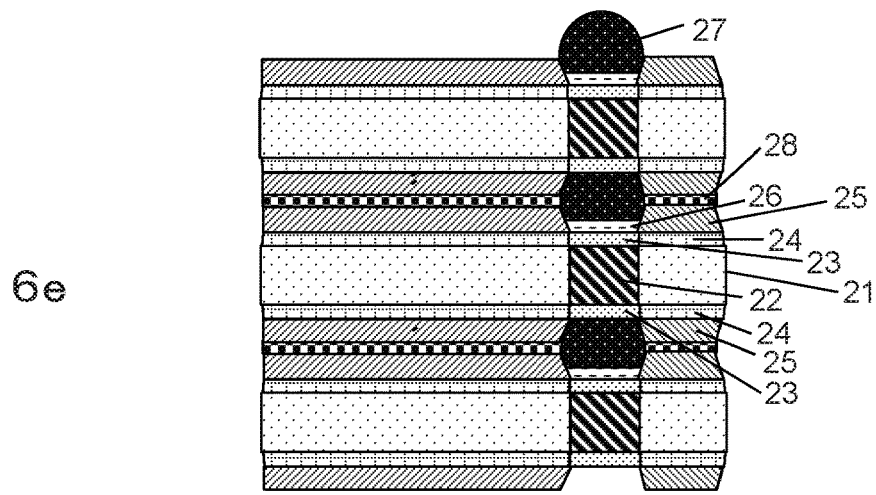

Next, a detailed method for producing a chip stacked type semiconductor device will be described with reference to FIGS. 5 and 6. In FIG. 5a, the resin composition of the present invention is applied onto a device substrate with a pad, and a pattern (insulating film 14) as shown in FIG. 5b is formed through a photolithography process. Then, if necessary, the substrate is ground and thinned, diced along the scribe line 9 in FIG. 5c, and cut for each chip. In FIG. 5d, the cut and divided chips are stacked via the adhesive films 15 such that the pads are exposed. In FIG. 5e, an exposed electrode is connected to the outside via a wire. If stress attributable to the resin is low in this series of production processes, warpage of the substrate can be reduced, which is extremely preferable because it leads to improvement in yield and reliability of the semiconductor device.

As shown in FIG. 6a, the resin composition of the present invention is applied onto a through electrode and a device substrate with a pad, and a pattern (insulating film 25) as shown in FIG. 6b is formed through a photolithography process. Then, as shown in FIG. 6c, dicing is carried out along a scribe line 29, by which each chip is cut. Then, as shown in FIG. 6d, a barrier metal 26 and a solder bump 27 are formed. As shown in FIG. 6e, the cut and divided chips are stacked via an adhesive film 28 so that the through electrodes are vertically aligned. If stress attributable to the resin is low in this series of production processes, warpage of the substrate can be reduced, which is extremely preferable because it leads to improvement in yield and reliability of the semiconductor device.

Figure 7:
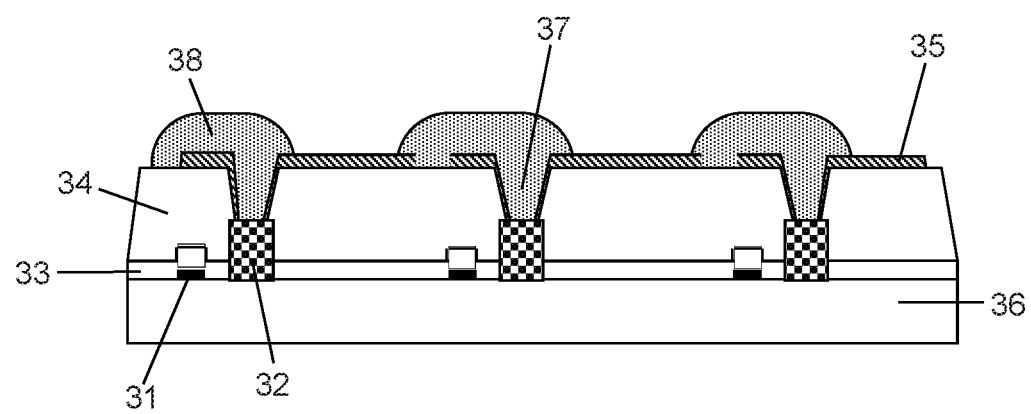
FIG. 7 is a cross-sectional view of a TFT substrate.

The heat resistance coating film obtained from the resin composition of the present invention is suitably used as a flattening film of a display device having a substrate on which a TFT (Thin Film Transistor) is formed, a flattening film, and a display element in this order. Examples of the display device having such a configuration include a liquid crystal display device and an organic EL display device. An active matrix type display device has a TFT and a wiring located at a side portion of the TFT and connected to the TFT on a substrate such as glass or various plastics and has a flattening film thereon to cover concavoconvexes, and a display element is further provided on the flattening film. The display element and the wiring are connected via a contact hole formed in the flattening film. FIG. 7 shows a cross-sectional view of a TFT substrate. TFTs 31 of a bottom gate type or a top gate type are provided in rows and columns on a substrate 36, and an insulating film 33 is formed so as to cover the TFTs 31. On the insulating film 33, a wiring 32 connected to the TFT 31 is provided. Further, on the insulating film 33, a flattening film 34 is provided in a state of embedding the wiring 32. In the flattening film 34, a contact hole 37 reaching the wiring 32 is provided. An ITO (transparent electrode) 35 is formed on the flattening film 34 in a state of being connected to the wiring 32 via the contact hole 37. Here, the ITO 35 serves as an electrode of a display element (for example, an organic EL element). This organic EL element may be of a top emission type which emits emitted light from the side opposite to the substrate 36 or a bottom emission type which extracts light from the substrate 36 side, and is preferably of the top emission type. In this manner, an active matrix type organic EL display device in which TFTs 31 for driving the organic EL elements are connected to each organic EL element is obtained.

Next, a 5,5'-dihydroxyl-4,4'-diaminobiphenyl derivative represented by the following general formula (10) in the present invention will be explained.

[Chemical Formula 20]

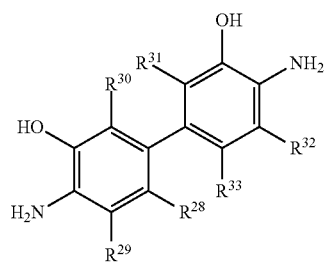

(10)

In the above general formula (10), $R^{28}$ and $R^{33}$ are the same and each independently one kind selected from the group consisting of a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. $R^{29}$ and $R^{32}$ are the same, $R^{30}$ and $R^{31}$ are the same, and they are one kind selected from the group consisting of hydrogen, halogen, a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. One or more substituents among them may be the same or different and are one or more of halogen, trifluoromethyl, trimethylsilyl, a $C_1$ to $C_6$ alkoxyl group, a $C_1$ to $C_6$ alkyl group, an arylalkoxyl group, a $C_6$ to $C_{30}$ aryl group, and a $C_4$ to $C_{30}$ heterocyclic group.

In $R^{28}$ and $R^{33}$ described above, the substituted or unsubstituted $C_1$ to $C_6$ alkyl group is preferably a $C_1$ to $C_6$ linear alkyl group, a $C_1$ to $C_6$ side chain alkyl group or a $C_1$ to $C_6$ cycloalkyl group, more preferably methyl, trifluoromethyl, ethyl, trifluoroethyl, n-propyl, isopropyl, n-butyl, sec-butyl, t-butyl, n-pentyl, isopentyl, neopentyl, n-hexyl, cyclohexyl or the like. The substituted or unsubstituted $C_1$ to $C_6$ alkoxyl group is preferably a $C_1$ to $C_6$ linear alkyl group, a $C_1$ to $C_6$ side chain alkyl group or a $C_1$ to $C_6$ cycloalkyl group, which is bound by an ether group, more preferably methoxy, trifluoromethoxy, ethoxy, n-propoxy, isopropoxy, n-butoxy, sec-butoxy, t-butoxy, n-pentyloxy, n-hexyloxy or cyclohexyloxy. The halogenated alkyl group is preferably trifluoromethyl, trifluoroethyl, trichloromethyl, trichloroethyl, tribromomethyl, tribromoethyl, triiodomethyl or the like, more preferably trifluoromethyl or trifluoroethyl. The substituted or unsubstituted amino group is preferably a primary amino group, secondary amino group or tertiary amino group, the amino group can be substituted by one or two groups, and substituents may be the same or different. A $C_1$ to $C_6$ alkyl group, a $C_6$ to $C_{30}$ aryl group or a $C_6$ to $C_{30}$ heteroaryl group is preferred, and an amino group, methylamino, ethylamino, dimethylamino, phenylamino, benzylamino, pyridinamino or furanylamino is more preferred. The substituted or unsubstituted amide group is preferably an alkylamido group, an arylamido group, an alkoxyamido group or the like. Among them, the substituent may be connected to a carbonyl group or an amino group, and formamide, acetamide, benzamide, t-butoxyamide, benzyloxycarbonylamino, propylacetamide, acetanilide, or the like is more preferred. The substituted or unsubstituted $C_6$ to $C_{30}$ aryl group is preferably a substituted or unsubstituted aromatic hydrocarbon group such as a phenyl group, a naphthyl group, an anthracenyl group, a phenanthryl group, a pyrenyl group, a biphenyl group, or a terphenyl. The substituted or unsubstituted $C_4$ to $C_{30}$ heterocyclic aryl group is preferably a furanyl group or a pyridine group, and the ester group is an alkoxylcarbonate ester group, among which the alkoxyl group is not particularly limited, and methoxycarbonate ester, ethoxycarbonate ester, propoxycarbonate ester, butoxycarbonate ester, t-butoxycarbonate ester, benzyloxycarbonate ester, fluorenylmethoxy carbonate ester and the like are preferred.

In $R^{29}$, $R^{30}$, $R^{31}$ and $R^{32}$ described above, the halogen is preferably fluoro, chloro or iodo, and the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In the substituent, the halogen is preferably fluoro, chloro or iodo. The $C_1$ to $C_6$ alkoxy group is preferably a $C_1$ to $C_6$ linear alkyl group, a $C_1$ to $C_6$ side chain alkyl group or a $C_1$ to $C_6$ cycloalkyl group, which is bound by an ether group, more preferably methoxy, trifluoromethoxy, ethoxy, n-propoxy, isopropoxy, n-butoxy, sec-butoxy, t-butoxy, n-pentyloxy, n-hexyloxy or cyclohexyloxy. The $C_1$ to $C_6$ alkyl group is preferably a $C_1$ to $C_6$ linear alkyl group, a $C_1$ to $C_6$ side chain alkyl group or a $C_1$ to $C_6$ cycloalkyl group, more preferably methyl, trifluoromethyl, ethyl, trifluoroethyl, n-propyl, isopropyl, n-butyl, sec-butyl, t-butyl, n-pentyl, isopentyl, neopentyl, n-hexyl, cyclohexyl or the like. The arylalkoxy group is preferably benzyloxy, naphthylmethoxy, anthracenylmethoxy, fluorenylmethoxy, 3,5-di t-butylphenyl-1-isopropoxy, phenylethoxy, naphthylethoxy, benzidine-3-methoxy or the like, more preferably benzyloxy or fluorenylmethoxy.

The $C_6$ to $C_{30}$ aryl group is preferably a substitutable aromatic hydrocarbon group such as a phenyl group, a naphthyl group, an anthracenyl group, a phenanthryl group, a pyrenyl group, a biphenyl group, or a terphenyl, and the $C_4$ to $C_{30}$ heteroaryl group is preferably a pyridine group, a carbazoyl group, an imidazole group, a furanyl group, a thiophene group, an oxazole group, an indolyl group, a benzofuranyl group or a benzothiophene group.

In $R^{29}$, $R^{30}$, $R^{31}$ and $R^{32}$ described above, $R^{29}$, $R^{30}$, $R^{31}$ and $R^{32}$ are preferably hydrogen.

The present invention further describes a process for producing a 5,5'-dihydroxyl-4,4'-diaminobiphenyl derivative. First, a 5,5'-dibromo-4,4'-diaminobiphenyl derivative represented by the general formula (12) is obtained by bromination reaction of a 4,4'-diaminobiphenyl derivative represented by the general formula (11).

[Chemical Formula 21]

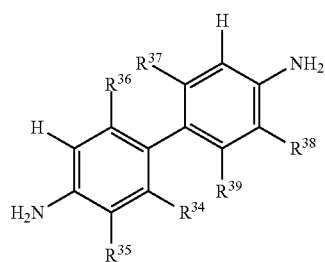
(11)

[Chemical Formula 22]

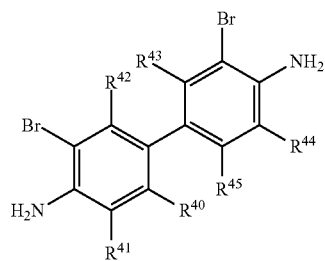
(12)

In the above general formula (11), $R^{34}$ and $R^{39}$ are the same and each independently one kind selected from the group consisting of a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. $R^{35}$ and $R^{38}$ are the same, $R^{36}$ and $R^{37}$ are the same, and they are each independently one kind selected from the group consisting of hydrogen, halogen, a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group.

In the above general formula (12), $R^{40}$ and $R^{45}$ are the same and each independently one kind selected from the group consisting of a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. $R^{41}$ and $R^{44}$ are the same, $R^{42}$ and $R^{43}$ are the same, and they are each independently one kind selected from the group consisting of hydrogen, halogen, a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group.

The substituents may be the same or different and each independently represent one or more of halogen, trifluoromethyl, trimethylsilyl, a $C_1$ to $C_6$ alkoxyl group, a $C_1$ to $C_6$ alkyl group, an aryl alkoxyl group, a $C_6$ to $C_{30}$ aryl group, and a $C_4$ to $C_{30}$ heterocyclic group.

In $R^{34}$ and $R^{39}$, $R^{40}$ and $R^{45}$ described above, the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In $R^{35}$, $R^{36}$, $R^{37}$, $R^{38}$, $R^{41}$, $R^{42}$, $R^{43}$ and $R^{44}$ described above, the halogen is preferably fluoro, chloro or iodo. The substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In the substituent described above, the halogen, the substituted or unsubstituted $C_1$ to $C_6$ alkoxy group, the substituted or unsubstituted $C_1$ to $C_6$ alkyl group, the arylalkoxy group, the $C_6$ to $C_{30}$ aryl group, and the $C_4$ to $C_{30}$ heterocyclic groups are all the same as those described above.

In the above production process, it is preferable that $R^{35}$, $R^{36}$, $R^{37}$ and $R^{38}$ are hydrogen, and $R^{41}$, $R^{42}$, $R^{43}$ and $R^{44}$ are hydrogen.

A reaction solvent used for the above bromination reaction is preferably an aprotic organic solvent, and one or more of the mixed solvents of methyl acetate, ethyl acetate, propyl acetate, butyl acetate, ethylene glycol dimethyl ether, tetrahydrofuran, 1,4-dioxane and the solvent are more preferred.

A brominated solvent used for the bromination reaction is preferably liquid bromine or NBS. In the bromination reaction process, the reaction temperature is preferably from −30° C. to 60° C., more preferably from −20° C. to 60° C. The reaction time is preferably from 1 h to 48 h, and more preferably from 1 h to 12 h from the viewpoints of reaction rate and industrialization cost.

In the present invention, an amidation reaction of a 5,5'-dibromo-4,4'-diaminobiphenyl derivative represented by the general formula (12) obtained by the above production process is carried out using acid anhydride or acyl chloride, whereby a 5,5'-dibromo-4,4'-diamidobiphenyl derivative represented by the general formula (13) is further obtained.

[Chemical Formula 23]

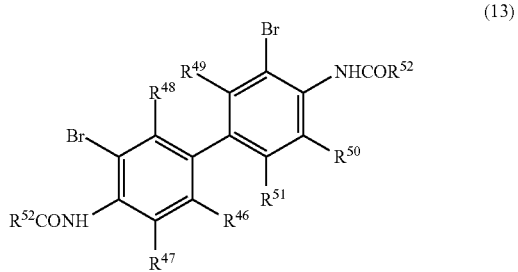

(13)

In the above general formula (13), $R^{46}$ and $R^{51}$ are the same and each independently one kind selected from the group consisting of a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. $R^{47}$ and $R^{50}$ are the same, $R^{48}$ and $R^{49}$ are the same, and they are each independently one kind selected from the group consisting of hydrogen, halogen, a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. Among them, the substituents may be the same or different and each independently represent one or more of halogen, trifluoromethyl, trimethylsilyl, a $C_1$ to $C_6$ alkoxyl group, a $C_1$ to $C_6$ alkyl group, an aryl alkoxyl group, a $C_6$ to $C_{30}$ aryl group, and a $C_4$ to $C_{30}$ heterocyclic group, and $R^{52}$ is one kind selected from the group consisting of a substituted or unsubstituted $C_1$ to $C_6$ alkyl group or a substituted or unsubstituted aryl group. The substituent in $R^{52}$ is one or more of a methyl group, a sulfo group, a fluorine atom, an amino group, and a methoxy group.

In $R^{46}$ and $R^{51}$ described above, the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In $R^{47}$, $R^{48}$, $R^{49}$ and $R^{50}$ described above, the halogen is preferably fluoro, chloro or iodo, and the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In the substituent described above, the halogen, the $C_1$ to $C_6$ alkoxy group, the $C_1$ to $C_6$ alkyl group, the arylalkoxy group, the $C_6$ to $C_{30}$ aryl group, and the $C_4$ to $C_{30}$ heterocyclic groups are all the same as those described above.

In $R^{52}$ described above, the substituted or unsubstituted $C_1$ to $C_6$ alkyl group is preferably a substituted or unsubstituted $C_1$ to $C_6$ linear alkyl group, a $C_1$ to $C_6$ side chain alkyl group or a $C_1$ to $C_6$ cycloalkyl group, more preferably methyl, trifluoromethyl, ethyl, trifluoroethyl, n-propyl, isopropyl, n-butyl, sec-butyl, t-butyl, n-pentyl, isopentyl, neopentyl, n-hexyl, cyclohexyl or the like. The substituent of $R^{52}$ is more preferably one or more of a methyl group, a sulfo group, a fluorine atom, an amino group and a methoxy group.

The substituted or unsubstituted aryl group is preferably a substituted or unsubstituted phenyl group, a substituted or unsubstituted naphthyl group, a substituted or unsubstituted anthracenyl group, a substituted or unsubstituted phenanthryl group, a substituted or unsubstituted pyrenyl group, or a substituted or unsubstituted biphenyl group. A phenyl group, p-methylphenyl, o-methylphenyl, m-methylphenyl, sulfophenyl, p-methoxyphenyl, p-fluorophenyl or the like is preferred, and the substituent of $R^{52}$ is preferably one or more of a methyl group, a sulfo group, a fluorine atom, an amino group and a methoxy group. In $R^{47}$, $R^{48}$, $R^{49}$ and $R^{50}$ described above, $R^{47}$, $R^{48}$, $R^{49}$ and $R^{50}$ are preferably hydrogen.

The acid anhydride has the general formula $(R^{52}CO)_2O$, and from the viewpoint of industrialization cost, the acid anhydride is preferably acetic anhydride, benzoic anhydride, or trifluoroacetic anhydride. The acyl chloride has the general formula $R^{52}COCl$, wherein $R_{25}$ is the same as described above, and from the viewpoint of industrialization cost, the acyl chloride is preferably acetyl chloride, propionyl chloride, hexanoyl chloride, benzoyl chloride or pivaloyl chloride.

The temperature of the amidation reaction is preferably 0° C. to 80° C., more preferably 10° C. to 40° C. A solvent of the amide reaction to be used is an aprotic solvent, more preferably tetrahydrofuran or dichloromethane. The reaction time is preferably from 1 h to 48 h, and more preferably from 1 h to 12 h from the viewpoints of reaction rate and industrialization cost.

In the present invention, the 5,5'-dibromo-4,4'-diamidobiphenyl derivative represented by the general formula (13) obtained by the above production process is reacted under the action of a catalyst and inorganic alkali, whereby a 6,6'-dibenzoxazole derivative represented by the general formula (14) is further obtained.

[Chemical Formula 24]

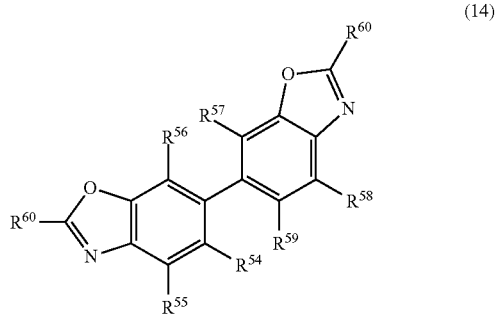

(14)

In the general formula (14), $R^{54}$ and $R^{59}$ are the same and each independently one kind selected from the group consisting of a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. $R^{55}$ and $R^{58}$ are the same, $R^{56}$ and $R^{57}$ are the same, and they are each independently one kind selected from the group consisting of hydrogen, halogen, a substituted or unsubstituted $C_1$ to $C_6$ alkyl group, a substituted or unsubstituted $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, a substituted or unsubstituted $C_4$ to $C_{30}$ heterocyclic aryl group, an ester group and a nitro group. Among them, the substituents may be the same or different and each independently represent one or more of halogen, trifluoromethyl, trimethylsilyl, a $C_1$ to $C_6$ alkoxyl group, a $C_1$ to $C_6$ alkyl group, an aryl alkoxyl group, a $C_6$ to $C_{30}$ aryl group, and a $C_4$ to $C_{30}$ heterocyclic group, and $R^{60}$ is one kind selected from the group consisting of a substitutable $C_1$ to $C_6$ alkyl group and a substitutable aryl group. The substituent in $R^{60}$ is one or more of a methyl group, a sulfo group, a fluorine atom, an amino group, and a methoxy group.

In $R^{54}$ and $R^{59}$ described above, the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In $R^{55}$, $R^{56}$, $R^{57}$ and $R^{58}$ described above, the halogen is preferably fluoro, chloro or iodo, and the substituted or unsubstituted $C_1$ to $C_6$ alkyl group, the substituted or unsubstituted $C_1$ to $C_6$ alkoxy group, the halogenated alkyl group, the substituted or unsubstituted amino group, the substituted or unsubstituted amide group, the substituted or unsubstituted $C_6$ to $C_{30}$ aryl group, the substituted or unsubstituted $C_4$ to $C_{30}$ heterocyclic aryl group, and the ester group are all the same as those described above.

In the substituent described above, the halogen, the $C_1$ to $C_6$ alkoxy group, the $C_1$ to $C_6$ alkyl group, the arylalkoxy group, the $C_6$ to $C_{30}$ aryl group, and the $C_4$ to $C_{30}$ heterocyclic groups are all the same as those described above.

In $R^{60}$ described above, the substituted or unsubstituted $C_1$ to $C_6$ alkyl group is preferably a substituted or unsubstituted $C_1$ to $C_6$ linear alkyl group, a $C_1$ to $C_6$ side chain alkyl group or a $C_1$ to $C_6$ cycloalkyl group, more preferably methyl, trifluoromethyl, ethyl, trifluoroethyl, n-propyl, isopropyl, n-butyl, sec-butyl, t-butyl, n-pentyl, isopentyl, neopentyl, n-hexyl, cyclohexyl or the like. The substituent of $R^{60}$ is more preferably one or more of a methyl group, a sulfo group, a fluorine atom, an amino group, and a methoxy group.

The substituted or unsubstituted aryl group is preferably a substituted or unsubstituted phenyl group, a substituted or unsubstituted naphthyl group, a substituted or unsubstituted anthracenyl group, a substituted or unsubstituted phenanthryl group, a substituted or unsubstituted pyrenyl group, or a substituted or unsubstituted biphenyl group. A phenyl group, p-methylphenyl, o-methylphenyl, m-methylphenyl, sulfophenyl, p-methoxyphenyl, p-fluorophenyl or the like is preferred, and the substituent of $R^{60}$ is preferably one or more of a methyl group, a sulfo group, a fluorine atom, an amino group and a methoxy group. In $R^{55}$, $R^{56}$, $R^{57}$ and $R^{58}$ described above, $R^{55}$, $R^{56}$, $R^{57}$ and $R^{58}$ are preferably hydrogen.

The catalyst contains at least a copper catalyst and may or may not contain a ligand, wherein the copper catalyst is preferably copper (I) iodide, copper (I) oxide, copper (I) acetate, or copper (I) cyanide, more preferably copper (I) iodide or copper (I) oxide, among which the ligand is preferably N,N'-dimethylethylenediamine, ethylenediamine, ethylene glycol or 1,10-o-phenanthroline, more preferably N,N'-dimethylethylenediamine, inorganic alkali in a catalytic reaction process is preferably one or more of potassium carbonate or potassium phosphate, and the reaction temperature is preferably 100° C. to 140° C.

The solvent used is preferably a high-boiling organic solvent, more preferably toluene or xylene.

In the present invention, a 5,5'-dihydroxyl-4,4'-diaminobiphenyl derivative is further obtained by a ring-opening reaction of a 6,6'-dibenzoxazole derivative, obtained by the above production process, under acidic conditions.

As the acidic condition, an inorganic strong acid is preferred, and the inorganic strong acid is preferably hydrochloric acid, sulfuric acid, acetic acid, phosphoric acid, nitric acid or formic acid, more preferably hydrochloric acid or sulfuric acid from the viewpoint of industrialization cost. The solvent used for the ring-opening reaction is a protic solvent, ethanol, methanol, isopropanol or water is preferred, and from the viewpoint of industrialization cost, ethanol or water is more preferred.

As described above, the present invention relates to a first 5,5'-dihydroxyl-4,4'-diaminobiphenyl derivative and industrial production process thereof, the production yield of the production process is high, the post-treatment is simple, and the production cost is low. The 5,5'-dihydroxyl-4,4'-diaminobiphenyl derivative produced according to the present invention can be used in the field of electronic materials or drug intermediates such as polyimide resin, thin film, liquid crystal material, semiconductor, flat panel display and the like.

Next, a dibromobiphenyl derivative in the present invention will be explained.

With respect to a method for synthesizing the dibromobiphenyl derivative, the above reaction is carried out by using a biphenyl compound having a structure represented by the general formula (15) as a raw material, without using other reactants (catalyst, etc.), and a dibromobiphenyl derivative having a structure represented by the general formula (16) is obtained under the reaction conditions only for an aprotic solvent and a bromination reagent. In this method, the reaction yield is high, the post-treatment is simple, the solvent recovery and use is facilitated, the pollution to the environment is small, and mass production is easily realized.

[Chemical Formula 25]

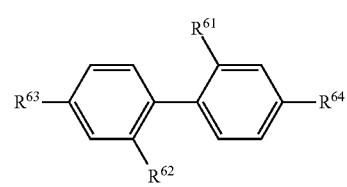

(15)

-continued

[Chemical Formula 26]

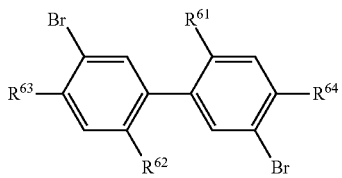

(16)

In the general formulae (15) and (16), $R^{61}$ and $R^{62}$ may be the same or different. They are each one kind selected from the group consisting of hydrogen, halogen, a $C_1$ to $C_6$ alkyl group, a $C_1$ to $C_6$ alkoxyl group, a hydroxyl group, a halogenated alkyl group, a substituted or unsubstituted amino group, a substituted or unsubstituted amide group, a substituted or unsubstituted $C_6$ to $C_{30}$ aryl group, an ester group and a nitro group. $R^3$ and $R^4$ may be the same or different. They are each one kind selected from the group consisting of a $C_1$ to $C_6$ alkyl group, a $C_1$ to $C_6$ alkoxyl group, a hydroxyl group, a substituted or unsubstituted aryl group, a substituted or unsubstituted amino group, a substituted or unsubstituted amide group, a substituted or unsubstituted imide group, a substituted or unsubstituted sulfamine group, a substituted or unsubstituted sulfinamide group, and a substituted or unsubstituted aromatic heterocyclic group. Among them, the substituents may be the same or different and represent one or more of trifluoromethyl, trimethylsilyl, a $C_1$ to $C_6$ alkoxyl group, a $C_1$ to $C_6$ alkyl group, an aryl alkoxyl group, a $C_6$ to $C_{30}$ aryl group, and a heterocyclic group.

In $R^{61}$ and $R^{62}$ described above, the halogen is preferably fluoro, chloro or bromo, more preferably fluoro or chloro.

The $C_1$ to $C_6$ alkyl group is preferably a $C_1$ to $C_6$ linear alkyl group, a $C_1$ to $C_6$ side chain alkyl group or a $C_1$ to $C_6$ cycloalkyl group, more preferably a $C_1$ to $C_6$ saturated aliphatic hydrocarbon group such as methyl, ethyl, n-propyl, isopropyl, n-butyl, sec-butyl, t-butyl, n-pentyl, isopentyl, neopentyl, cyclopentyl, n-hexyl and cyclohexyl. The $C_1$ to $C_6$ alkoxyl group is preferably a $C_1$ to $C_6$ linear alkoxyl group, a $C_1$ to $C_6$ side chain alkoxyl group or a $C_1$ to $C_6$ cycloalkoxyl group. More preferred is methoxy, ethoxy, propoxy, isopropoxy, n-butoxy, isobutoxy, t-butoxy, n-pentyloxy, isopentyloxy, neopentyloxy, n-hexyloxy, cyclopentyloxy, cyclohexyloxy or the like.

The halogenated alkyl group is preferably trifluoromethyl, trifluoroethyl, chloromethyl, dichloromethyl, trichloromethyl, dichloroethyl, tetrachloroethyl, bromomethyl, bromoethyl or the like, more preferably trifluoromethyl or trifluoroethyl, still more preferably trifluoromethyl. The substituted or unsubstituted amino group is preferably a primary amino group, secondary amino group or tertiary amino group, the amino group may be substituted by one or two groups, and the substituent in the amino group may be the same or different. The substituent is preferably a linear alkyl group, a side chain alkyl group, a cycloalkyl group, a halogenated alkyl group, an arylalkoxyl group, an aryl group, a heteroaryl group, a heterocyclic group or the like. An amino group, methylamino, ethylamino, propylamino, butylamino, pentylamino, hexylamino, isopropylamino, t-butylamino, cyclopentylamino, cyclohexylamino, dimethylamino, trifluoromethylamino, phenylamino, naphthylamino, anthracene amino, phenanthrylamino, pyrenylamino, benzylamino, pyridinamino, furanylamino, pyronylamino, carbazoylamino, thiopheneamino, quinoline amino or the like is more preferred, and an amino group is still more preferred. The substituted or unsubstituted amide group is preferably an alkylamide group, a halogenated alkylamide group, an arylalkoxyamide group, a heterocyclic group amide group, an arylamide group, an alkoxyamide group, or the like. Among them, the substituent may be connected to a carbonyl group or may be connected to an amino group, and acetamide, propionamide, butyrylamino, pentanamide, hexanamide, trifluoromethylamide, tertiarybutoxideamide, benzamide, naphthamide, bibenzamide, benzyloxyamide, pyridineformamide, furanylformamide, thiopheneformamide, acetopropylamine, or acetanilide is more preferred. Acetamide, tertiarybutoxideamide, benzyloxyamide or the like is still more preferred. The substituent of the substituted or unsubstituted aryl group is not particularly limited, but an aromatic hydrocarbon group such as a phenyl group, a naphthyl group, an anthracenyl group, a phenanthryl group, a pyrenyl group, a biphenyl group, or a terphenyl is preferred, the ester group is preferably a substituted or unsubstituted alkoxyl carbonic acid ester group, and methoxycarbonate ester, ethoxycarbonate ester, propoxycarbonate ester, butoxycarbonate ester, tertiarybutoxidecarbonate ester, benzyloxycarbonate ester, or fluorenylmethoxycarbonate ester and the like are more preferred.

In $R^{63}$ and $R^{64}$ described above, the description of the $C_1$ to $C_6$ alkyl group, the $C_1$ to $C_6$ alkoxyl group, the substituted or unsubstituted aryl group, the substituted or unsubstituted amino group, the substituted or unsubstituted amide group, and the substituent is as described above.

The substituted or unsubstituted imide group is preferably a $C_1$ to $C_6$ alkyl imide group, a $C_1$ to $C_6$ halogenated alkyl imide group, a $C_1$ to $C_6$ alkoxy imide group, a $C_6$ to $C_{30}$ aryl imide group, an aryl alkoxy imide group, a heterocyclic imide group or the like, more preferably phthalimide, succinimide, ditertiarybutoxidedicarboximide, dibenzyloxydicarboximide or the like. The substituted or unsubstituted sulfamine group is preferably a $C_1$ to $C_6$ alkylsulfamine group, a $C_1$ to $C_6$ halogenated alkylsulfamine group, a $C_1$ to $C_6$ arylsulfamine group, or a heterocyclic sulfamine group, more preferably methanesulfonamide, trifluoromethylsulfamic, benzenesulfonamide, p-toluenesulfonamide or the like. The substituted or unsubstituted sulfinamide group is preferably a $C_1$ to $C_6$ alkylsulfinamide group, a $C_1$ to $C_6$ halogenated alkylsulfinamide group, a $C_1$ to $C_6$ arylsulfinamide group, a heterocyclic sulfinamide group, or the like, more preferably methylsulfinamide, trifluoromethylsulfinamide, phenylsulfinamide, p-toluenesulfinamide, t-butylsulfinamide or the like. The substituted or unsubstituted aromatic heterocyclic group is preferably a cyclic aromatic group having a hetero atom other than carbon in one or more rings, and may be substituted or unsubstituted. Although not particularly limited to the number of carbon atoms of an aromatic heterocyclic ring, an aromatic heterocyclic group having 2 to 30 carbon atoms is preferred. Preferred is a nitrogen-containing aromatic heterocyclic group such as a pyrrole group, a pyridine group, a pyrimidinyl group, a quinoline group, a pyrazine group, a carbazoyl group, an indolyl group, or a phthalimido group, and more preferred is a phthalimido group.

In the substituent, the $C_1$ to $C_6$ alkoxyl group is preferably a $C_1$ to $C_6$ linear alkoxyl group, a $C_1$ to $C_6$ side chain alkoxyl group or a $C_1$ to $C_6$ cycloalkoxyl group, more preferably methoxy, ethoxy, propoxy, isopropoxy, n-butoxy, isobutoxy, t-butoxy, n-pentyloxy, isopentyloxy, neopentyloxy, n-hexyloxy, cyclohexyloxy or the like. The $C_1$ to $C_6$ alkyl group is preferably a $C_1$ to $C_6$ linear alkyl group, a $C_1$ to $C_6$ side chain alkyl group or a $C_1$ to $C_6$ cycloalkyl group, more preferably a $C_1$ to $C_6$ saturated aliphatic hydrocarbon group such as methyl, ethyl, n-propyl, isopropyl, n-butyl, sec-butyl, t-butyl, n-pentyl, isopentyl, neopentyl, cyclopentyl, n-hexyl and cyclohexyl. The arylalkoxyl group is preferably a benzyloxy group, a naphthylmethoxy group, an anthracenylmethoxy group, a fluorenylmethoxy group, a 3,5-di-t-butylphenyl-1-isopropoxy group, a phenylethoxy group, a naphthylethoxy group, benzidine-3-methoxy group or the like, more preferably a benzyloxy group or a fluorenylmethoxy group.

The $C_6$ to $C_{30}$ aryl group is preferably an aromatic hydrocarbon group such as a phenyl group, a naphthyl group, an anthracenyl group, a phenanthryl group, a pyrenyl group, a biphenyl group, or a terphenyl.

The heterocyclic group is preferably a pyridine group, a carbazoyl group, an imidazole group, a furanyl group, a thiophene group, an oxazoyl group, an indolyl group, a benzofuranyl group, a benzothiophene group, a thiazinyl group, a pyrimidine group, a quinolyl group, an isoquinolyl group, a pyrazo group, an imidazole group, a thiazoyl group, a pyranyl group, a bipelazine group, a phenazine group, a phenothiazine group, a pyridazinyl group, a tetrahydrofuran group, a dioxane group, a phthalimide group, a succinimido group or the like, more preferably a phthalimido group or a succinimido group.

$R^{61}$ and $R^{62}$ may be the same or different from the viewpoint of difficulty of raw material industrial production and are preferably each one kind selected from the group consisting of halogen, a $C_1$ to $C_6$ alkyl group, a $C_1$ to $C_6$ alkoxyl group, a halogenated alkane, an ester group and a nitro group. From the viewpoint of raw material cost, the halogenated alkane is preferably one of trifluoromethyl and trifluoroethyl, the $C_1$ to $C_6$ alkyl group is more preferably methyl, and the $C_1$ to $C_6$ alkoxyl group is more preferably methoxy.

From the viewpoints of availability of raw materials and selectivity of bromination reaction, $R^{63}$ and $R^{64}$ may be the same or different, and are preferably each one kind selected from the group consisting of a substituted or unsubstituted amino group, a substituted or unsubstituted amide group, a substituted or unsubstituted imide group, a substituted or unsubstituted sulfamine group, a substituted or unsubstituted sulfinamide group, and a substituted or unsubstituted aromatic heterocyclic group. From the viewpoint of raw material cost, they are more preferably each independently one of an amino group, an acetamide group, a tertiarybutoxideamide group, a benzyloxyamide group, a ditertiarybutoxidedicarboximide group, a dibenzyloxydicarboximide group, and a phthalimide group.

Hereinafter, the solvent used in the present invention will be described in detail. The aprotic solvent used in the present invention contains one or more kinds of alkane solvents (such as cyclohexane, normal hexane, and normal pentane), arene solvents (such as benzene, toluene, and xylene), haloalkane solvents (such as dichloromethane, trichloromethane, carbon tetrachloride, dichloroethane, and tetrachloroethane), ester solvents (such as methyl acetate, ethyl acetate, propyl acetate, butyl acetate, and propyleneglycolmethyletheracetate), ether solvents (such as ethyl ether, tetrahydrofuran, and 1,4-dioxane), ketones (such as acetone, butanone, and methylethylketone) and other kinds of aprotic solvents (such as N,N-dimethylformamide, N-methylpyrrolidone, acetonitrile, and dimethylsulfoxide) and is preferably one or more of ester solvents, ether solvents, arene solvents and the above solvents. From the viewpoints of solubility of raw materials and stability in reactions, ester solvents, ether solvents or mixtures thereof are preferred, and from the comprehensive viewpoint of solubility and price of the solvent, one or more of methylacetate, ethylacetate, propylacetate, butylacetate, propyleneglycolmethyletheracetate, glycoldimethylether, tetrahydrofuran, 1,4-dioxane and the like, and the mixed solvents described above are more preferred.

Hereinafter, the bromination solvent used in the present invention will be described in detail. The bromination solvent used in the present invention is selected from one or more of the following reagents.

[Chemical Formula 27]

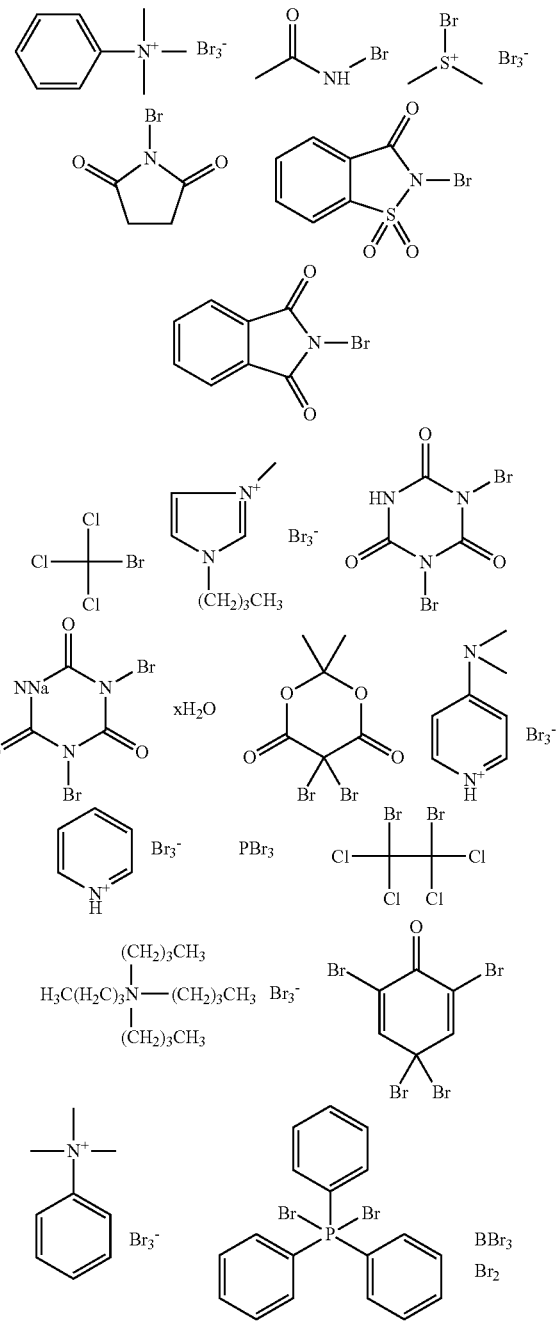

From the viewpoints of the price, safety, and operation convenience of a bromination reagent, NBS or $Br_2$ is preferred, and Br$_2$ is more preferred. In the present invention, the molar ratio of a raw material biphenyl compound to a bromination reagent is 1:2 to 1:6, and from the comprehensive viewpoints of the price, yield and difficulty in post-treatment of the raw material, the molar ratio of the raw material biphenyl compound to the bromination reagent is preferably 1:2 to 1:3.

The molar concentration of the raw material biphenyl compound in the present invention is preferably from 0.05 mol/L to 5 mol/L, and from the viewpoints of solubility and solvent cost, the molar concentration of the raw material biphenyl compound is more preferably 0.2 mol/L to 2 mol/L.

The reaction temperature in the present invention is preferably from −30° C. to 60° C., and more preferably from −20° C. to 60° C. from the viewpoint of mass production cost. The reaction time in the present invention is preferably from 1 h to 48 h, and more preferably from 1 h to 12 h from the viewpoints of reaction rate and mass production cost.

In the post-treatment of the present invention, when an alkali is added to adjust pH, the alkali used is preferably an inorganic alkali, and from the viewpoint of mass production cost, sodium carbonate, potassium carbonate, calcium carbonate, sodium bicarbonate, potassium bicarbonate, sodium hydroxide, potassium hydroxide, calcium hydroxide, lithium hydroxide or the like is preferred.

In the post-treatment of the present invention, when extraction is carried out using an organic solvent, ethyl acetate, butyl acetate, dichloromethane, toluene or the like is preferred from the viewpoints of the cost and solubility of the solvent.

When a crude product of the present invention is purified, from the viewpoints of the cost and solubility of the solvent, the solvent used is preferably one or more solvents such as petroleum ether, ethyl acetate, butyl acetate, toluene, xylene, dichloromethane, 1,2-dichloroethane, acetonitrile, ethanol, methanol, isopropanol, propyleneglycolmethyletheracetate, glycoldimethylether, ethylether, tetrahydrofuran, and 1,4-dioxane.

EXAMPLES

Hereinafter, the present invention will be described with reference to examples and so on in the order of (1) resin, photosensitive resin composition, (2) 5,5'-dihydroxyl-4,4'-diaminobiphenyl derivative, and (3) dibromobiphenyl derivative, but the present invention is not limited by these examples.

<Resin and Photosensitive Resin Composition>

Resins and resin compositions in the examples were evaluated by the following method.

1) Method for Measuring Film Thickness

Lambda Ace STM-602 manufactured by Dainippon Screen Mfg. Co., Ltd. was used, and both a resin film and a film after heat curing were measured to have a refractive index of 1.629.

2) Method for Measuring Coefficient of Linear Thermal Expansion

A resin solution was spin-coated on an 8-inch silicon wafer and then baked for 3 minutes on a hot plate (using a coating and developing apparatus Act-8 manufactured by Tokyo Electron Limited) at 120° C. to obtain a resin film. The temperature of this resin film was raised to 250° C. at an oxygen concentration of 20 ppm or less at 5° C./min using an inert oven CLH-21 CD-S (manufactured by Koyo Thermo Systems Co., Ltd.), heat treatment was carried out at 250° C. for 1 hour, and then cooling was carried out to 50° C. at 5° C./min. Subsequently, the film was immersed in hydrofluoric acid for 1 to 4 minutes to be peeled from a substrate and then to be air-dried, whereby a film after heat treatment was obtained. A rotational speed at the time of spin coating was adjusted such that thickness of the resin film after heat treatment was 10 μm.

The film after the heat treatment was measured in a nitrogen stream using a thermomechanical analyzer (EXSTAR6000 TMA/SS 6000 manufactured by SII Nanotechnology Inc.). A temperature rise method was carried out under the following conditions. In the first stage, a temperature of a sample was raised to 200° C. at a rate of temperature rise of 5° C./min to remove adsorbed water from the sample, and in the second stage, the sample was air cooled to room temperature at a rate of temperature fall of 5° C./min. In the third stage, the main measurement was carried out at the temperature rise rate of 5° C./min, and an average value of the coefficient of linear thermal expansion at 50° C. to 200° C. was obtained.

However, only with respect to resins (D1) to (D5) to be described later, while those subjected to heat treatment at 250° C. for 1 hour were measured, those subjected to heat treatment at 320° C. for 1 hour were measured.

3) Method for Measuring Absorbance

A resin solution was spin-coated on a glass substrate (AN-100, manufactured by Asahi Glass Co., Ltd.) having a thickness of 50 mm×50 mm×0.7 mm using a spin coater MS-A 200 manufactured by Mikasa Co., Ltd., and then the coated substrate was baked for 3 minutes on a hot plate (D-SPIN manufactured by Dainippon Screen Co., Ltd.) at 120° C. to obtain a resin film. The rotational speed at the time of spin coating was adjusted such that thickness of the resin film was 10 μm.

With respect to the obtained resin film, the absorbance at 365 nm was measured using an ultraviolet-visible spectrophotometer (MultiSpec 1500 manufactured by Shimadzu Corporation). The obtained absorbance was divided by the resin film thickness to obtain the absorbance per 1 μm.

4) Method for Measuring Alkali Developing Speed

A resin solution was spin-coated on an 8-inch silicon wafer and then baked for 4 minutes on a hot plate (using a coating and developing apparatus Act-8 manufactured by Tokyo Electron Limited) at 120° C. to obtain a resin film. The rotational speed at the time of spin coating was adjusted such that thickness of the resin film was 10 μm.

The resin film was developed for 60 seconds with a 2.38% by weight tetramethylammonium (TMAH) aqueous solution (ELM-D produced by Mitsubishi Gas Chemical Company, Inc.), and then rinsed with pure water. The film thickness after rinsing was measured, and a reduction in film thickness per minute was calculated.

5) Method for Measuring Residual Stress

A resin solution was spin-coated on an 8-inch silicon wafer and then baked for 3 minutes on a hot plate (using a coating and developing apparatus Act-8 manufactured by Tokyo Electron Limited) at 120° C. to obtain a resin film.

The temperature of this resin film was raised to 250° C. at an oxygen concentration of 20 ppm or less at 5° C./min using an inert oven CLH-21 CD-S (manufactured by Koyo Thermo Systems Co., Ltd.), heat treatment was carried out at 250° C. for 1 hour, and then cooling was carried out to 50° C. at 5° C./min. Subsequently, the film was immersed in hydrofluoric acid for 1 to 4 minutes to be peeled from a substrate and then to be air-dried, whereby a film after heat treatment was obtained. A rotational speed at the time of spin coating was adjusted such that thickness of the resin film after heat treatment was 10 μm.

With respect to the film after the heat treatment, residual stress was measured at 23° C. and 45% RH under an air atmosphere using a thin film stress measurement device (manufactured by KLA-Tencor Corporation). As a blank, a silicon wafer before coating of the resin solution was used.

6) Photosensitivity Evaluation Method

A resin solution was spin-coated on an 8-inch silicon wafer and then baked for 3 minutes on a hot plate (using a coating and developing apparatus Act-8 manufactured by Tokyo Electron Limited) at 120° C. to produce a prebaked film having a thickness of 6 μm. This film was exposed with an exposure energy of 0 to 1000 mJ/cm² at a 10 mJ/cm² step using an i-line stepper (NIKON NSR i9). After exposure, the film was developed for 90 seconds with a 2.38% by weight tetramethylammonium (TMAH) aqueous solution (ELM-D produced by Mitsubishi Gas Chemical Company, Inc.), and then rinsed with pure water. At this time, the exposure energy (referred to as a minimum exposure energy Eth) at which an exposed portion was completely dissolved and disappeared after the exposure and development was taken as sensitivity. When Eth is 700 mJ/cm² or less, it can be judged that sensitivity is high. Eth is more preferably 500 mJ/cm² or less.

Abbreviations of acid dianhydride and diamine shown in the following examples and comparative examples are as follows.
PMDA: pyromellitic anhydride
ODPA: 3,3',4,4'-diphenylethertetracarboxylic acid dianhydride
SiDA: 1,1,3,3-tetramethyl-1,3-bis(3-aminopropyl)disiloxane
NMP: N-methyl-2-pyrrolidone
GBL: Gamma-butyrolactone
3-Aph: m-aminophenol
PMDA-H: 1S, 2S, 4R, 5R-cyclohexanetetracarboxylic dianhydride
NA: 5-norbornene-2.3-dicarboxylic anhydride
TFMB: 2,2'-bis(trifluoromethyl)benzidine
HAB: 3,3'-dihydroxybenzidine
BPDA: 3,3',4,4'-biphenyltetracarboxylic acid dianhydride
KBM-403: 3-glycidoxypropyltrimethoxysilane.
BAHF: 2,2-bis(3-amino-4-hydroxyphenyl)hexafluoropropane
HFHA: 2,2-bis[3-(3-aminobenzamide)-4-hydroxyphenyl]hexafluoropropane
DAE: 4,4'-diaminodiphenylether.

Synthesis Example 1 Synthesis of Hydroxyl Group-Containing Diamine Compound (a)

17.6 g (0.05 mol) of 2,2'-bis(trifluoromethyl)-5,5'-dihydroxybenzidine was dissolved in 100 mL of acetone and 17.4 g (0.3 mol) of propyleneoxide and cooled to −15° C. A solution prepared by dissolving 20.4 g (0.11 mol) of 3-nitrobenzoyl chloride in 100 mL of acetone was dropped thereto. After completion of the dropping, the mixture was allowed to react at −15° C. for 4 hours, and then the temperature was returned to room temperature. A precipitated white solid was separated by filtration and vacuum dried at 50° C.

30 g of the obtained white solid was placed in a 300 mL stainless steel autoclave and dispersed in 250 mL of methylcellosolve, and 2 g of 5% palladium-carbon was added. Hydrogen was introduced here with a balloon, and a reduction reaction was carried out at room temperature. About 2 hours later, the reaction was terminated on confirmation of the fact that the balloon no longer shrank. After the termination of the reaction, a palladium compound as a catalyst was removed by filtration, followed by concentration with a rotary evaporator, affording a hydroxyl group-containing diamine compound (a) represented by the following formula. An obtained solid was used in the reaction as it was.

[Chemical Formula 28]

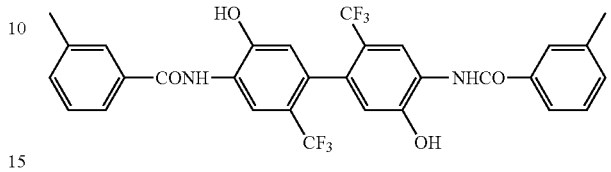

Synthesis Example 2 Synthesis of Hydroxyl Group-Containing Diamine Compound (b)

A hydroxyl group-containing diamine compound (b) represented by the following formula was obtained in the same manner as in Synthesis Example 1 except that 17.6 g (0.05 mol) of 2,2'-bis(trifluoromethyl)-5,5'-dihydroxybenzidine was changed to 17.6 g (0.05 mol) of 2,2'-dimethyl-5,5'-dihydroxybenzidine. An obtained solid was used in the reaction as it was.

[Chemical Formula 29]

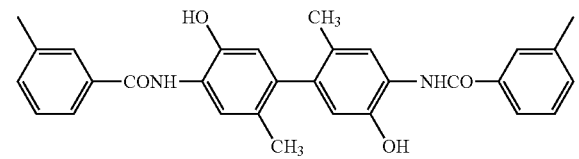

Synthesis Example 3 Synthesis of Hydroxyl Group-Containing Diamine Compound (c)

A hydroxyl group-containing diamine compound (c) represented by the following formula was obtained in the same manner as in Synthesis Example 1 except that 20.4 g (0.11 mol) of 3-nitrobenzoyl chloride was changed to 20.4 g (0.11 mol) of 4-nitrobenzoyl chloride. An obtained solid was used in the reaction as it was.

[Chemical Formula 30]

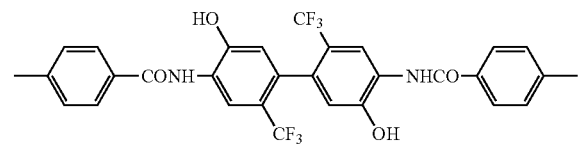

Synthesis Example 4 Synthesis of Hydroxyl Group-Containing Acid Dianhydride (d)

In a dry nitrogen stream, 17.6 g (0.05 mol) of 2,2'-bis(trifluoromethyl)-5,5'-dihydroxybenzidine and 34.2 g (0.3 mol) of allyl glycidyl ether were dissolved in 100 g of ethylacetate and cooled to −15° C. 22.1 g (0.11 mol) of trimellitic anhydride chloride dissolved in 50 g of ethylacetate was dropped thereto so that a temperature of a reaction liquid did not exceed 00° C. After completion of the dropping, the mixture was stirred at 0° C. for 4 hours.

This solution was concentrated with a rotary evaporator and charged into 1 l of toluene to obtain a hydroxyl group-containing acid dianhydride (d) represented by the following formula. An obtained solid was used in the reaction as it was.

[Chemical Formula 31]

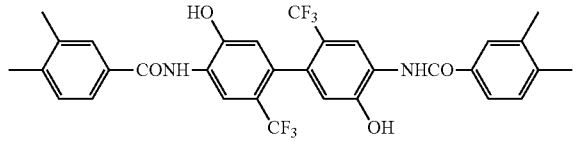

Synthesis Example 5 Synthesis of Quinonediazide Compound (e)

In a dry nitrogen stream, 21.22 g (0.05 mol) of TrisP-PA (trade name, produced by Honshu Chemical Industry Co., Ltd.), 26.86 g (0.10 mol) of 5-naphthoquinonediazidosulfonylchloride, and 13.43 g (0.05 mol) of 4-naphthoquinonediazidosulfonylchloride were dissolved in 50 g of 1,4-dioxane, and the temperature was brought to room temperature. 15.18 g of triethylamine mixed with 50 g of 1,4-dioxane was dropped here so that the temperature of the system did not become 35° C. or more. After completion of the dropping, the mixture was stirred at 30° C. for 2 hours. A triethylamine salt was filtered, and the filtrate was charged into water. Thereafter, the resulting precipitate was collected by filtration. This precipitate was dried in a vacuum drier to obtain a quinonediazide compound (e) represented by the following formula.

[Chemical Formula 32]

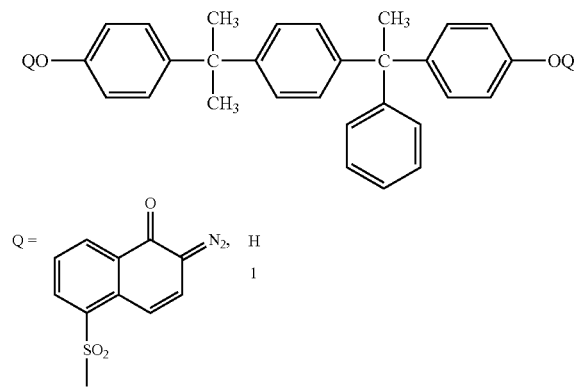

Synthesis Example 6

In a dry nitrogen stream, 15.8 g (0.045 mol) of 2,2'-bis(trifluoromethyl)-3,3'-dihydroxybenzidine as an amine component and 0.62 g (0.0025 mol) of SiDA were dissolved in 100 g of GBL. 10.91 g (0.05 mol) of PMDA as an acid component was added thereto together with 10 g of GBL and reacted at 60° C. for 2 hours, and then 0.545 g (0.005 mol) of 3-Aph as an end-capping agent was added together with 10 g of NMPGBL. The mixture was stirred at 60° C. for 2 hours to obtain a resin solution (A1).

Synthesis Examples 7 to 31

Resin solutions (A2) to (A26) were obtained in the same manner as in Synthesis Example 6 using a combination of the amine component, the acid component and the end-capping agent shown in Table 1.

Synthesis Example 32

In a dry nitrogen stream, 15.8 g (0.045 mol) of 2,2'-bis(trifluoromethyl)-3,3'-dihydroxybenzidine as an amine component and 0.62 g (0.0025 mol) of SiDA were dissolved in 100 g of NMP. 10.91 g (0.05 mol) of PMDA as an acid component was added thereto together with 10 g of NMP and reacted at 40° C. for 1 hour, and then 0.545 g (0.005 mol) of 3-Aph as an end-capping agent was added together with 10 g of NMP. The mixture was stirred at 40° C. for 2 hours. Then, a solution in which 15.19 g (0.127 mol) of N,N-dimethylformamide dimethylacetal had been diluted with 4 g of NMP was dropped over 10 minutes. After completion of the dropping, the mixture was stirred at 40° C. for 2 hours. After the termination of the reaction, 30 g of acetic acid was slowly charged while keeping the solution temperature at 30° C. or less. After stirring at 30° C. or less for 30 minutes, the solution was charged into 2 L of water, and a precipitate of a polymer powder was collected by filtration. This precipitate was collected by filtration and washed three times with water, and then the polymer powder was dried in a vacuum oven at 50° C. for 72 hours to obtain a powder of resin (B1).

Synthesis Examples 33 to 57

Resin solutions (B2) to (B26) were obtained in the same manner as in Synthesis Example 32 using a combination of the amine component, the acid component and the end-capping agent shown in Table 2.

Synthesis Example 58

In a dry nitrogen stream, 15.8 g (0.045 mol) of 2,2'-bis(trifluoromethyl)-3,3'-dihydroxybenzidine as an amine component and 0.62 g (0.0025 mol) of SiDA were dissolved in 100 g of NMP. 10.91 g (0.05 mol) of PMDA as an acid component was added thereto together with 10 g of NMP and reacted at 60° C. for 1 hour, and then 0.545 g (0.005 mol) of 3-Aph as an end-capping agent was added together with 10 g of NMP. The mixture was stirred at 60° C. for 1 hour and further stirred at 200° C. for 4 hours. After completion of the stirring, the solution was charged into 2 L of water to obtain a white precipitate. This precipitate was collected by filtration, washed three times with water, and then dried in a vacuum oven at 50° C. for 72 hours to obtain a powder of resin (C1)

Synthesis Examples 59 to 79

Powders of resins (C2) to (C22) were obtained in the same manner as in Synthesis Example 58 using a combination of the amine component, the acid component and the end-capping agent shown in Table 3.

Synthesis Example 80

The procedure was carried out in the same manner as in Synthesis Example 58 except that 15.8 g (0.045 mol) of 2,2'-bis(trifluoromethyl)-3,3'-dihydroxybenzidine was changed to 9.73 g (0.045 mol) of HAB. However, the polymer was precipitated during cooling the solution after the reaction at 200° C., so that an insoluble resin was produced.

Synthesis Example 81

In a dry nitrogen stream, 17.6 g (0.05 mol) of 2,2'-bis(trifluoromethyl)-3,3'-dihydroxybenzidine was dissolved in 50 g of NMP and 26.4 g (0.3 mol) of glycidylmethylether, and the temperature of the solution was cooled to −15° C. A solution prepared by dissolving 8.12 g (0.04 mol) of isophthaloyl dichloride in 25 g of GBL was dropped thereto so that an internal temperature did not exceed 0° C. After completion of the dropping, stirring was continued at −15° C. for 6 hours. Then, 3.28 g (0.02 mol) of NA was charged, and the mixture was stirred at room temperature for 4 hours. After completion of the reaction, the solution was charged into 3 L of water containing 10% by weight of methanol to deposit a white precipitate. This precipitate was collected by filtration, washed three times with water, and then dried in a vacuum oven at 50° C. for 72 hours to obtain a powder of resin (D1).

Synthesis Examples 82 to 84

Powders of resins (D2) to (D4) were obtained in the same manner as in Synthesis Example 81 using a combination of the amine component, the acid component and the end-capping agent shown in Table 4.

Synthesis Example 85

In a dry nitrogen stream, 17.6 g (0.05 mol) of 2,2'-bis(trifluoromethyl)-3,3'-dihydroxybenzidine was dissolved in 100 g of NMP. 14.32 g (0.04 mol) of diphenyletherdicarboxylic acid diimidazolide was added thereto together with 10 g of NMP, and the mixture was stirred at 85° C. for 4 hours. Then, 3.28 g (0.02 mol) of NA was charged, and the mixture was stirred at 85° C. for 2 hours. After the termination of the reaction, 30 g of acetic acid was slowly charged while keeping the solution temperature at 30° C. or less. After stirring at 30° C. or less for 30 minutes, the solution was charged into 2 L of water, and a precipitate of a polymer powder was collected by filtration. This precipitate was collected by filtration and washed three times with water, and then the polymer powder was dried in a vacuum oven at 50° C. for 72 hours to obtain a powder of resin (D5).

Examples 1 to 63, Comparative Examples 1 to 16

The resins (A1) to (A26) were maintained in a solution state, the resins (B1) to (B26), the resins (C1) to (C22), and the resins (D1) to (D5) were dissolved in GBL, and a solution having a concentration of 40% was produced. Table 5-1 and Table 5-2 show results obtained by measuring the coefficient of linear thermal expansion, absorbance, alkali developing speed and residual stress as described above using the obtained solution.

Example 64

17.5 g of the resin (B1), 2.3 g of the quinonediazide compound (b) obtained in Synthesis Example 5 and 0.5 g of KBM-403 were added to 45 g of GBL to obtain a photosensitive resin composition. The photosensitivity was evaluated as described above using the obtained photosensitive resin composition. Table 6 show evaluation results.

Examples 65 to 106, Comparative Examples 17 to 26

A photosensitive resin composition was obtained in the same manner as in Example 64 for the resins (B2) to (B26), the resins (C1) to (C22) and the resins (D1) to (D5). The photosensitivity was evaluated as described above using the obtained photosensitive resin composition. Table 6 shows evaluation results.

TABLE 1

| Synthesis example | Resin liquid | Amine component ① | Amine component ② | Acid component ① | Acid component ② | Terminal blocking agent |
|---|---|---|---|---|---|---|
| 6 | A1 | SiDA 0.62 g (0.0025 mol) | 2,2'-bis(trifluoromethyl)-3,3'-dihydroxybenzidine 15.8 g (0.045 mol) | PMDA 10.91 g (0.05 mol) | — | 3-Aph 0.545 g (0.005 mol) |
| 7 | A2 | SiDA 0.62 g (0.0025 mol) | 2,2'-bis(trifluoromethyl)-3,3'-dihydroxybenzidine 15.8 g (0.045 mol) | PMDA 8.72 g (0.04 mol) | PMDA-H 2.24 g (0.01 mol) | 3-Aph 0.545 g (0.005 mol) |
| 8 | A3 | SiDA 0.62 g (0.0025 mol) | 2,2'-bis(trifluoromethyl)-3,3'-dihydroxybenzidine 15.8 g (0.045 mol) | PMDA 5.45 g (0.025 mol) | PMDA-H 5.6 g (0.025 mol) | 3-Aph 0.545 g (0.005 mol) |
| 9 | A4 | SiDA 0.62 g (0.0025 mol) | 2,2'-bis(trifluoromethyl)-3,3'-dihydroxybenzidine 15.8 g (0.045 mol) | PMDA 3.27 g (0.015 mol) | PMDA-H 7.84 g (0.035 mol) | 3-Aph 0.545 g (0.005 mol) |
| 10 | A5 | SiDA 0.62 g (0.0025 mol) | 2,2'-bis(trifluoromethyl)-3,3'-dihydroxybenzidine 15.8 g (0.045 mol) | PMDA-H 11.2 g (0.05 mol) | — | 3-Aph 0.545 g (0.005 mol) |
| 11 | A6 | SiDA 0.62 g (0.0025 mol) | 2,2'-bis(trifluoromethyl)-4,4'-dihydroxy-3,3'-diaminobiphenyl 15.8 g (0.045 mol) | PMDA 5.45 g (0.025 mol) | PMDA-H 5.6 g (0.025 mol) | 3-Aph 0.545 g (0.005 mol) |
| 12 | A7 | SiDA 0.62 g (0.0025 mol) | 2,2'-bis(trifluoromethyl)-3,3'-dihydroxy-4,4'-diaminodiphenyl ether 16.56 g (0.045 mol) | PMDA 5.45 g (0.025 mol) | PMDA-H 5.6 g (0.025 mol) | 3-Aph 0.545 g (0.005 mol) |
| 13 | A8 | SiDA 0.62 g (0.0025 mol) | 2,2'-dimethyl-3,3'-dihydroxybenzidine 10.98 g (0.045 mol) | PMDA 5.45 g (0.025 mol) | PMDA-H 5.6 g (0.025 mol) | 3-Aph 0.545 g (0.005 mol) |
| 14 | A9 | SiDA 0.62 g (0.0025 mol) | 5,5'-dimethyl-3,3'-dihydroxybenzidine 10.98 g (0.045 mol) | PMDA 5.45 g (0.025 mol) | PMDA-H 5.6 g (0.02 mol %) | 3-Aph 0.545 g (0.005 mol) |

TABLE 1-continued

| Synthesis example | Resin liquid | Amine component ① | Amine component ② | Acid component ① | Acid component ② | Terminal blocking agent |
|---|---|---|---|---|---|---|
| 15 | A10 | SiDA 0.62 g (0.0025 mol) | 5,5'-bis(trifluoromethyl)-3,3'-dihydroxybenzidine 15.8 g (0.045 mol) | PMDA 5.45 g (0.025 mol) | PMDA-H 5.6 g (0.025 mol) | 3-Aph 0.545 g (0.005 mol) |
| 16 | A11 | SiDA 0.62 g (0.0025 mol) | 5,5'-dimethyl-3,3'-dihydroxy-4,4'-diaminodiphenyl ether 11.7 g (0.045 mol) | PMDA 5.45 g (0.025 mol) | PMDA-H 5.6 g (0.025 mol) | 3-Aph 0.545 g (0.005 mol) |
| 17 | A12 | SiDA 0.62 g (0.0025 mol) | 5,5'-dimethyl-4,4'-dihydroxy-3,3'-diaminobiphenyl 10.98 g (0.045 mol) | PMDA 5.45 g (0.025 mol) | PMDA-H 5.6 | 3-Aph 0.545 g (0.005 mol) |
| 18 | A13 | SiDA 0.62 g (0.0025 mol) | 4,4'-dimethyl-5,5'-dihydroxy-3,3'-diaminobiphenyl 10.98 g (0.045 mol) | PMDA 5.45 g (0.025 mol) | PMDA-H 5.6 g (0.025 mol) | 3-Aph 0.545 g (0.005 mol) |
| 19 | A14 | SiDA 0.62 g (0.0025 mol) | 2,2'-bis(trifluoromethyl)-3,3'-dihydroxybenzidine 15.8 g (0.045 mol) | ODPA 15.51 g (0.05 mol) | — | 3-Aph 0.545 g (0.005 mol) |
| 20 | A15 | SiDA 0.62 g (0.0025 mol) | diamine (a) 26.55 g (0.045 mol) | PMDA 5.45 g (0.025 mol) | (PMDA-H 5.6 g (0.025 mol) | 3-Aph 0.545 g (0.005 mol) |
| 21 | A16 | SiDA 0.62 g (0.0025 mol) | 2,2'-bis(trifluoromethyl)-3,3'-dihydroxybenzidine 15.8 g (0.045 mol) | BPDA 14.71 g (0.05 mol) | — | 3-Aph 0.545 g (0.005 mol) |
| 22 | A17 | SiDA 0.62 g (0.0025 mol) | diamine (b) 21.69 g (0.045 mol) | PMDA 5.45 g (0.025 mol) | PMDA-H 5.6 g (0.025 mol) | 3-Aph 0.545 g (0.005 mol) |
| 23 | A18 | SiDA 0.62 g (0.0025 mol) | diamine (c) 26.55 g (0.045 mol) | PMDA 5.45 g (0.025 mol) | PMDA-H 5.6 g (0.025 mol) | 3-Aph 0.545 g (0.005 mol) |
| 24 | A19 | SiDA 0.62 g (0.0025 mol) | 2,2'-bis(trifluoromethyl)-3,3'-dihydroxybenzidine 15.8 g (0.045 mol) | 35.0 g of acid dianhydride (d) (0.05 mol) | — | 3-Aph 0.545 g (0.005 mol) |
| 25 | A20 | SiDA 0.62 g (0.0025 mol) | TFMB 14.4 g (0.045 mol) | 35.0 g of acid dianhydride (d) | — | 3-Aph 0.541 g (0.005 mol) |
| 26 | A21 | SiDA 0.62 g (0.0025 mol) | TFMB 14.4 g (0.045 mol) | PMDA 10.91 g (0.05 mol) | — | 3-Aph 0.545 g (0.005 mol) |
| 27 | A22 | SiDA 0.62 g (0.0025 mol) | HAB 9.72 g (0.045 mol) | PMDA 10.91 g (0.05 mol) | — | 3-Aph 0.545 g (0.005 mol) |
| 28 | A23 | SiDA 0.62 g (0.0025 mol) | BAHF 16.48 g (0.045 mol) | ODPA 15.51 g (0.05 mol) | — | 3-Aph 0.545 g (0.005 mol) |
| 29 | A24 | SiDA 0.62 g (0.0025 mol) | HFHA 27.2 g (0.045 mol) | ODPA 15.51 g (0.05 mol) | — | 3-Aph 0.545 g (0.005 mol) |
| 30 | A25 | SiDA 0.62 g (0.0025 mol) | DAE 9.01 g (0.045 mol) | PMDA 5.45 g (0.025 mol) | PMDA-H 5.6 g (0.025 mol) | 3-Aph 0.545 g (0.005 mol) |
| 31 | A26 | SiDA 0.62 g (0.0025 mol) | DAE 9.01 g (0.045 mol) | ODPA 15.51 g (0.05 mol) | — | 3-Aph 0.545 g (0.005 mol) |

TABLE 2

| Synthesis example | Resin liquid | Amine component ① | Amine component ② | Acid component ① | Acid component ② | Terminal blocking agent |
|---|---|---|---|---|---|---|
| 32 | B1 | SiDA 0.62 g (0.0025 mol) | 2,2'-bis(trifluoromethyl)-3,3'-dihydroxybenzidine 15.8 g (0.045 mol) | PMDA 10.91 g (0.05 mol) | — | 3-Aph 0.545 g (0.005 mol) |
| 33 | B2 | SiDA 0.62 g (0.0025 mol) | 2,2'-bis(trifluoromethyl)-3,3'-dihydroxybenzidine 15.8 g (0.045 mol) | PMDA 8.72 g (0.04 mol) | PMDA-H 2.24 g (0.01 mol) | 3-Aph 0.545 g (0.005 mol) |
| 34 | B3 | SiDA 0.62 g (0.0025 mol) | 2,2'-bis(trifluoromethyl)-3,3'-dihydroxybenzidine 15.8 g (0.045 mol) | PMDA 5.45 g (0.025 mol) | PMDA-H 5.6 g (0.025 mol) | 3-Aph 0.545 g (0.005 mol) |
| 35 | B4 | SiDA 0.62 g (0.0025 mol) | 2,2'-bis(trifluoromethyl)-3,3'-dihydroxybenzidine 15.8 g (0.045 mol) | PMDA 3.27 g (0.015 mol) | PMDA-H 7.84 g (0.035 mol) | 3-Aph 0.545 g (0.005 mol) |
| 36 | B5 | SiDA 0.62 g (0.0025 mol) | 2,2'-bis(trifluoromethyl)-3,3'-dihydroxybenzidine 15.8 g (0.045 mol) | PMDA-H 11.2 g (0.05 mol) | — | 3-Aph 0.545 g (0.005 mol) |
| 37 | B6 | SiDA 0.62 g (0.0025 mol) | 2,2'-bis(trifluoromethyl)-4,4'-dihydroxy-3,3'-diaminobiphenyl 15.8 g (0.045 mol) | PMDA 5.45 g (0.025 mol) | PMDA-H 5.6 g (0.025 mol) | 3-Aph 0.545 g (0.005 mol) |
| 38 | B7 | SiDAM 0.62 g (0.0025 mol) | 2,2'-bis(trifluoromethyl)-3,3'-dihydroxy-4,4'-diaminodiphenyl ether 16.56 g (0.045 mol) | PMDA 5.45 g (0.025 mol) | PMDA-H 5.6 g (0.025 mol) | 3-Aph 0.545 g (0.005 mol) |
| 39 | B8 | SiDA 0.62 g (0.0025 mol) | 2,2'-dimethyl-3,3'-dihydroxybenzidine 10.98 g (0.045 mol) | PMDA 5.45 g (0.025 mol) | PMDA-H 5.6 g [0.025 mol] | 3-Aph 0.545 g (0.005 mol) |
| 40 | B9 | SiDA 0.62 g (0.0025 mol) | 5,5'-dimethyl-3,3'-dihydroxybenzidine 10.98 g (0.045 mol) | PMDA 5.45 g (0.025 mol) | PMDA-H 5.6 g (0.025 mol) | 3-Aph 0.545 g (0.005 mol) |

TABLE 2-continued

| Synthesis example | Resin liquid | Amine component ① | Amine component ② | Acid component ① | Acid component ② | Terminal blocking agent |
|---|---|---|---|---|---|---|
| 41 | B10 | SiDA 0.62 g (0.0025 mol) | 5,5'-bis(trifluoromethyl)-3,3'-dihydroxybenzidine 15.8 g (0.045 mol) | PMDA 5.45 g (0.025 mol) | PMDA-H 5.6 g (0.025 mol) | 3-Aph 0.545 g (0.005 mol) |
| 42 | B11 | SiDA 0.62 g (0.0025 mol) | 5,5'-dimethyl-3,3'-dihydroxy-4,4'-diaminodiphenyl ether 11.7 g (0.045 mol) | PMDA 5.45 g (0.025 mol) | PMDA-H 5.6 g (0.025 mol) | 3-Aph 0.545 g (0.005 mol) |
| 43 | B12 | SiDA 0.62 g (0.0025 mol) | 5,5'-dimethyl-4,4'-dihydroxy-3,3'-diaminobiphenyl 10.98 g (0.045 mol) | PMDA 5.45 g (0.025 mol) | PMDA-H 5.6 g (0.025 mol) | 3-Aph 0.545 g (0.005 mol) |
| 44 | B13 | SiDA 0.62 g (0.0025 mol) | 4,4'-dimethyl-5,5'-dihydroxy-3,3'-diaminobiphenyl 10.98 (0.045 mol) | PMDA 5.45 g (0.025 mol) | PMDA-H 5.6 g (0.025 mol) | 3-Aph 0.545 g (0.005 mol) |
| 45 | B14 | SiDA 0.62 g (0.0025 mol) | 2,2'-bis(trifluoromethyl)-3,3'-dihydroxybenzidine 15.8 g (0.045 mol) | ODPA 15.51 g (0.05 mol) | — | 3-Aph 0.545 g (0.005 mol) |
| 46 | B15 | SiDA 0.62 g (0.0025 mol) | diamine (a) 26.55 g (0.045 mol) | PMDA 5.45 g (0.025 mol) | PMDA-H 5.6 g (0.025 mol) | 3-Aph 0.545 g (0.005 mol) |
| 47 | B16 | SiDA 0.62 g (0.0025 mol) | 2,2'-bis(trifluoromethyl)-3,3'-dihydroxybenzidine 15.8 g (0.045 mol) | BPDA 14.71 g (0.05 mol) | — | 3-Aph 0.545 g (0.005 mol) |
| 48 | B17 | SiDA 0.62 g (0.0025 mol) | diamine (b) 21.69 g (0.045 mol) | PMDA 5.45 g (0.025 mol) | PMDA-H 5.6 g (0.025 mol) | 3-Aph 0.545 g (0.005 mol) |
| 49 | B18 | SiDA 0.62 g (0.0025 mol) | diamine (c) 26.55 g (0.045 mol) | PMDA 5.45 g (0.025 mol) | PMDA-H 5.6 g (0.025 mol) | 3-Aph 0.545 g (0.005 mol) |
| 50 | B19 | SiDA 0.62 g (0.0025 mol) | 2,2'-bis(trifluoromethyl)-3,3'-dihydroxybenzidine 15.8 g (0.045 mol) | 35.0 g acid dianhydride (d) (0.05 mol) | — | 3-Aph 0.545 g (0.005 mol) |
| 51 | B20 | SiDA 0.62 g (0.0025 mol) | TFMB 14.4 g (0.045 mol) | 35.0 g of acid dianhydride (d) (0.05 mol) | — | 3-Aph 0.545 g (0.005 mol) |
| 52 | B21 | SiDA 0.62 g (0.0025 mol) | TFMB 14.4 g (0.045 mol) | PMDA 10.91 g (0.05 mol) | — | 3-Aph 0.545 g (0.005 mol) |
| 53 | B22 | SiDA 0.62 g (0.0025 mol) | HAB 9.72 g (0.045 mol) | PMDA 10.91 g (0.05 mol) | — | 3-Aph 0.545 g (0.005 mol) |
| 54 | B23 | SiDA 0.62 g (0.0025 mol) | BAHF 16.48 g (0.045 mol) | ODPA 15.51 g (0.05 mol) | — | 3-Aph 0.545 g (0.005 mol) |
| 55 | B24 | SiDA 0.62 g (0.0025 mol) | HFHA 27.2 g (0.045 mol) | ODPA 15.51 g (0.05 mol) | — | 3-Aph 0.545 g (0.005 mol) |
| 56 | B25 | SiDA 0.62 g (0.0025 mol) | DAE 9.01 g (0.045 mol) | PMDA 5.45 g (0.025 mol) | PMDA-H 5.6 g (0.025 mol) | 3-Aph 0.545 g (0.005 mol) |
| 57 | B26 | SiDA 0.62 g (0.0025 mol) | DAE 9.01 g (0.045 mol) | ODPA 15.51 g (0.05 mol) | — | 3-Aph 0.545 g (0.005 mol) |

TABLE 3

| Synthesis example | Resin liquid | Amine component ① | Amine component ② | Acid component ① | Acid component ② | Terminal blocking agent |
|---|---|---|---|---|---|---|
| 58 | C1 | SiDA 0.62 g (0.0025 mol) | 2,2'-bis(trifluoromethyl)-3,3'-dihydroxybenzidine 15.8 g (0.045 mol) | PMDA 10.91 g (0.05 mol) | — | 3-Aph 0.545 g (0.005 mol) |
| 59 | C2 | SiDA 0.62 g (0.0025 mol) | 2,2'-bis(trifluoromethyl)-3,3'-dihydroxybenzidine 15.8 g (0.045 mol) | PMDA 0.72 g (0.04 mol) | PMDA-H 2.24 g (0.01 mol) | 3-Aph 0.545 g (0.005 mol) |
| 60 | C3 | SiDA 0.62 g (0.0025 mol) | 2,2'-bis(trifluoromethyl)-3,3'-dihydroxybenzidine 15.8 g (0.045 mol) | PMDA 5.45 g (0.025 mol) | PMDA-H 5.6 g (0.025 mol) | 3-Aph 0.545 g (0.005 mol) |
| 61 | C4 | SiDA 0.62 g (0.0025 mol) | 2,2'-bis(trifluoromethyl)-3,3'-dihydroxybenzidine 15.8 g (0.045 mol) | PMDA 3.27 g (0.015 mol) | PMDA-H 7.84 g (0.035 mol) | 3-Aph 0.545 g (0.005 mol) |
| 62 | C5 | SiDA 0.62 g (0.0025 mol) | 2,2'-bis(trifluoromethyl)-3,3'-dihydroxybenzidine 15.8 g (0.045 mol) | PMDA-H 11.2 g (0.05 mol) | — | 3-Aph 0.545 g (0.005 mol) |
| 63 | C6 | SiDA 0.62 g (0.0025 mol) | 2,2'-bis(trifluoromethyl)-4,4'dihydroxy-3,3'-diaminobiphenyl 15.8 g (0.045 mol) | PMDA 5.45 g (0.025 mol) | PMDA-H 5.6 g (0.025 mol) | 3-Aph 0.545 g (0.005 mol) |
| 64 | C7 | SiDA 0.62 g (0.0025 mol) | 2,2'-bis(trifluoromethyl)-3,3'-dihydroxy-4,4' diaminodiphenyl ether 16.56 g (0.045 mol) | PMDA 5.45 g (0.025 mol) | PMDA-H 5.6 g (0.025 mol) | 3-Aph 0.545 g (0.005 mol) |
| 65 | C8 | SiDA 0.62 g (0.0025 mol) | 2,2'-dimethyl-3,3'-dihydroxybenzidine 10.98 g (0.045 mol) | PMDA 5.45 g (0.025 mol) | PMDA-H 5.6 g (0.025 mol) | 3-Aph 0.545 g (0.005 mol) |
| 66 | C9 | SiDA 0.62 g (0.0025 mol | 5,5'-dimethyl-3,3'-dihydroxybenzidine 16.68 g [0.045 mol) | PMDA 5.45 g (0.025 mol) | PMDA-H 5.6 g (0.025 mol) | 3-Aph 0.545 g (0.005 mol) |

TABLE 3-continued

| Synthesis example | Resin liquid | Amine component ① | Amine component ② | Acid component ① | Acid component ② | Terminal blocking agent |
|---|---|---|---|---|---|---|
| 67 | C10 | SiDA 0.62 g (0.0025 mol) | 5,5'-bis(trifluoromethyl-3,3'-dihyroxybenzidine 15.8 g (0.045 g mol) | PMDA 5.45 g (0.025 mol) | PMDA-H 5.6 g (0.025 mol) | 3-Aph 0.545 g (0.005 mol) |
| 68 | C11 | SiDA 0.62 g (0.0025 mol) | 5,5'-dimethyl-3,3'-dihydroxy-4,4'-diaminodiphenyl ether 11.7 g (0.0045 mol) | PMDA 5.45 g (0.025 mol) | PMDA-H 5.6 g (0.025 mol) | 3-Aph 0.545 g (0.005 mol) |
| 69 | C12 | SiDA 0.62 g (0.0025 mol) | 5,5'-dimethyl-4-4'-dihydroxy-3,3'-5d diaminobiphenyl 10.58 g (0.025 mol) | PMDA 5.45 g (0.025 mol) | PMDA-H 5.6g (0.025 mol) | 3-Aph 0.545 g (0.005 mol) |
| 70 | C13 | SiDA 0.62 g (0.0025 mol) | 4,4'-dimethyl-4,4'-dihydroxy-3,3'-disaminobiphenyl 10.98 g (0.0045 mol) | PMDA 5.45 g (0.025 mol) | PMDA-H 5.6 g (0.025 mol) | 3-Aph 0.545 g (0.005 mol) |
| 71 | C14 | SiDA 0.62 g (0.0025 mol) | 2,2'-bis(trifluoromethyl)-3,3-dihydroxybenzidine 15.8 g (0.025 mol) | ODPA 15.51 g (0.05 mol) | — | 3-Aph 0.545 g (0.005 mol) |
| 72 | C15 | SiDA 0.62 g (0.0025 mol) | diamine (a) 36.55 g (0.045 mol) | PMDA 5.45 g (0.025 mol) | PMDA-H 5.6 g (0.025 mol) | 3-Aph 0.545 g (0.005 mol) |
| 73 | C16 | SiDA 0.62 g (0.0025 mol) | 2,2'-bis(trifluoromethyl)-3,3'-dihydroxybenzidine 15.8 g (0.045 mol) | BPDA 14.71 g (0.05 mol) | — | 3-Aph 0.545 g (0.005 mol) |
| 74 | C17 | SiDA 0.62 g (0.0025 mol) | diamine (b) 21.69 g (0.045 mol) | PMDA 5.45 g (0.025 mol) | PMDA-H 5.6 g (0.025 mol) | 3-Aph 0.545 g (0.005 mol) |
| 75 | C18 | SiDA 0.62 g (0.0025 mol) | diamine (c) 26.55 g (0.045 mol) | PMDA 5.45 g (0.025 mol) | PMDA-H 5.6 g (0.025 mol) | 3-Aph 0.545 g (0.005 mol) |
| 76 | C19 | SiDA 0.62 g (0.0025 mol) | 2,2'-(trifluoromethyl)-3,3'-dihydroxybenzidine 15.8 g (0.045 mol) | 35.0 g of acid dianhydride (d) (0.05 mol) | — | 3-Aph 0.545 g (0.005 mol) |
| 77 | C20 | SiDA 0.62 g (0.0025 mol) | TFMB 14.4 g (0.045 mol) | 35.0 g of acid dianhydride (d) (0.05 mol) | — | 3-Aph 0.545 g (0.005 mol) |
| 78 | C21 | SiDA 0.62 g (0.0025 mol) | BAHF 16.48 g (0.045 mol) | ODPA 15.51 g (0.05 mol) | — | 3-Aph 0.545 g (0.005 mol) |
| 79 | C22 | SiDA 0.62 g (0.0025 mol) | TFMB 14.4 g (0.045 mol) | PMDA 10.51 g (0.05 mol) | — | 3-Aph 0.545 g (0.005 mol) |

TABLE 4

| Synthesis example | Resin liquid | Amine component | Acid component | Terminal blocking agent |
|---|---|---|---|---|
| 81 | D1 | 2,2'-bis(trifluoromethyl)-3,3'-dihydroxybenzidine 17.6 g (0.05 mol) | isophthaloyl dichloride 8.12 g (0.04 mol) | NA 3.28 g (0.02 mol) |
| 82 | D2 | 2,2'-bis(trifluoromethyl)-3,3'-dihydroxybenzidine 17.6 g (0.05 mol) | terephthalic acid chloride 8.12 g (0.04 mol) | NA 3.28 g (0.02 mol) |
| 83 | D3 | TFMB 16.0 g (0.05 mol) | isophthaloyl dichloride 8.12 g (0.04 mol) | NA 3.28 g (0.02 mol) |
| 84 | D4 | HAB 10.8 g (0.05 mol) | isophthaloyl dichloride 8.12 g (0.04 mol) | NA 3.28 g (0.02 mol) |
| 85 | D5 | 2,2'-bis(trifluoromethyl)-3,3'-dihydroxybenzidine 17.6 g (0.05 mol) | diphenyletherdicarboxylic acid diimidazolide 14.32 g (0.04 mol) | NA 3.28 g (0.02 mol) |

TABLE 5-1

| | Resin | Linear thermal expansion coefficient (ppm/° C.) | Absorbance (/μm) | Alkali developing speed (nm/min) | Residual stress (Mpa) |
|---|---|---|---|---|---|
| Example 1 | A1 | 7 | 0.11 | >50000 | 6 |
| Example 2 | A2 | 10 | 0.06 | >50000 | 11 |
| Example 3 | A3 | 12 | 0.03 | >50000 | 16 |
| Example 4 | A4 | 16 | 0.02 | >50000 | 17 |
| Example 5 | A5 | 22 | 0.01 | >50000 | 18 |
| Example 6 | A6 | 20 | 0.02 | >50000 | 22 |
| Example 7 | A7 | 35 | 0.01 | >50000 | 37 |
| Example 8 | A8 | 12 | 0.06 | >50000 | 15 |
| Example 9 | A9 | 30 | 0.06 | >50000 | 31 |
| Example 10 | A10 | 30 | 0.03 | >50000 | 31 |
| Example 11 | A11 | 35 | 0.01 | >50000 | 37 |

TABLE 5-1-continued

| | Resin | Linear thermal expansion coefficient (ppm/° C.) | Absorbance (/μm) | Alkali developing speed (nm/min) | Residual stress (Mpa) |
|---|---|---|---|---|---|
| Example 12 | A12 | 37 | 0.04 | >50000 | 39 |
| Example 13 | A13 | 40 | 0.06 | >50000 | 43 |
| Example 14 | A14 | 27 | 0.06 | >50000 | 30 |
| Example 15 | A15 | 27 | 0.04 | >50000 | 30 |
| Example 16 | A16 | 20 | 0.09 | >50000 | 25 |
| Example 17 | A17 | 27 | 0.09 | >50000 | 30 |
| Example 18 | A18 | 20 | 0.06 | >50000 | 18 |
| Example 19 | A19 | 20 | 0.07 | >50000 | 18 |
| Example 20 | A20 | 20 | 0.06 | >50000 | 18 |
| Comparative Example 1 | A21 | 13 | 0.02 | >50000 | 20 |
| Comparative Example 2 | A22 | 6 | 0.4 | >50000 | 10 |
| Comparative Example 3 | A23 | 45 | 0.04 | >50000 | 43 |
| Comparative Example 4 | A24 | 45 | 0.05 | >50000 | 43 |
| Comparative Example 5 | A25 | 40 | 0.4 | >50000 | 45 |
| Comparative Example 6 | A26 | 40 | 0.4 | >50000 | 45 |
| Example 21 | B1 | 7 | 0.13 | 4000 | 6 |
| Example 22 | B2 | 10 | 0.07 | 14000 | 11 |
| Example 23 | B3 | 12 | 0.04 | 22000 | 16 |
| Example 24 | B4 | 16 | 0.02 | 26000 | 17 |
| Example 25 | B5 | 22 | 0.01 | 32000 | 18 |
| Example 26 | B6 | 20 | 0.02 | 30000 | 22 |
| Example 27 | B7 | 35 | 0.01 | 24000 | 37 |
| Example 28 | B8 | 12 | 0.07 | 24000 | 15 |
| Example 29 | B9 | 30 | 0.07 | 30000 | 31 |
| Example 30 | B10 | 30 | 0.04 | 30000 | 31 |
| Example 31 | B11 | 35 | 0.01 | 32000 | 37 |
| Example 32 | B12 | 37 | 0.04 | 34000 | 39 |
| Example 33 | B13 | 40 | 0.07 | 40000 | 43 |
| Example 34 | B14 | 28 | 0.07 | 200 | 30 |
| Example 35 | B15 | 27 | 0.05 | 10000 | 30 |
| Example 36 | B16 | 20 | 0.11 | 200 | 25 |
| Example 37 | B17 | 27 | 0.11 | 10000 | 30 |
| Example 38 | B18 | 20 | 0.07 | 4000 | 18 |
| Example 35 | B19 | 20 | 0.08 | 8000 | 18 |
| Example 40 | B20 | 20 | 0.07 | 4000 | 18 |
| Comparative Example 7 | B21 | 13 | 0.02 | 1000 | 20 |
| Comparative Example 8 | B22 | 6 | 0.45 | 200 | 10 |
| Comparative Example 9 | B23 | 45 | 0.04 | 8000 | 43 |
| Comparative Example 10 | B24 | 45 | 0.06 | 1000 | 43 |
| Comparative Example 11 | B25 | 40 | 0.45 | 6000 | 45 |
| Comparative Example 12 | B26 | 40 | 0.45 | 4000 | 45 |

TABLE 5-2

| | Resin | Linear thermal expansion coefficient (ppm/° C.) | Absorbance (/μm) | Alkali developing speed (nm/min) | Residual stress (Mpa) |
|---|---|---|---|---|---|
| Example 41 | C1 | 7 | 0.18 | 2000 | 5 |
| Example 42 | C2 | 10 | 0.1 | 7000 | 9 |
| Example 43 | C3 | 12 | 0.05 | 11000 | 13 |
| Example 44 | C4 | 16 | 0.03 | 13000 | 14 |
| Example 45 | C5 | 22 | 0.01 | 16000 | 15 |
| Example 46 | C6 | 20 | 0.03 | 15000 | 18 |
| Example 47 | C7 | 35 | 0.02 | 12000 | 30 |
| Example 48 | C8 | 12 | 0.1 | 12000 | 12 |
| Example 49 | C9 | 30 | 0.1 | 15000 | 25 |
| Example 50 | C10 | 30 | 0.05 | 15000 | 25 |
| Example 51 | C11 | 35 | 0.02 | 16000 | 30 |
| Example 52 | C12 | 37 | 0.06 | 17000 | 32 |
| Example 53 | C13 | 40 | 0.1 | 20000 | 35 |
| Example 54 | C14 | 27 | 0.1 | 100 | 24 |
| Example 55 | C15 | 27 | 0.07 | 5000 | 24 |
| Example 56 | C16 | 20 | 0.15 | 100 | 20 |
| Example 57 | C17 | 27 | 0.15 | 5000 | 24 |
| Example 58 | C18 | 20 | 0.1 | 2000 | 15 |
| Example 59 | C19 | 20 | 0.12 | 4000 | 15 |
| Example 60 | C20 | 20 | 0.1 | 2000 | 15 |
| Comparative Example 13 | C21 | 45 | 0.06 | 4000 | 35 |
| Comparative Example 14 | C22 | 13 | 0.03 | 0 | 17 |
| Example 61 | D1 | 40 (heat treatment at 250° C.) 20 (heat treatment at 320° C.) | 0.05 | 22000 | 48 (heat treatment at 250° C.) 40 (heat treatment at 320° C.) |
| Example 62 | D2 | 38 (heat treatment at 250° C.) 18 (heat treatment at 320° C.) | 0.2 | 17000 | 48 (heat treatment at 250° C.) 40 (heat treatment at 320° C.) |

TABLE 5-2-continued

| | Resin | Linear thermal expansion coefficient (ppm/° C.) | Absorbance (/μm) | Alkali developing speed (nm/min) | Residual stress (Mpa) |
|---|---|---|---|---|---|
| Comparative Example 15 | D3 | 50 (heat treatment at 210° C.)<br>25 (heat treatment at 320° C.) | 0.02 | 0 | 55 (heat treatment at 250° C.)<br>45 (heat treatment at 320° C.) |
| Comparative Example 16 | D4 | 45 (heat treatment at 250° C.)<br>20 (heat treatment at 320° C.) | 0.38 | 100 | 48 (heat treatment at 250° C.)<br>40 (heat treatment at 320° C.) |
| Example 63 | D5 | 50 (heat treatment at 250° C.)<br>35 (heat treatment at 320° C.) | 0.07 | 9000 | 53 (heat treatment at 250° C.)<br>45 (heat treatment at 320° C.) |

TABLE 6

| | Resin | Sensitivity (mJ/cm2) |
|---|---|---|
| Example 64 | B1 | 1050 |
| Example 65 | B2 | 850 |
| Example 66 | B3 | 700 |
| Example 67 | B4 | 650 |
| Example 68 | B5 | 650 |
| Example 69 | B6 | 650 |
| Example 70 | B7 | 650 |
| Example 71 | B8 | 850 |
| Example 72 | B9 | 850 |
| Example 73 | B10 | 700 |
| Example 74 | B11 | 650 |
| Example 75 | B12 | 750 |
| Example 76 | B13 | 850 |
| Example 77 | B14 | 850 |
| Example 78 | B15 | 800 |
| Example 79 | B16 | 1000 |
| Example 80 | B17 | 1000 |
| Example 81 | B18 | 850 |
| Example 82 | B19 | 900 |
| Example 83 | B20 | 850 |
| Comparative Example 17 | B21 | Not processable |
| Comparative Example 18 | B22 | 2000 |
| Comparative Example 19 | B23 | 450 |
| Comparative Example 20 | B24 | 500 |
| Comparative Example 21 | B25 | Not processable |
| Comparative Example 22 | B26 | Not processable |
| Example 84 | C1 | 1000 |
| Example 85 | C2 | 700 |
| Example 86 | C3 | 500 |
| Example 87 | C4 | 400 |
| Example 88 | C5 | 350 |
| Example 89 | C6 | 400 |
| Example 90 | C7 | 350 |
| Example 91 | C8 | 700 |
| Example 92 | C9 | 700 |
| Example 93 | C10 | 500 |
| Example 94 | C11 | 350 |
| Example 95 | C12 | 500 |
| Example 96 | C13 | 650 |
| Example 97 | C14 | 600 |
| Example 98 | C15 | 550 |
| Example 99 | C16 | 800 |
| Example 100 | C17 | 800 |
| Example 101 | C18 | 650 |
| Example 102 | C19 | 700 |
| Example 103 | C20 | 650 |
| Comparative Example 23 | C21 | 500 |
| Comparative Example 24 | C22 | Not processable |
| Example 104 | D1 | 500 |
| Example 105 | D2 | 1000 |
| Comparative Example 25 | D3 | Not processable |
| Comparative Example 26 | D4 | 2000 |
| Example 106 | D5 | 400 |

5,5'-dihydroxyl-4,4'-diaminobiphenyl derivative

The reaction yield corresponds to a molar percentage. Both solvents and catalysts used in the examples are purchased from suppliers of reagents, such as national medicine, Aldrich, TCI and Alfa, and are used directly for reaction without post-treatment. A structure of a reaction product is confirmed by nuclear magnetic resonance spectroscopy, and a nuclear magnetic resonance apparatus used is JEOL (400 MHz). A purity of the reaction product is measured using high performance liquid chromatography, the high performance liquid chromatography used is SHIMADZU Prominence, and a chromatographic column is YMC Pack Ph.

Example 107

2,2'-ditrifluoromethyl-4,4'-diaminobiphenyl (80.0 g, 0.25 mol) and ethylacetate (800 mL) were added to a conical flask, and air in the flask was replaced three times with nitrogen gas. The reaction flask was placed and stirred in an ice bath (−20° C.). Then, liquid bromine (26.2 mL, 0.51 mol) was dropped in the reaction flask, and liquid bromine was dropped while controlling the reaction temperature to 20° C. or less. The reaction was traced by high performance liquid chromatography, stirring was stopped when the raw material content was less than 3%, saturated sodium carbonate solution was gradually added to the reaction flask, and the pH value was adjusted to neutral. An organic phase was separated, washed with water (500 mL×2), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 106.5 g of white solid 2,2'-ditrifluoromethyl-5,5'-dibromo-4,4'-diaminobiphenyl (yield 90%, purity 96%).

[Chemical Formula 33]

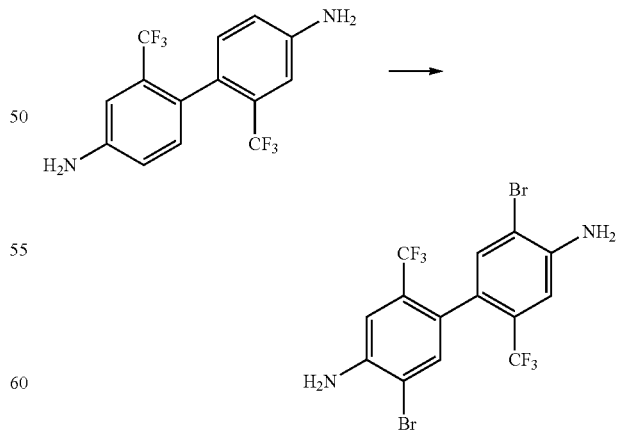

2,2'-ditrifluoromethyl-5,5'-dibromo-4,4'-diaminobiphenyl (95.6 g, 0.2 mol) obtained by the above production process and tetrahydrofuran (500 mL) were added to a conical flask, and then benzoyl chloride (56.0 g, 0.4 mol) was added. The reaction flask was placed and stirred in an oil bath kept at a constant temperature of 40° C. and left overnight. The reaction was traced by high performance liquid chromatography, and stirring was stopped when the raw material content was less than 3%. Ethanol and water were added to the reaction solution, and tetrahydrofuran was removed by distillation under reduced pressure to obtain a white floating solution. Subsequently, filtration was carried out, and the filtrated solid was washed with 50 ml of ethanol and then placed and dried in a vacuum oven to obtain 130.2 g of white solid 2,2'-ditrifluoromethyl-5,5'-dibromo-4,4'-dibenzamidebiphenyl (yield 94.9%, purity 96%).

[Chemical Formula 34]

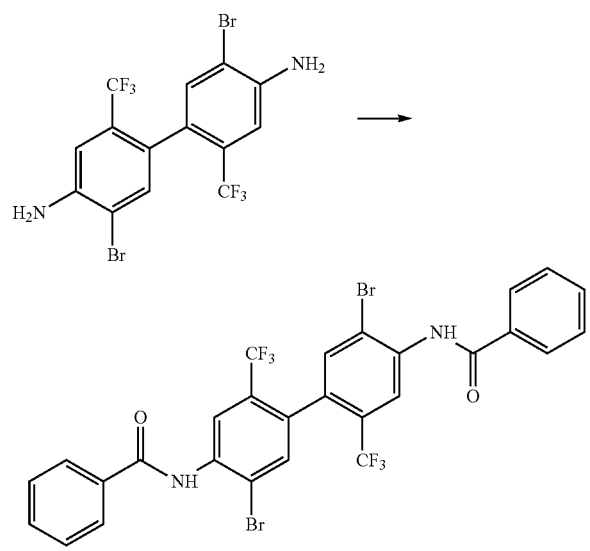

2,2'-ditrifluoromethyl-5,5'-dibromo-4,4'-dibenzamidebiphenyl (68.6 g, 0.10 mol) obtained by the above production process, copper iodide (I) (1.91 g, 0.01 mol), N,N'-dimethylethylenediamine (1.76 g, 0.02 mol), potassium phosphate (92.8 g, 0.4 mol) and toluene (600 mL) were added to a conical flask, and the mixture was replaced three times with nitrogen gas. The reaction was carried out in an oil bath at 100° C. and traced by high performance liquid chromatography, and stirring was stopped when the raw material content was less than 3%. The reaction was cooled, 1 L of toluene was added, and the mixture was decolorized with activated charcoal. After filtration, the filtrate was concentrated and then recrystallized to obtain 31.5 g of white solid 2,2'-diphenyl-5,5'-ditrifluoromethyl-[6,6']dibenzoxazole (yield 60%, purity 98%).

[Chemical Formula 35]

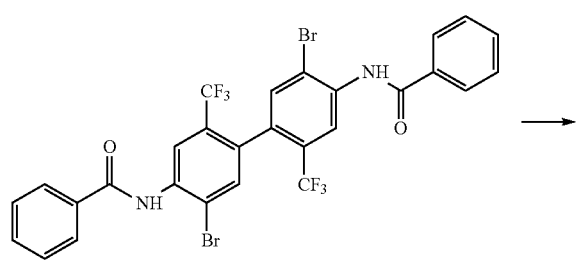

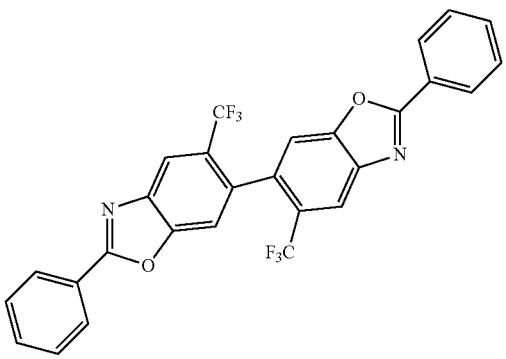

2,2'-dimethyl-5,5'-ditrifluoromethyl-[6,6']dibenzoxazole (80.0 g, 0.2 mol) obtained by the preparation process, 36.5% hydrochloric acid (250 ml) and ethanol (1.25 L) were added to a conical flask and stirred in an oil bath kept at a constant temperature of 60° C. The reaction was traced by high performance liquid chromatography, and stirring was stopped when the raw material content was less than 3%. Water was added to the reaction liquid, ethanol was removed by distillation under reduced pressure, and the pH value was adjusted to be more than 3. Filtration was carried out, and the filtrated solid was washed with 100 ml of ethylacetate and then dried in a vacuum oven to obtain 63.2 g of white solid 2,2'-ditrifluoromethyl-5,5'-dihydroxyl-4,4'-diaminobiphenyl (yield 90%, purity 98%).

[Chemical Formula 36]

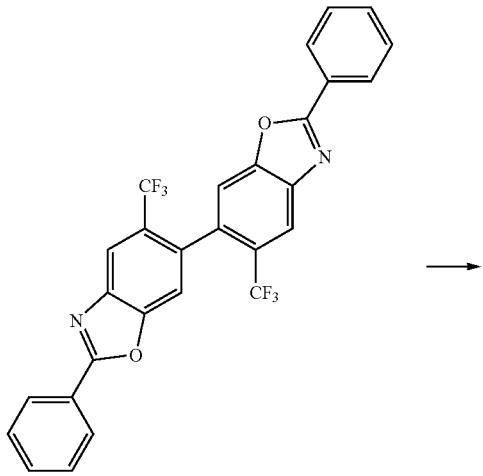

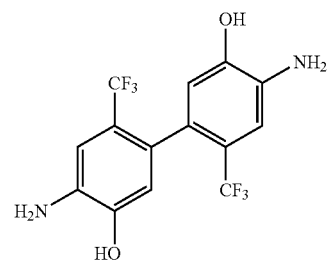

$^1$H NMR (400 MHz, d-DMSO): 9.81 (s, 2H), 6.90 (s, 2H), 6.47 (s, 2H), 4.92 (s, 4H)

Example 108

2,2'-ditrifluoromethyl-4,4'-diaminobiphenyl (32.0 g, 0.10 mol) and dioxane (300 mL) were added to a conical flask, and the mixture was replaced three times with nitrogen gas. The reaction flask was placed and stirred in an ice bath. Then, after N-bromosuccinimide (NBS) (35.6 g, 0.20 mol) was added to the reaction flask in several portions, the temperature was raised to 60° C., and stirring was carried out. The reaction was traced by high performance liquid chromatography, and stirring was stopped when the raw material content was less than 3%. A saturated sodium carbonate solution was gradually added to the reaction flask, and the pH value was adjusted to neutral. An organic phase was separated, washed with water (200 mL×2), dried over anhydrous sodium sulfate, and filtered. Then, an organic solvent was removed to obtain a crude product reddish orange solid. Subsequently, petroleum ether/ethylacetate (60 ml/2 ml) was added to the crude product, and the mixture was stirred at room temperature for 30 minutes and filtered to obtain 37.5 g of white solid 2,2'-ditrifluoromethyl-5,5'-dibromo-4,4'-diaminobiphenyl (yield 78%, purity 95%).

[Chemical Formula 37]

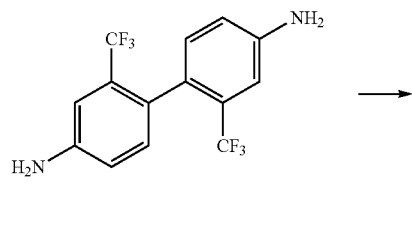

2,2'-ditrifluoromethyl-5,5'-dibromo-4,4'-diaminobiphenyl (95.6 g, 0.2 mol) obtained by the above production process and dichloromethane (500 mL) were added to a conical flask, and then acetic anhydride (51.0 g, 0.5 mol) was added. The reaction flask was placed and stirred in an ethanol bath kept at a constant temperature of 10° C. and left overnight. The reaction was traced by high performance liquid chromatography, and stirring was stopped when the raw material content was less than 3% to obtain a white floating solution. The reaction solution was filtered, and the filtrated solid was washed twice with 50 ml of dichloromethane, washed twice with 100 ml of water, and placed and dried in a vacuum oven to obtain 106.2 g of white solid 2,2'-ditrifluoromethyl-5,5'-dibromo-4,4'-diformamidebiphenyl (yield 94.3%, purity 98%).

[Chemical Formula 38]

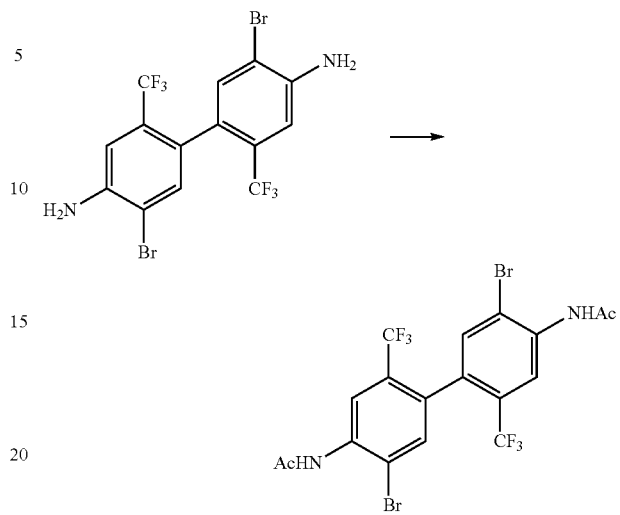

2,2'-ditrifluoromethyl-5,5'-dibromo-4,4'-diformamidebiphenyl (112.4 g, 0.20 mol) obtained by the above production process, copper iodide (I) (3.82 g, 0.02 mol), N,N'-dimethylethylenediamine (3.52 g, 0.04 mol), potassium phosphate (110.4 g, 0.8 mol) and xylene (1200 mL) were added to a conical flask, and the mixture was replaced three times with nitrogen gas. The reaction was carried out in an oil bath at 140° C. and traced by high performance liquid chromatography, and stirring was stopped when the raw material content was less than 3%. The reaction was cooled, 1 L of toluene was added, and the mixture was decolorized with activated charcoal and filtered. The filtrate was concentrated and then recrystallized to obtain 48.1 g of white solid 2,2'-dimethyl-5,5'-ditrifluoromethyl-[6,6']dibenzoxazole (yield 60%, purity 97%).

[Chemical Formula 39]

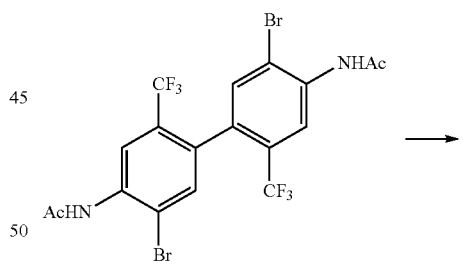

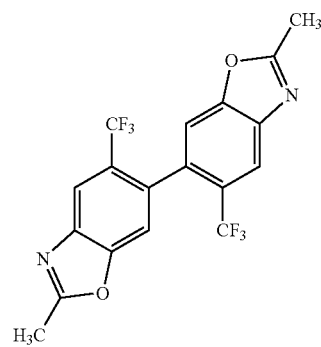

2,2'-dimethyl-5,5'-ditrifluoromethyl-[6,6']dibenzoxazole (80.0 g, 0.2 mol) obtained by the production process, 36.5% hydrochloric acid (250 ml) and ethanol (1.25 L) were added to a conical flask and stirred in an oil bath kept at a constant temperature of 60° C. The reaction was traced by high performance liquid chromatography, and stirring was stopped when the raw material content was less than 3%. Water was added to the reaction liquid, ethanol was removed by distillation under reduced pressure, and the pH value was adjusted to be more than 3. Filtration was carried out, and the filtrated solid was washed with 100 ml of ethylacetate and then dried in a vacuum oven to obtain 63.2 g of white solid 2,2'-ditrifluoromethyl-5,5'-dihydroxyl-4,4'-diaminobiphenyl (yield 90%, purity 98%).

[Chemical Formula 40]

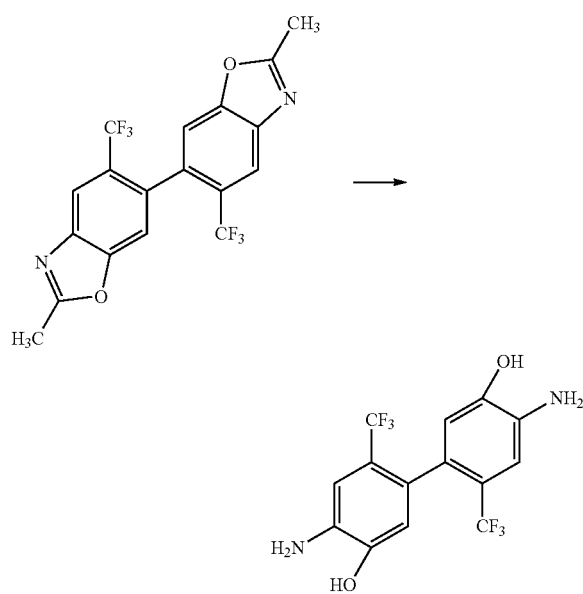

$^1$H NMR (400 MHz, d-DMSO): 9.81 (s, 2H), 6.90 (s, 2H), 6.47 (s, 2H), 4.92 (s, 4H).

Example 109

2,2'-ditrifluoromethyl-5,5'-dibromo-4,4'-diaminobiphenyl (95.6 g, 0.2 mol) obtained by the above production process and dichloromethane (500 mL) were added to a conical flask, and triethylamine (71.8 ml, 0.514 mol) and pivaloyl chloride (63.0 ml, 0.514 mol) were added. The reaction flask was placed and stirred in an oil bath kept at a constant temperature of 40° C. and left overnight. The reaction was traced by high performance liquid chromatography, and stirring was stopped when the raw material content is less than 3%. A saturated sodium carbonate aqueous solution (200 ml) was added and stirred for 1 hour. An organic layer was washed with water and saturated brine, dried over anhydrous sodium sulfate, and concentrated under reduced pressure. Washing was carried out with a mixed solvent of petroleum ether (200 ml) and ethylacetate (10 ml), and filtration was carried out. The filtrate was placed and dried in a vacuum oven to obtain 130.2 g of white solid 2,2'-ditrifluoromethyl-5,5'-dibromo-4,4'-dibutylamidebiphenyl (yield 94.9%, purity 97%).

[Chemical Formula 41]

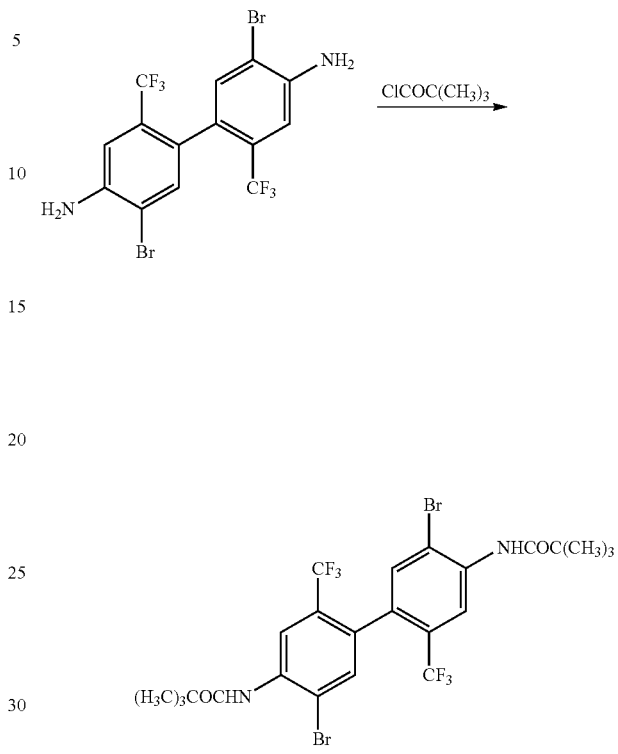

2,2'-ditrifluoromethyl-5,5'-dibromo-4,4'-dibutylamide biphenyl (103.5 g, 0.161 mol) obtained by the above production process, copper bromide (I) (2.30 g, 0.161 mol), N,N'-dimethylethylenediamine (2.85 g, 0.0322 mol), potassium phosphate (102.4 g, 0.483 mol), toluene (1000 mL), and dioxane (100 ml) were added to a conical flask, and the mixture was replaced three times with nitrogen gas. The reaction was carried out in an oil bath at 120° C. and traced by high performance liquid chromatography, and stirring was stopped when the raw material content was less than 3%. The reaction was cooled, and filtration was carried out. An organic layer was washed with water, dried over anhydrous sodium sulfate, and concentrated under reduced pressure to obtain 49.8 g of white solid 2,2'-di(tert-butyl)-5,5'-ditrifluoromethyl-[6,6']dibenzoxazole (yield 65%, purity 99%)

[Chemical Formula 42]

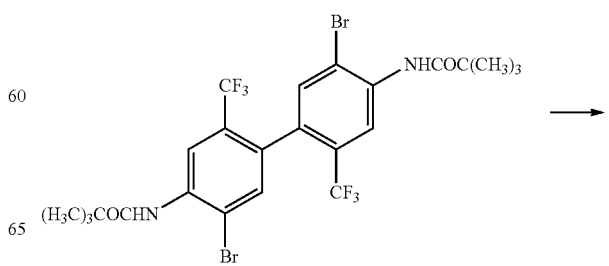

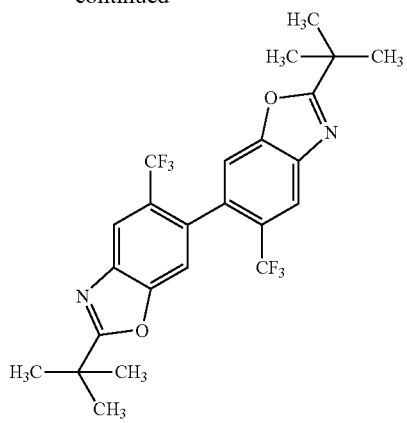

2,2'-di(tert-butyl)-5,5'-ditrifluoromethyl-[6,6']dibenzoxazole (48.4 g, 0.1 mol) obtained by the production process, 36.5% hydrochloric acid (250 ml) and ethanol (300 L) were added to a conical flask and stirred in an oil bath kept at a constant temperature of 100° C. The reaction was traced by high performance liquid chromatography, and stirring was stopped when the raw material content was less than 3%. Water was added to the reaction liquid, ethanol was removed by distillation under reduced pressure, and the pH value was adjusted to be more than 3. Filtration was carried out, and the filtrated solid was washed with 100 ml of ethylacetate and then dried in a vacuum oven to obtain 31.6 g of white solid 2,2'-ditrifluoromethyl-5,5'-dihydroxyl-4,4'-diaminobiphenyl (yield 90%, purity 98%).

[Chemical Formula 43]

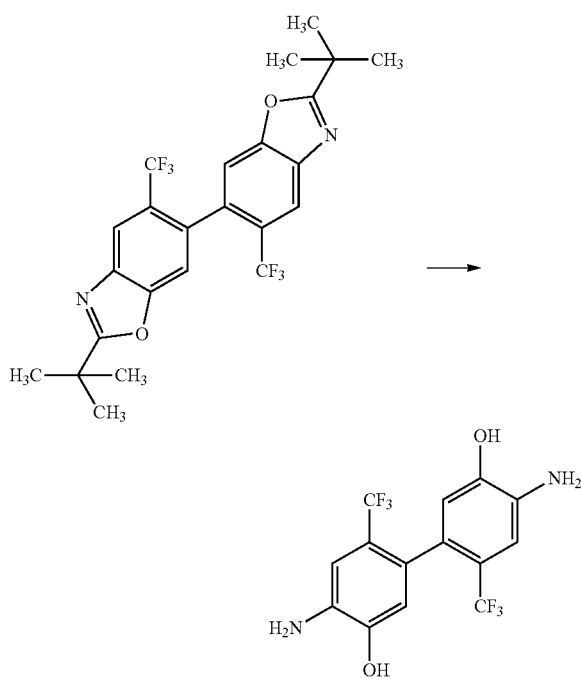

$^1$H NMR (400 MHz, d-DMSO): 9.81 (s, 2H), 6.90 (s, 2H), 6.47 (s, 2H), 4.92 (s, 4H).

<Dibromobiphenyl Derivative>

Reaction process measurement: Measurement is carried out by high performance liquid chromatography, the model number is SHIMADZU LC-20AD, and chromatography column is YMC-Pack Ph (250×4.6 mml·D).

Purity: Measurement is carried out by high performance liquid chromatography, the model number is SHIMADZU LC-20AD, and chromatography column is YMC-Pack Ph (250×4.6 mml·D). Structure identification: nuclear magnetic resonance apparatus, JEOL (400 MHz), solvent is deuterated chloroform or dimethylsulfoxide-d6.

Yield: molar yield, it can be calculated after weighing.

Materials and Reagents Used in Comparative Examples and Examples:

2,2'-ditrifluoromethyl-4,4'-diaminobiphenyl: purchased from J & K Chemical;

Liquid bromine: purchased from the national medicine group;

N-bromosuccinimide: purchased from the national medicine group;

Solvent: purchased from the national medicine group.

In the present invention, a raw material biphenyl compound having a structure represented by the general formula (13) is dissolved in an aprotic solvent, a bromination reagent is added to a reaction flask under the condition of −30° C. to 60° C., and stirring is continuously carried out until almost no raw material remains. An alkaline aqueous solution is added to the reaction flask until it is neutral, and an organic phase is separated, washed with water, dried, and dissolved to obtain a crude product. The crude product is purified to obtain a dibromobiphenyl derivative as a final product. The yield of the reaction is a molar percentage.

Example 110

2,2'-ditrifluoromethyl-4,4'-diaminobiphenyl (80.0 g, 0.25 mol) and ethylacetate (800 mL) were added to a conical flask, and the mixture was replaced three times with nitrogen gas. The reaction flask was placed and stirred in an ice bath. Then, liquid bromine (26.2 mL, 0.51 mol) was dropped in the reaction flask and then successively stirred. The reaction was measured by high performance liquid chromatography, and stirring was stopped when the raw material content was less than 3%. A saturated sodium carbonate solution was gradually added to the reaction flask, and the pH value was adjusted to neutral. An organic phase was separated, washed with water (500 mL each time, washed twice), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 106.5 g of white solid 2,2'-ditrifluoromethyl-4,4'-diamino-5,5'-dibromobiphenyl (yield 90%, purity 96%).

[Chemical Formula 44]

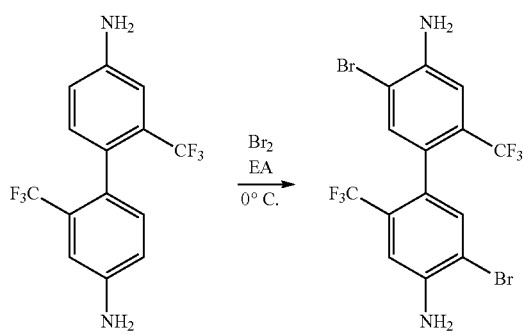

$^1$H NMR (400 MHz, DMSO-d$_6$) δ 5.88 (s, 4H), 7.15 (s, 2H), 7.26 (s, 2H)

Example 111

2,2'-ditrifluoromethyl-4,4'-diaminobiphenyl (32.0 g, 0.10 mol) and 1,4-dioxane (300 mL) were added to a conical flask, and the mixture was replaced three times with nitrogen gas. The reaction flask was placed and stirred in an ice bath. Then, N-bromosuccinimide (NBS) (35.6 g, 0.20 mol) was added to the reaction flask in several portions and then successively stirred. The reaction was traced by high performance liquid chromatography, and stirring was stopped when the raw material content was 3% or less. A sodium hydroxide solution was gradually added to the reaction flask, and the pH value was adjusted to neutral. Then, an organic phase was separated by adding ethylacetate (300 mL), washed with saturated brine (200 mL each time, washed twice), washed with water (200 mL), dried over anhydrous sodium sulfate, and filtered. Then, an organic solvent was removed to obtain a crude product reddish orange solid. Subsequently, petroleum ether/ethylacetate (60 ml/2 ml) was added to the crude product, and the mixture was stirred at room temperature for 30 minutes and filtered to obtain 33.5 g of white solid 2,2'-ditrifluoromethyl-4,4'-diamine-5,5'-dibromobiphenyl (yield 70%, purity 95%).

[Chemical Formula 45]

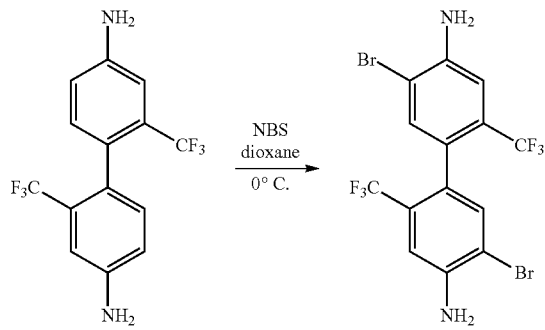

$^1$H NMR (400 MHz, DMSO-d$_6$) δ 5.88 (s, 4H), 7.15 (s, 2H), 7.26 (s, 2H)

Example 112

2,2'-ditrifluoromethyl-4,4'-diacetamidobiphenyl (101.0 g, 0.25 mol) and tetrahydrofuran (500 mL) were added to a conical flask, and the mixture was replaced three times with nitrogen gas. The reaction flask was placed and stirred in a low temperature reaction tank at −20° C. Then, liquid bromine (26.2 mL, 0.51 mol) was dropped in the reaction flask and then successively stirred. The reaction was traced by high performance liquid chromatography, and stirring was stopped when the raw material content was 3% or less. A saturated sodium carbonate solution was gradually added to the reaction flask, and the pH value was adjusted to neutral. Then, an organic phase was separated by adding ethylacetate (500 mL), washed with saturated brine (500 mL each time, washed twice), washed with water (200 mL), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 119.6 g of white solid 2,2'-ditrifluoromethyl-4,4'-diacetamide-5,5'-dibromobiphenyl (yield 85%, purity 96%).

[Chemical Formula 46]

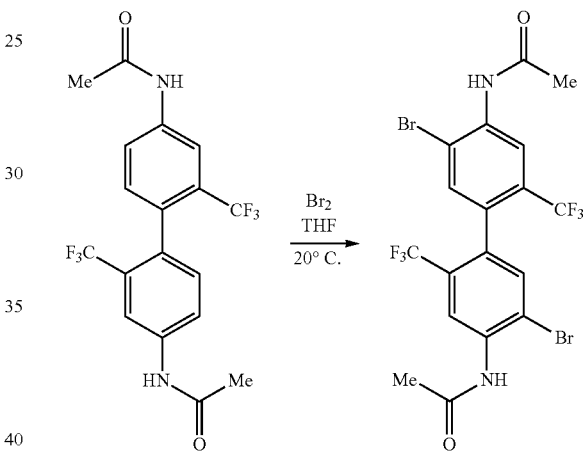

$^1$H NMR (400 MHz, DMSO-d$_6$) δ 2.16 (s, 6H), 7.80 (s, 2H), 8.19 (s, 2H), 9.76 (s, 2H)

Example 113

2,2'-ditrifluoromethyl-4,4'-di(phthalimide)biphenyl (145.0 g, 0.25 mol) and propyleneglycolmethyletheracetate (500 mL) were added to a conical flask, and the mixture was replaced three times with nitrogen gas and stirred at room temperature. Then, liquid bromine (26.2 mL, 0.51 mol) was dropped in the reaction flask and then successively stirred. The reaction was traced by high performance liquid chromatography, and stirring was stopped when the raw material content was 3% or less. A saturated sodium carbonate solution was gradually added to the reaction flask, and the pH value was adjusted to neutral. Then, an organic phase was separated, washed with water (300 mL each time, washed twice), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 166.0 g of white solid 2,2'-ditrifluoromethyl-4,4'-di(phthalimide)-5,5'-dibromobiphenyl (yield 90%, purity 95%).

[Chemical Formula 47]

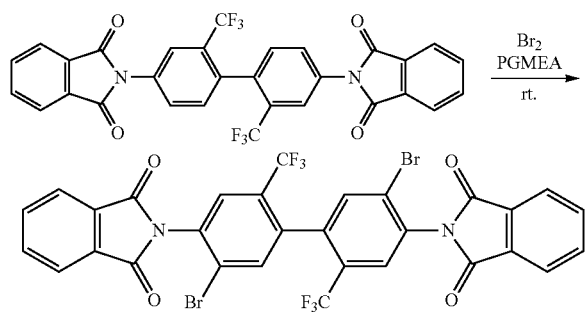

$^1$H NMR (400 MHz, DMSO-d$_6$) δ 7.98-7.99 (m, 4H), 8.06-8.07 (m, 4H), 8.24 (s, 2H), 8.30 (s, 2H)

Example 114

2,2'-ditrifluoromethyl-4,4'-di(ditertiarybutoxidedicarboximide)biphenyl (180.0 g, 0.25 mol) and butylacetate (500 mL) were added to a conical flask, and the mixture was replaced three times with nitrogen gas and placed and stirred in a low temperature reaction groove at −30° C. Then, liquid bromine (26.2 mL, 0.51 mol) was dropped in the reaction flask and then successively stirred. The reaction was traced by high performance liquid chromatography, and stirring was stopped when the raw material content was 3% or less. A saturated sodium carbonate solution was gradually added to the reaction flask, and the pH value was adjusted to neutral. Then, an organic phase was separated, washed with water (500 mL each time, washed twice), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 177.6 g of white solid 2,2'-ditrifluoromethyl-4,4'-di(ditertiarybutoxidedicarboximide)-5,5'-dibromobiphenyl (yield 81%, purity 95%).

[Chemical Formula 48]

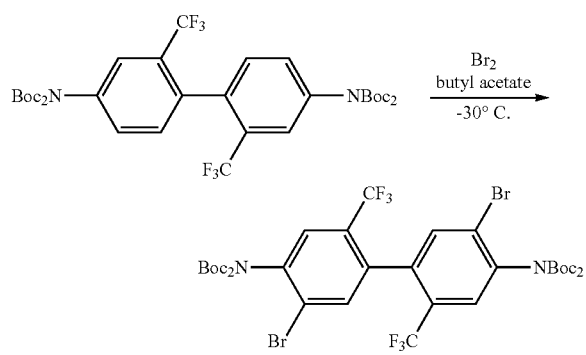

$^1$H NMR (400 MHz, DMSO-d$_6$) δ 1.31-1.41 (m, 18H), 7.88 (s, 1H), 8.05 (s, 1H)

Example 115

2,2'-ditrifluoromethyl-4,4'-di(ditertiarybutoxidecarbamide)biphenyl (130.0 g, 0.25 mol) and butylacetate (500 mL) were added to a conical flask, and the mixture was replaced three times with nitrogen gas and placed and stirred in a low temperature reaction tank at −30° C. Then, liquid bromine (26.2 mL, 0.51 mol) was dropped in the reaction flask and then successively stirred. The reaction was traced by high performance liquid chromatography, and stirring was stopped when the raw material content was 3% or less. A saturated sodium carbonate solution was gradually added to the reaction flask, and the pH value was adjusted to neutral. Then, an organic phase was separated, washed with water (500 mL each time, washed twice), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 141.1 g of white solid 2,2'-ditrifluoromethyl-4,4'-di(ditertiarybutoxidecarbamide)-5,5'-dibromobiphenyl (yield 83%, purity 95%).

[Chemical Formula 49]

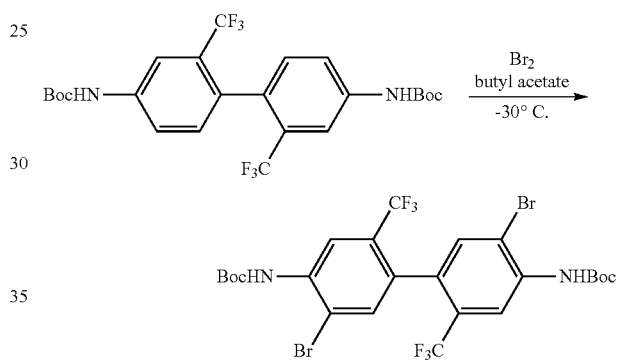

$^1$H NMR (400 MHz, DMSO-d$_6$) δ 1.49 (s, 18H), 7.73 (s, 1H), 8.04 (s, 1H), 8.92 (s, 1H)

Example 116

2,2'-ditrifluoromethyl-4,4'-diaminobiphenyl (32.0 g, 0.10 mol) and dichloromethane (300 mL) were added to a conical flask, and the mixture was replaced three times with nitrogen gas. The reaction flask was placed and stirred in an ice bath. Then, N-bromosuccinimide (NBS) (35.6 g, 0.20 mol) was added to the reaction flask in several portions and then successively stirred. While the reaction was traced by high performance liquid chromatography, N-bromosuccinimide (17.8 g, 0.10 mmol) was supplied and added, and stirring was stopped when the raw material content was 3% or less. A sodium hydroxide solution was gradually added to the reaction flask, and the pH value was adjusted to neutral. Then, an organic phase was separated, washed with water (200 mL each time, washed twice), dried over anhydrous sodium sulfate, and filtered. Then, an organic solvent was removed to obtain a crude product reddish orange solid. Subsequently, petroleum ether/ethylacetate (60 ml/2 ml) was added to the crude product, and the mixture was stirred at room temperature for 30 minutes and filtered to obtain 23.8 g of white solid 2,2'-ditrifluoromethyl-4,4'-diamino-5,5'-dibromobiphenyl (yield 50%, purity 95%).

[Chemical Formula 50]

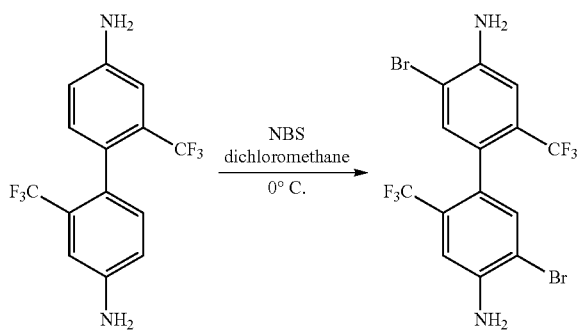

¹H NMR (400 MHz, DMSO-d₆) δ 5.88 (s, 4H), 7.15 (s, 2H), 7.26 (s, 2H)

Example 117

2,2'-ditrifluoromethyl-4,4'-diaminobiphenyl (32.0 g, 0.10 mol) and acetonitrile (300 mL) were added to a conical flask, and the mixture was replaced three times with nitrogen gas. The reaction flask was placed and stirred in an ice bath. Then, N-bromosuccinimide (NBS) (35.6 g, 0.20 mol) was added to the reaction flask in several portions and then successively stirred. While the reaction was traced by high performance liquid chromatography, NBS (8.9 g, 0.05 mol) was supplied and added, and stirring was stopped when the raw material content was 3% or less. A sodium hydroxide solution was gradually added to the reaction flask, and the pH value was adjusted to neutral. Then, an organic phase was separated by adding ethylacetate (300 mL), washed with saturated brine (200 mL each time, washed twice), washed with water (200 mL), dried over anhydrous sodium sulfate, and filtered. Then, an organic solvent was removed to obtain a crude product reddish orange solid. Subsequently, petroleum ether/ethylacetate (60 ml/2 ml) was added to the crude product, and the mixture was stirred at room temperature for 30 minutes and filtered to obtain 15.7 g of pale yellow solid 2,2'-ditrifluoromethyl-4,4'-diamino-5,5'-dibromobiphenyl (yield 33%, purity 95%).

[Chemical Formula 51]

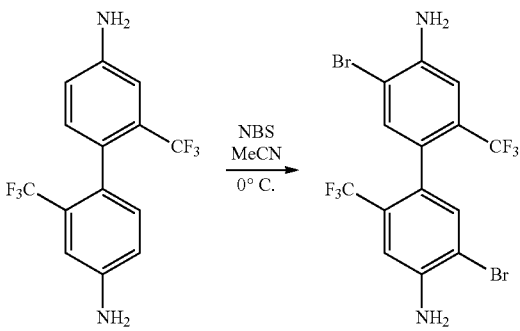

¹H NMR (400 MHz, DMSO-d₆) δ 5.88 (s, 4H), 7.15 (s, 2H), 7.26 (s, 2H)

Example 118

2,2'-dimethoxy-4,4'-dimethylbiphenyl (60.5 g, 0.25 mol) and ethylacetate (500 mL) were added to a conical flask, and the mixture was replaced three times with nitrogen gas. The reaction flask was stirred at room temperature. Then, liquid bromine (26.2 mL, 0.51 mol) was dropped in the reaction flask and then successively stirred. The reaction was traced by high performance liquid chromatography, and stirring was stopped when the raw material content was 3% or less. A saturated sodium carbonate solution was gradually added to the reaction flask, and the pH value was adjusted to neutral. Then, an organic phase was separated, washed with water (500 mL each time, washed twice), dried over anhydrous sodium sulfate, and filtered. Then, an organic solvent was removed to obtain a crude product yellow solid. Subsequently, petroleum ether/ethylacetate (150 ml/5 ml) was added to the crude product, and the mixture was stirred at room temperature for 30 minutes and filtered to obtain 94.3 g of white solid 2,2'-dimethoxy-4,4'-dimethyl-5,5'-dibromobiphenyl (yield 94%, purity 95%).

[Chemical Formula 52]

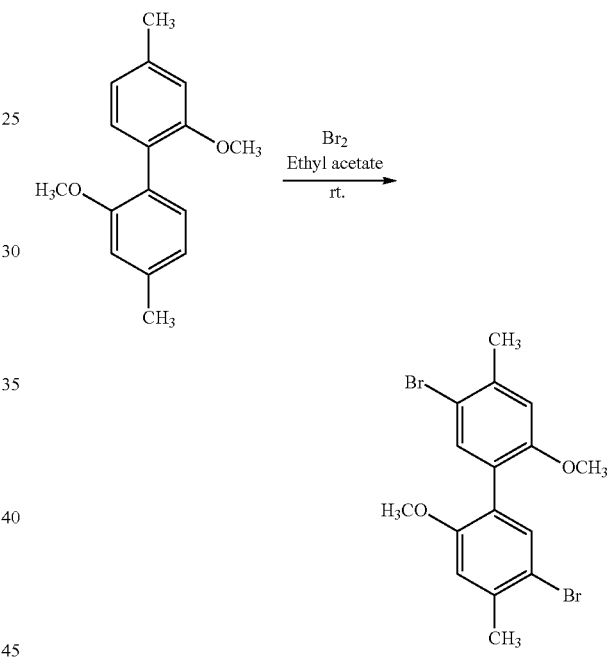

¹H NMR (400 MHz, CDCl₃) 2.39 (s, 6H), 3.80 (s, 6H), 6.79 (s, 2H), 7.39 (s, 2H)

Comparative Example 27

Acetic acid (50 mL), sodium acetate (1.3 g) and a raw material 1 (1.46 g, 3.78 mmol) were added to a conical flask, and the mixture was replaced three times with nitrogen gas and stirred at room temperature. Then, a mixed solution of liquid bromine Br₂ (0.4 mL, 7.76 mmol) and acetic acid (5 mL) was dropped in the reaction flask and then successively reacted at room temperature for 48 h. The reaction was traced by thin layer chromatography (TLC) (developing solvent: petroleum ether/ethyl acetate, 10 mL/1 mL), liquid bromine (0.4 mL) and acetic acid (5 mL) were supplied and added, followed by stirring for 24 h. Saturated sodium sulfite (5 mL) was added to the reaction solution and extracted with dichloromethane (70 mL each time, extracted five times). Organic phases were combined, washed with water, dried over anhydrous magnesium sulfate, and filtered. Then, an organic solvent was removed to obtain an oily substance.

The oily substance was recrystallized using dichloromethane to obtain 1.64 g (yield 80%) of a product 2.

[Chemical Formula 53]

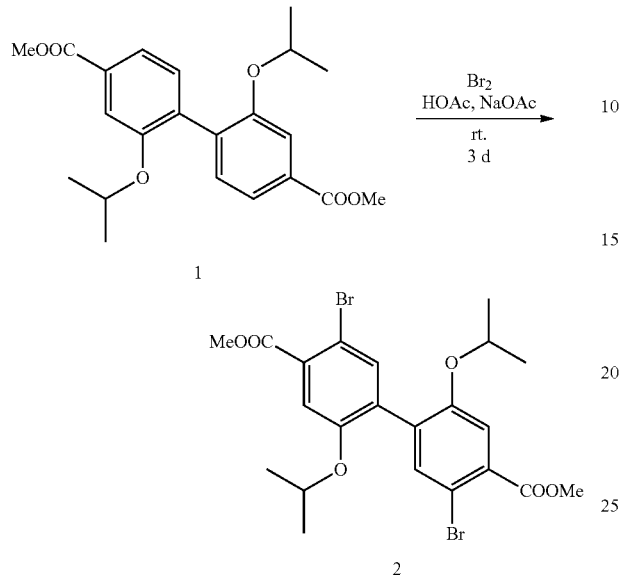

1H NMR (400 MHz, acetone-$d_6$) δ 1.24 (d, J=6.0 Hz, 12H), 3.96 (s, 6H), 4.65 (sept, J=6.1 Hz, 2H), 7.48 (s, 2H), 7.58 (s, 2H).

Comparative Example 28

100 ml of ethanol and 20.0 g (62.5 mmol) of 2,2'-ditrifluoromethylbenzidine were added to a conical flask, and the mixture was replaced three times with nitrogen gas. The reaction flask was placed and stirred in an ice bath. Then, 21.0 g (131.2 mmol) of bromine was dropped in the reaction flask and then stirred at room temperature for 1 h. Then, toluene was added, and an organic phase was washed three times with water, then washed twice each with a saturated sodium bicarbonate solution and water, dried, and filtered. Then, after an organic solvent was removed, recrystallization was carried out with normal hexane/toluene to obtain 11.5 g (yield 38.5%) of 2,2'-ditrifluoromethyl-4,4'-diamino-5,5'-dibromobiphenyl.

[Chemical Formula 54]

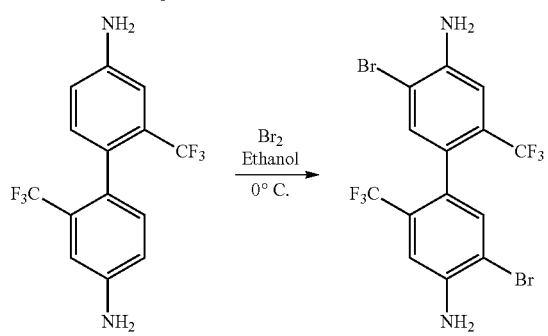

$^1$H NMR (500 MHz, CDCl$_3$) δ 4.33 (s, 4H), 7.05 (s, 2H), 7.32 (s, 2H).

DESCRIPTION OF REFERENCE SIGNS

1: Silicon wafer
2: Al pad
3: Passivation film
4: Insulating film
5: Metal (Cr, Ti, Ni, TiW, etc.) film
6: Metal (Al, Cu, Au, etc.) wiring
7: Insulating film
8: Barrier metal
9: Scribe line
10: Solder bump
11: Silicon wafer
12: Al pad
13: Passivation film
14: Insulating film
15: Adhesive film
16: Wire (Cu, Au, etc.)
21: Silicon wafer
22: Through electrode (Cu etc.)
23: Pad (Al, Cu, etc.)
24: Passivation film
25: Insulating film
26: Barrier metal
27: Solder bump
28: Adhesive film
29: Scribe line
31: TFT
32: Wiring
33: Insulating film
34: Flattening film
35: ITO
36: Substrate
37: Contact hole

The invention claimed is:
1. A resin comprising at least one selected from a polyimide, polyamideimide, polyimide precursor, and a copolymer thereof, wherein each of said polyimide, polyamideimide, polyimide precursor and the copolymer thereof is a resin having a structure of at least one selected from structures represented by the following general formulae (1), (3) and (4):

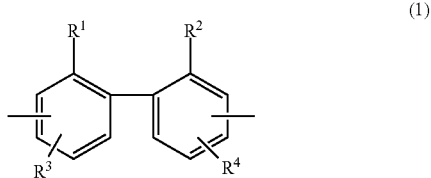
(1)

wherein, in the general formula (1), $R^1$ and $R^2$ each independently represents a halogen atom or a monovalent organic group having 1 to 3 carbon atoms,
$R^3$ and $R^4$ each represents a group selected from a hydroxyl group and a carboxyl group,

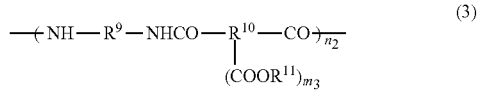
(3)

wherein, in the general formula (3), for $R^9$ and $R^{10}$:
i) $R^9$ represents a structure of general formula (1) or general formula (6), and $R^{10}$ is an organic group having 2 to 50 carbon atoms, or ii) $R^9$ is an organic group having 2 to 50 carbon atoms, and $R^{10}$ represents a structure of general formula (7), or iii) $R^9$ represents a structure selected of the general formula (1) or the general formula (6), and $R^{10}$ represents a structure of the general formula (7), $R^{11}$ represents hydrogen or an organic group having 1 to 10 carbon atoms, $m_3$ is an integer of 1 or 2, and $n_2$ represents a range of 10 to 100,000,

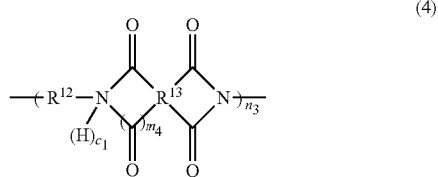

(4)

wherein, in the general formula (4), for $R^{12}$ and $R^{13}$:

i) $R^{12}$ represents a structure of the general formula (1) or general formula (6), and $R^{13}$ is an organic group having 2 to 50 carbon atoms, or ii) $R^{12}$ is an organic group having 2 to 50 carbon atoms, and $R^{13}$ represents a structure of general formula (7), or iii) $R^{12}$ represents a structure selected from the general formula (1) or the general formula (6), and $R^{13}$ represents a structure selected from the general formula (7), $m_4$ is an integer of 0 or 1, $c_1$ is an integer of 0 or 1, $c_1=1$ when $m_4=0$, and $c_1=0$ when $m_4=1$, and $n_3$ represents a range of 10 to 100,000,

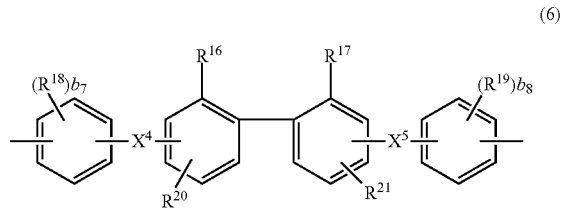

(6)

wherein, in the general formula (6), $R^{16}$ to $R^{19}$ each independently represents a halogen atom or a monovalent organic group having 1 to 3 carbon atoms, $R^{20}$ and $R^{21}$ each represents a group selected from a hydroxyl group and a carboxyl group, $X^4$ and $X^5$ each represents a structure selected from an amide bond and an azomethine bond, $b_7$ and $b_8$ are integers of 0 to 4,

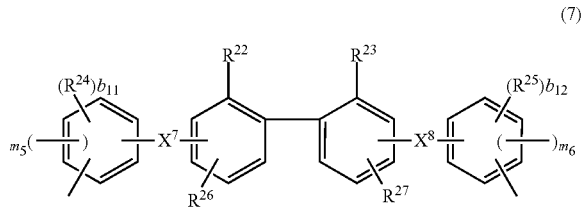

(7)

wherein, in the general formula (7), $R^{22}$ to $R^{25}$ each independently represents a halogen atom or a monovalent organic group having 1 to 3 carbon atoms, $R^{26}$ and $R^{27}$ each represents a group selected from a hydroxyl group and a carboxyl group, $X^7$ and $X^8$ each represents a structure selected from an amide bond and an azomethine bond, $b_{11}$ and $b_{12}$ are integers of 0 to 3, and $m_5$ and $m_6$ are integers of 0 or 1, provided that:

wherein when $R^{10}$ of the general formula (3) represents a structure of the general formula (7), $m_5+m_6=1$ when $m_3=1$, and $m_5+m_6=2$ when $m_3=2$; and wherein when $R^{13}$ of the general formula (4) represents a structure of the general formula (7), $m_5+m_6=1$ when $m_4=0$, and $m_5+m_6+2$ when $m_4=1$.

2. The resin according to claim 1, wherein the resin is a resin that forms a resin film having an absorbance at a wavelength of 365 nm per 1 µm thickness of 0.005 or more and 0.3 or less.

3. The resin according to claim 1, wherein an average linear thermal expansion coefficient of the resin at 50 to 200° C. measured after heat treatment of the resin at 250° C. is −10 to 40 ppm/° C.

4. The resin according to claim 1, wherein the resin forms a resin film which has a film thickness reduction rate of 10 nm/min or more and 30000 nm/min or less when immersed in a 2.38% tetramethylammonium hydroxide aqueous solution.

5. A resin composition comprising the resin according to claim 1.

6. The resin composition according to claim 5, comprising a photo acid generator or a photopolymerization initiator.

7. A process for producing a heat resistance coating film, comprising: coating the resin composition according to claim 5 onto a support substrate to form a coating film; drying the coating film to form a resin film; exposing the resin film; developing the exposed resin film; and applying heat treatment to the developed resin film.

8. A process for producing a heat resistance coating film, comprising: coating the resin composition according to claim 5 onto a support substrate using a slit nozzle to form a coating film; drying the coating film under reduced pressure to form a resin film; exposing the resin film; developing the exposed resin film; and applying heat treatment to the developed resin film.

9. The process for producing a heat resistance coating film according to claim 7, wherein the step of applying heat treatment to the resin film is performed at 250° C. or less.

10. The process for producing a heat resistance coating film according to claim 7, wherein residual stress of a resin forming a heat resistance coating film of a substrate with the heat resistance coating film obtained by the process for producing the heat resistance coating film is 30 MPa or less.

11. An electronic component mounted in such a state that one or a plurality of structures comprising a substrate and a coating film provided on one or both surfaces of the substrate are stacked, the coating film is a heat resistance coating film obtained by the production process according to claim 7.

12. An electronic component comprising a substrate, a rewiring structure comprising a coating film layer and a wiring layer alternately formed on the substrate, or a multilayer wiring structure, wherein the coating film layer is a heat resistance coating film obtained by the production process according to claim 7.

13. A display device comprising a first electrode provided on a substrate, an insulating layer provided on the first electrode such that the first electrode is partially exposed, and a second electrode provided facing the first electrode, wherein the insulating layer is a heat resistance coating film obtained by the production process according to claim 7.

14. A display element comprising a flattening film provided to cover concavoconvexes on a substrate comprising a thin film transistor (TFT) and a display element provided on the flattening film, wherein the flattening film is a heat resistance coating film obtained by the production process according to claim 7.

* * * * *